(12) United States Patent  
Taylor

(10) Patent No.: US 7,339,057 B2
(45) Date of Patent: Mar. 4, 2008

(54) METHOD FOR PREPARING FUSED OXAZINONES FROM ORTHO-AMINO AROMATIC CARBOXYLIC ACID AND CARBOXYLIC ACID IN THE PRESENCE OF A SULFONYL CHLORIDE AND PYRIDINE

(75) Inventor: Eric Deguyon Taylor, Newark, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 301 days.

(21) Appl. No.: 10/518,324

(22) PCT Filed: Jul. 29, 2003

(86) PCT No.: PCT/US03/23821

§ 371 (c)(1),
(2), (4) Date: Dec. 15, 2004

(87) PCT Pub. No.: WO2004/011447

PCT Pub. Date: Feb. 5, 2004

(65) Prior Publication Data

US 2005/0215785 A1     Sep. 29, 2005

Related U.S. Application Data

(60) Provisional application No. 60/446,438, filed on Feb. 11, 2003, provisional application No. 60/400,352, filed on Jul. 31, 2002.

(51) Int. Cl.
*C07D 413/04* (2006.01)
*C07D 413/14* (2006.01)

(52) U.S. Cl. .......................................... 544/92; 544/94

(58) Field of Classification Search .................. 544/92, 544/94
See application file for complete search history.

(56) References Cited

U.S. PATENT DOCUMENTS

2004/0171649 A1    9/2004    Annis et al.

(Continued)

FOREIGN PATENT DOCUMENTS

WO     WO 01/70671 A2    9/2001

(Continued)

OTHER PUBLICATIONS

G.M. Coppola, The Chemistry of 4H-3,1-Benzoxazin-4-Ones, J. Heterocyclic Chemistry, 1999, pp. 563-588, vol. 36.

(Continued)

*Primary Examiner*—Kahsay Habte

(57) ABSTRACT

A method for preparing a fused oxazinone is disclosed in which (1) a carboxylic acid is contacted with a sulfonyl chloride in the presence of an optionally substituted pyridine compound, the nominal mole ratio of sulfonyl chloride to carboxylic acid being from about 0.75 to 1.5; (2) the mixture prepared in (1) is contacted with an ortho-amino aromatic carboxylic acid in the presence of an optionally substituted pyridine compound, the nominal mole ratio of the ortho-amino aromatic carboxylic acid to carboxylic acid charged in (1) being from about 0.8 to 1.2; and (3) additional sulfonyl chloride is added to the mixture prepared in (2), the nominal mole ratio of additional sulfonyl chloride added in (3) to carboxylic acid charged in (1) being at least about 0.5. Also disclosed is a method for preparing a compound of Formula III, using a compound of Formula 1a that is characterized by preparing the fused oxazinone of Formula 1a by the method above, using a compound of the formula $LS(O)_2Cl$ as the sulfonyl chloride, a compound of Formula 2' as the carboxylic acid, and a compound of Formula 5' as the ortho-amino aromatic carboxylic acid (FORMULA 1a) (FORMULA III) (FORMULA 2') (FORMULA 5') wherein L, X, Y and $R^1$ through $R^9$ are as defined in the disclosure

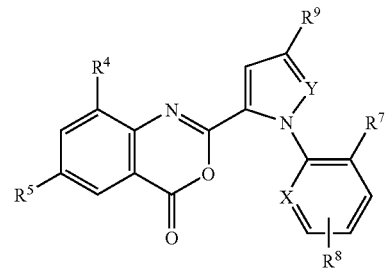

(1a)

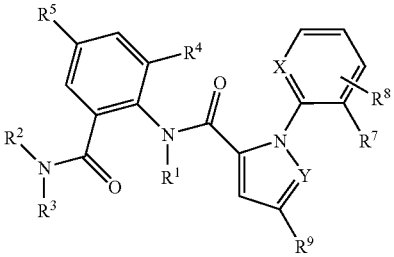

(III)

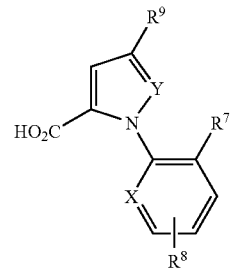

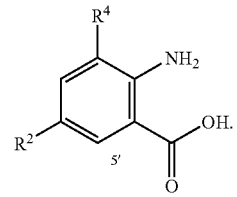

(2')

13 Claims, No Drawings

U.S. PATENT DOCUMENTS

| | | |
|---|---|---|
| 2004/0198984 A1 | 10/2004 | Lahm et al. |
| 2004/0198987 A1 | 10/2004 | Freudenberger et al. |
| 2004/0209923 A1 | 10/2004 | Berger et al. |
| 2005/0075372 A1 | 4/2005 | Lahm et al. |

FOREIGN PATENT DOCUMENTS

| | | |
|---|---|---|
| WO | WO 03/015518 A1 | 2/2003 |
| WO | WO 03/015519 A1 | 2/2003 |
| WO | WO 03/016282 A2 | 2/2003 |
| WO | WO 03/016283 A1 | 2/2003 |
| WO | WO 03/024222 | 3/2003 |
| WO | WO 04/011453 | 2/2004 |

OTHER PUBLICATIONS

Jakobsen et. al., Inhibitors of the Tissue Factor/Factor VIIA-Induced Coagulation: Synthesis and In Vitro Evaluation of Novel 2-Aryl Substituted Pyrido[3,4-D]-, Pyrido [2,3-D][1,3], Pyrazino[2,3-D][1,3]-, Pyrimido [4,5-D][1,3]-, Thieno [3,2-D][1,3]-, and Thieno [2,3-D][1,3 ]-Oxazin-4-Ones, Biorganic and Medicinal Chemistry, 2000, pp. 2803-2812, vol. 8.

Jakobsen et al., Inhibitors of the Tissue Factor/Factor VIIA-Induced Coagulation: Synthesis and In Vitro Evaluation of Novel Specific 2-Aryl Substituted 4H-3,1-Benzoxazin-4-Ones, Biorganic and Medicinal Chemistry, pp. 2095-2103, vol. 8, (2000).

D.V. Ramana et. al., Facile Synthesis of 2-Aryl-4H-3,1-Benzoxazin-4-Ones, Org. Prep. Proced. Int., 1993, pp. 588-590, 1993, vol. 25.

METHOD FOR PREPARING FUSED OXAZINONES FROM ORTHO-AMINO AROMATIC CARBOXYLIC ACID AND CARBOXYLIC ACID IN THE PRESENCE OF A SULFONYL CHLORIDE AND PYRIDINE

This application represents a national filing under 35 USC 371 of International Application No. PCT/US2003/023821 filed Jul. 29, 2003 and claims Priority of U.S. Provisional Application No. 60/446,438 filed Feb. 11, 2003 and U.S. Provisional Application No. 60/400,352 filed Jul. 31, 2002.

BACKGROUND OF THE INVENTION

A need exists for additional methods for preparing fused oxazinones. Such compounds include intermediates for the preparation of crop protection agents, pharmaceuticals and other fine chemicals.

Fused oxazinones have been prepared by a variety of methods. For example, N-acylanthranilic acids have been treated with acetic anhydride, anthranilic acids have been treated with carboxylic acid anhydrides, and anthranilic acids and carboxylic acids have been coupled in the presence of various dehydrating agents (see G. M. Coppola, *J. Heterocyclic Chemistry* 1999, 36, 563-588). Fused oxazinones have also been prepared by treatment of ortho-amino carboxylic acids with carboxylic acid chlorides in the presence of base (see e.g., Jakobsen et al., *Biorganic and Medicinal Chemistry* 2000, 8, 2803-2812 and Jakobsen et al., *Biorganic and Medicinal Chemistry* 2000, 8, 2095-2103). Benzoxazinones have also been prepared by treatment of a carboxylic acid with a sulfonyl chloride and then treatment with an anthranilic acid (see D. V. Ramana and E. Kantharaj, *Org. Prep. Proced. Int.* 1993, 25, 588).

SUMMARY OF THE INVENTION

This invention provides a method for preparing a fused oxazinone. This method comprises:

(1) contacting a carboxylic acid with a sulfonyl chloride in the presence of an optionally substituted pyridine compound, the nominal mole ratio of sulfonyl chloride to carboxylic acid being from about 0.75 to 1.5;

(2) contacting the mixture prepared in (1) with an ortho-amino aromatic carboxylic acid in the presence of an optionally substituted pyridine compound, the nominal mole ratio of the ortho-amino aromatic carboxylic acid to carboxylic acid charged in (1) being from about 0.8 to 1.2; and (3) adding additional sulfonyl chloride to the mixture prepared in (2), the nominal mole ratio of additional sulfonyl chloride added in (3) to carboxylic acid charged in (1) being at least about 0.5.

This invention also relates to a method for preparing a compound of Formula III,

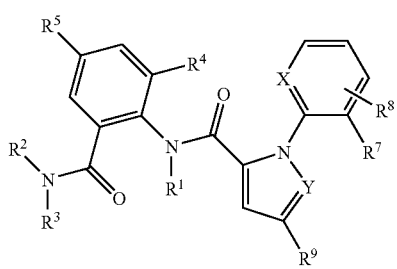

III wherein
X is N or $CR^6$;
Y is N or CH;
$R^1$ is H;
$R^2$ is H or $CH_3$;
$R^3$ is $C_1$-$C_6$ alkyl;
$R^4$ is $C_1$-$C_4$ alkyl or halogen;
$R^5$ is H, $C_1$-$C_4$ alkyl, $C_1$-$C_4$ haloalkyl or halogen;
$R^6$ and $R^7$ are independently H, $C_1$-$C_4$ alkyl, $C_1$-$C_4$ haloalkyl, halogen, CN or $C_1$-$C_4$ haloalkoxy;
$R^8$ is H, $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylmino, ($C_1$-$C_4$ alkyl)($C_3$-$C_6$ cycloalkyl)amino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl;
$R^9$ is $CF_3$, $OCF_3$, $OCHF_2$, $OCH_2CF_3$, $S(O)_pCF_3$, $S(O)_pCHF_2$ or halogen; and
p is 0, 1 or 2;

using a compound of Formula 1a

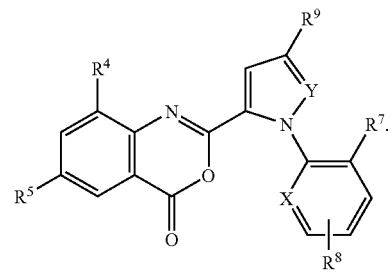

1a

This method is characterized by preparing the compound of Formula 1a (i.e. a subgenus of Formula 1 described below) by the method as indicated above. Formula 1a compounds may be prepared using a compound of the formula $LS(O)_2Cl$ (wherein L is selected from alkyl, haloalkyl and phenyl optionally substituted with from one to three substituents independently selected from alkyl or halogen) as the sulfonyl chloride, a compound of Formula 2' as the carboxylic acid, and a compound of Formula 5' as the ortho-amino aromatic carboxylic acid

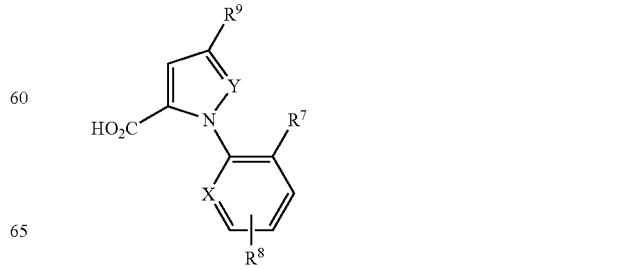

2'

-continued

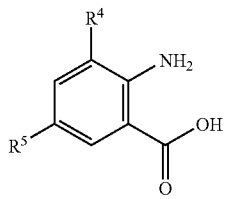  5'

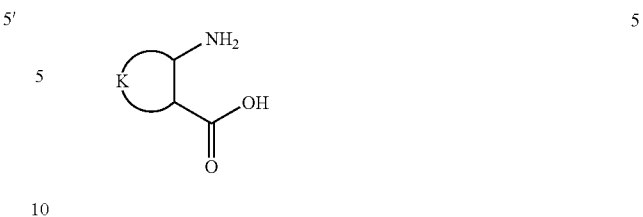  5

DETAILED DESCRIPTION OF THE INVENTION

One aspect of this invention involves the use of optionally substituted pyridine compounds together with sulfonyl chloride compounds to provide advantageous production of fused oxazinones. The optionally substituted pyridine compound is used (a) to facilitate contact between the carboxylic acid and the sulfonyl chloride compound and (b) to facilitate contact of the resulting mixture with the ortho-amino carboxylic acid. The sulfonyl chloride compound is used both (a) as a reactant to facilitate coupling of the carboxylic acid with the ortho-amino carboxylic acid and (b) as a reactant to facilitate ring closure to form the fused oxazinone. These aspects provide effective production of the fused oxazinone while limiting the amounts of the carboxylic acid and the ortho-amino carboxylic acid that are consumed during the formation of the fused oxazinone. This can be especially important when the carboxylic acid and/or the ortho-amino carboxylic acid are valuable, complex and/or difficult to obtain. For example, this invention may be used for preparing a compound of Formula 1

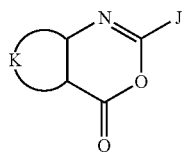  1 wherein
J is an optionally substituted carbon moiety, and
K is, together with the two contiguous linking carbon atoms, a fused phenyl ring or a fused 5- or 6-membered heteroaromatic ring, each ring optionally substituted.

More particularly, a compound of Formula 1 may be prepared by a method comprising (1) contacting a carboxylic acid of Formula 2

 J—CO$_2$H    2 with a sulfonyl chloride of Formula 4

 LS(O)$_2$Cl    4 wherein L is selected from alkyl, haloalkyl, and phenyl optionally substituted with from one to three substituents independently selected from alkyl or halogen;
in the presence of an optionally substituted pyridine compound;
(2) contacting the mixture prepared in (1) with an ortho-amino carboxylic acid of Formula 5 in the presence of an optionally substituted pyridine compound; and
(3) contacting the mixture prepared in (2) with additional sulfonyl chloride of Formula 4.

In the recitations herein, the term "carbon moiety" refers to a radical in which a carbon atom is connected to the backbone of the fused oxazinone ring of Formula 1 and the carboxylic acid group of Formula 2. As the carbon moiety L is separated from the reaction center, it can encompass a great variety of carbon-based moieties that can be prepared by modern methods of synthetic organic chemistry. The method of this invention is generally applicable to prepare a wide range of compounds of Formula 1.

"Carbon moiety" thus includes alkyl, alkenyl and alkynyl moieties, which can be straight-chain or branched.

"Carbon moiety" also includes carbocyclic and heterocyclic rings, which can be saturated, partially saturated, or completely unsaturated. The carbocyclic and heterocyclic rings of a carbon moiety group can form polycyclic ring systems comprising multiple rings connected together. The term "carbocyclic ring" denotes a ring wherein the atoms forming the ring backbone are selected only from carbon. "Saturated carbocyclic" refers to a ring having a backbone consisting of carbon atoms linked to one another by single bonds; unless otherwise specified, the remaining carbon valences are occupied by hydrogen atoms. The term "hetero" in connection with rings or ring systems refers to a ring or ring system in which at least one ring atom is not carbon and which can contain from one to four heteroatoms independently selected from the group consisting of nitrogen, oxygen and sulfur, provided that each ring contains no more than 4 nitrogens, no more than 2 oxygens and no more than 2 sulfurs. When the carbon moiety consists of a heterocyclic ring or ring system, it is connected to the backbone of the fused oxazinone ring of Formula 1 and the carboxylic acid group of Formula 2 through any available carbon ring atom by replacement of a hydrogen on said carbon atom. Heterocyclic rings or ring systems may also be connected to the carbon moiety through any available carbon or nitrogen atom by replacement of a hydrogen on said carbon or nitrogen atom.

Although there is no definite limit to the size of Formula 1 suitable for the process of the invention, typically Formula 1 comprises 9-100, more commonly 9-50, and most commonly 9-25 carbon atoms, and 3-25, more commonly 3-15, and most commonly 3-10 heteroatoms. Heteroatoms are atoms other than carbon or hydrogen and are commonly selected from halogen, oxygen, sulfur, nitrogen, phosphorus and silicon. Three heteroatoms in Formula 1 are the nitrogen atom and the two oxygen atoms in the oxazinone moiety. When K is a fused heteroaromatic ring or when the carbon moiety comprises a heterocyclic ring, additional heteroatoms are contained therein. Substituents attached to the K ring or the carbon moiety may also contain additional heteroatoms.

Unsaturated rings can be aromatic if Hückel's rule is satisfied. "Aromatic" indicates that each of the ring atoms is essentially in the same plane and has a p-orbital perpendicular to the ring plane, and in which (4n+2) π electrons, when n is 0 or a positive integer, are associated with the ring to comply with Hückel's rule. The term "aromatic ring system" denotes fully unsaturated carbocycles and heterocycles in which at least one ring of a polycyclic ring system is aromatic. The term "aromatic carbocyclic ring or ring system" includes fully aromatic carbocycles and carbocycles in which at least one ring of a polycyclic ring system is aromatic (e.g., phenyl, naphthyl and 1,2,3,4-tetrahydro-naphthalenyl). The term "nonaromatic carbocyclic ring or ring system" denotes fully saturated carbocycles as well as partially or fully unsaturated carbocycles where the Hückel rule is not satisfied by any of the rings in the ring system. The terms "heteroaromatic ring or ring system" and "aromatic fused heterobicyclic ring system" includes fully aromatic heterocycles and heterocycles in which at least one ring of a polycyclic ring system is aromatic (where aromatic indicates that the Hückel rule is satisfied). The term "nonaromatic heterocyclic ring or ring system" denotes fully saturated heterocycles as well as partially or fully unsaturated heterocycles where the Hückel rule is not satisfied by any of the rings in the ring system. The term "aryl" denotes a carbocyclic or heterocyclic ring or ring system in which at least one ring is aromatic, and the aromatic ring provides the connection to the remainder of the molecule.

The carbon moiety specified for J is optionally substituted. Also, the K ring moieties of Formulae 1 and 5 are optionally substituted. Furthermore, the pyridine compound employed in the method of the invention (hereafter Formula 3) is optionally substituted. The term "optionally substituted" in connection with these groups refers to groups that are unsubstituted or have at least one non-hydrogen substituent. Illustrative optional substituents include alkyl, alkenyl, cycloalkyl, cycloalkenyl, aryl, hydroxycarbonyl, formyl, alkylcarbonyl, alkenylcarbonyl, alkynylcarbonyl, alkoxycarbonyl, hydroxy, alkoxy, alkenyloxy, alkynyloxy, cycloalkoxy, aryloxy, alkylthio, alkenylthio, alkynylthio, cycloalkylthio, arylthio, alkylsulfinyl, alkenylsulfinyl, alkynylsulfinyl, cycloalkylsulfinyl, arylsulinyl, alkylsulfonyl, alkenylsulfonyl, alkynylsulfonyl, cycloalkylsulfonyl, arylsulfonyl, amino, alkylamino, alkenylamino, alkynylamino, arylamino, aminocarbonyl, alkylaminocarbonyl, alkenylaminocarbonyl, alkynylaminocarbonyl, arylaminocarbonyl, alkylaminocarbonyl, alkenylaminocarbonyl, alkynylaminocarbonyl, arylaminocarbonyloxy, alkoxycarbonylamino, alkenyloxycarbonylamino, alkynyloxycarbonylamino and aryloxycarbonylamino, silyl moieties and siloxy moieties, each further optionally substituted; halogen; cyano; and nitro. The optional further substituents are independently selected from groups like those illustrated above for the substituents themselves to give additional substituent groups for J and K such as haloalkyl, haloalkenyl and haloalkoxy. As another example, alkylamino can be further substituted with alkyl, giving dialkylamino. The substituents can also be tied together by figuratively removing one or two hydrogen atoms from each of two substituents or a substituent and the supporting molecular structure and joining the radicals to produce cyclic and polycyclic structures fused or appended to the molecular structure supporting the substituents. For example, tying together adjacent hydroxy and methoxy groups attached to, for example, a phenyl ring gives a fused dioxolane structure containing the linking group —O—CH$_2$—O—. Tying together a hydroxy group and the molecular structure to which it is attached can give cyclic ethers, including epoxides. Illustrative substituents also include oxygen, which when attached to carbon forms a carbonyl function or when attached to nitrogen forms an N-oxide.

One skilled in the art will appreciate that not all nitrogen-containing heterocycles can form N-oxides since the nitrogen requires an available lone pair for oxidation to the oxide; one skilled in the art will recognize those nitrogen containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

As referred to herein, "alkyl", used either alone or in compound words such as "alkylthio" or "haloalkyl" includes straight-chain or branched alkyl, such as, methyl, ethyl, n-propyl, i-propyl, and the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkenyloxy" includes straight-chain or branched alkenyloxy moieties. Examples of "alkenyloxy" include H$_2$C=CHCH$_2$O, (CH$_3$)$_2$C=CHCH$_2$O, (CH$_3$)CH=CHCH$_2$O, (CH$_3$)CH=C(CH$_3$)CH$_2$O and CH$_2$=CHCH$_2$CH$_2$O. "Alkynyloxy" includes straight-chain or branched alkynyloxy moieties. Examples of "alkynyloxy" include HC≡CCH$_2$O, CH$_3$C≡CCH$_2$O and CH$_3$C≡CCH$_2$CH$_2$O. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include CH$_3$S(O), CH$_3$CH$_2$S(O), CH$_3$CH$_2$CH$_2$S(O), (CH$_3$)$_2$CHS(O) and the different butylsulfinyl, pentylsulfinyl and hexylsulfinyl isomers. Examples of "alkylsulfonyl" include CH$_3$S(O)$_2$, CH$_3$CH$_2$S(O)$_2$, CH$_3$CH$_2$CH$_2$S(O)$_2$, (CH$_3$)$_2$CHS(O)$_2$ and the different butylsulfonyl, pentylsulfonyl and hexylsulfonyl isomers. "Alkylamino", "alkenylthio", "alkenylsulfinyl", "alkenylsulfonyl", "alkynylthio", "allynylsulfinyl", "aLkynylsulfonyl", and the like, are defined analogously to the above examples. Examples of "alkylcarbonyl" include C(O)CH$_3$, C(O)CH$_2$CH$_2$CH$_3$ and C(O)CH(CH$_3$)$_2$.

Examples of "alkoxycarbonyl" include CH₃C(=O), CH₃CH₂C(=O), CH₃CH₂CH₂C(=O), (CH₃)₂CHOC(=O) and the different butoxy- or pentoxycarbonyl isomers. "Cycloalkyl" includes, for example, cyclopropyl, cyclobutyl, cyclopentyl, cyclohexyl, cycloheptyl and cyclooctyl. The term "cycloalkoxy" includes the same groups linked through an oxygen atom such as cyclopentyloxy and cyclohexyloxy. "Cycloalkylamino" means the amino nitrogen atom is attached to a cycloalkyl radical and a hydrogen atom and includes groups such as cyclopropylamino, cyclobutylamino, cyclopentylamino and cyclohexylamino. "(Alkyl)(cycloalkyl)amino" (or "(alkyl)cycloalkylamino") means a cycloalkylamino group where the hydrogen atom is replaced by an alkyl radical; examples include groups such as (methyl)(cyclopropyl)amino, (butyl)(cyclobutyl)amino, (propyl)cyclopentylamino, (methyl)cyclohexylamino and the like. "Cycloalkenyl" includes groups such as cyclopentenyl and cyclohexenyl as well as groups with more than one double bond such as 1,3- and 1,4-cyclohexadienyl.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include F₃C, ClCH₂, CF₃CH₂ and CF₃CCl₂.

The term "silyl moieties" refers to moieties containing at least one silicon atom bonded to the remainder of Formula 1 through said silicon atom and includes groups such as trialkylsilyl (examples include trimethylsilyl, triisopropylsilyl and dimethyl-t-butylsilyl) and dialkylarylsilyl groups (e.g. dimethylphenylsilyl). The term "siloxy moieties" refers to moieties containing at least one silicon atom bonded to an oxygen atom and connected to the remainder of Formula 1 through said oxygen atom and includes groups such as trialkylsiloxy (examples include trimethylsiloxy, triisopropylsiloxy and dimethyl-t-butylsiloxy) and dialkylarylsilyl groups (e.g. dimethylphenylsiloxy).

The total number of carbon atoms in a substituent group is indicated by the "$C_i$-$C_j$" prefix where i and j are, for example, numbers from 1 to 3; e.g., $C_1$-$C_3$ alkyl designates methyl through propyl.

There is no definite limit to the nature and size of the substituents on the pyridine of Formula 3, but the substituents are commonly alkyl, more particularly $C_1$-$C_6$, more commonly $C_1$-$C_4$, and most commonly $C_1$ (i.e. methyl). Typical examples of compounds of Formula 3 are pyridine, the picolines (i.e. 2-methylpyridine, 3-methylpyridine, 4-methylpyridine), the lutidines (e.g., 2,3-dimethylpyridine, 2,4-dimethylpyridine, 2,5-dimethylpyridine, 2,5-dimethylpyridine, 3,4-dimethylpyridine, 3,5-dimethylpyridine) and collidine. Other common substituents are dimethylamino (e.g., 4-(dimethylamino)pyridine) and pyrrolidino (e.g., 4-(pyrrolidino)pyridine). Furthermore, two substituents on Formula 3 can be tied together as already described to form other common pyridine derivatives, such as quinoline and isoquinoline. These quinoline and isoquinoline pyridine derivatives can also be further substituted.

Although there is no definite limit to the size of J, optionally substituted alkyl moieties in J commonly include 1 to 6 carbon atoms, more commonly 1 to 4 carbon atoms, and most commonly 1 or 2 carbon atoms in the alkyl chain. Similarly, optionally substituted alkenyl and alkynyl moieties in J commonly include 2 to 6 carbon atoms, more commonly 2 to 4 carbon atoms, and most commonly 2 or 3 carbon atoms in the alkenyl or alkynyl chain.

As indicated above, the carbon moiety J may be (among others) an aromatic ring or ring system. Examples of aromatic rings or ring systems include a phenyl ring, 5- or 6-membered heteroaromatic rings, aromatic 8-, 9- or 10-membered fused carbobicyclic ring systems and aromatic 8-, 9- or 10-membered fused heterobicyclic ring systems, wherein each ring or ring system is optionally substituted. The term "optionally substituted" in connection with these J groups refers to groups that are unsubstituted or have at least one non-hydrogen substituent. These carbon moieties may be substituted with as many optional substituents as can be accommodated by replacing a hydrogen atom with a non-hydrogen substituent on any available carbon or nitrogen atom. Commonly, the number of optional substituents (when present) ranges from one to four. An example of phenyl optionally substituted with from one to four substituents is the ring illustrated as U-1 in Exhibit 1, wherein $R^v$ is any substituent and r is an integer from 0 to 4. Examples of aromatic 8-, 9- or 10-membered fused carbobicyclic ring systems optionally substituted with from one to four substituents include a naphthyl group optionally substituted with from one to four substituents illustrated as U-85 and a 1,2,3,4-tetrahydronaphthyl group optionally substituted with from one to four substituents illustrated as U-86 in Exhibit 1, wherein $R^v$ is any substituent and r is an integer from 0 to 4. Examples of 5- or 6-membered heteroaromatic rings optionally substituted with from one to four substituents include the rings U-2 through U-53 illustrated in Exhibit 1 wherein $R^v$ is any substituent and r is an integer from 0 to 4. Examples of aromatic 8-, 9- or 10-membered fused heterobicyclic ring systems optionally substituted with from one to four substituents include U-54 through U-84 illustrated in Exhibit 1 wherein $R^v$ is any substituent and r is an integer from 0 to 4. Other examples of J include a benzyl group optionally substituted with from one to four substituents illustrated as U-87 and a benzoyl group optionally substituted with from one to four substituents illustrated as U-88 in Exhibit 1, wherein $R^v$ is any substituent and r is an integer from 0 to 4.

Although $R^v$ groups are shown in the structures U-1 through U-85, it is noted that they do not need to be present since they are optional substituents. The nitrogen atoms that require substitution to fill their valence are substituted with H or $R^v$. Note that some U groups can only be substituted with less than 4 $R^v$ groups (e.g. U-14, U-15, U-18 through U-21 and U-32 through U-34 can only be substituted with one $R^v$). Note that when the attachment point between $(R^v)_r$ and the U group is illustrated as floating; $(R^v)_r$ can be attached to any available carbon atom or nitrogen atom of the U group. Note that when the attachment point on the U group is illustrated as floating, the U group can be attached to the remainder of Formula I through any available carbon of the U group by replacement of a hydrogen atom.

Exhibit 1

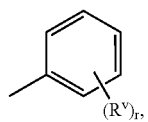

U-1

-continued
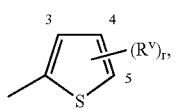 U-2
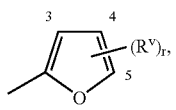 U-3
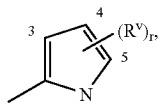 U-4
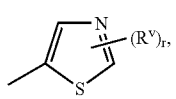 U-5
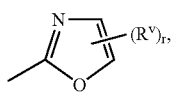 U-6
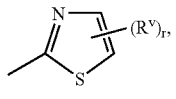 U-7
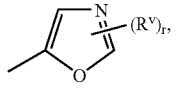 U-8
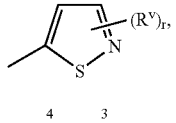 U-9
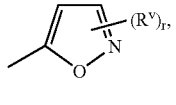 U-10
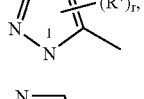 U-11
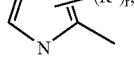 U-12
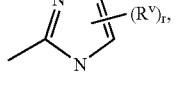 U-13
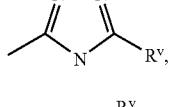 U-14
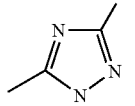 U-15
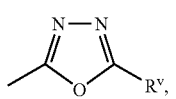 U-16
-continued
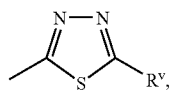 U-17
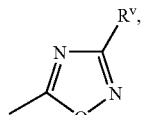 U-18
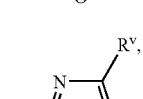 U-19
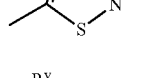 U-20
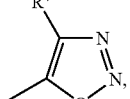 U-21
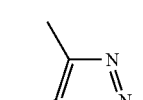 U-22
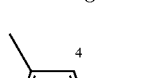 U-23
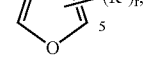 U-24
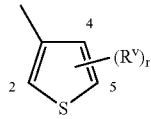 U-25
 U-26
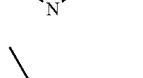 U-27
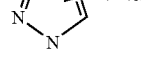 U-28
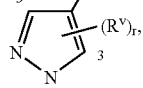
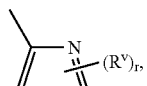
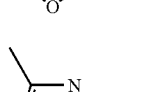

-continued
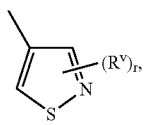, U-29
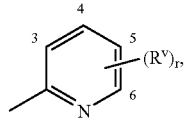, U-41
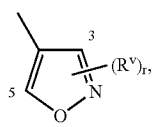, U-30
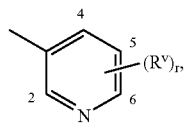, U-42
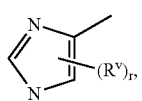, U-31
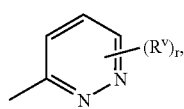, U-43
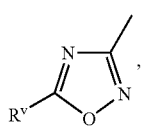, U-32
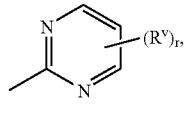, U-44
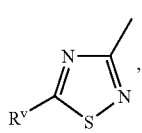, U-33
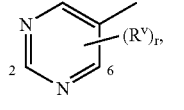, U-45
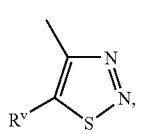, U-34
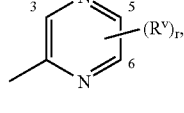, U-46
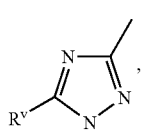, U-35
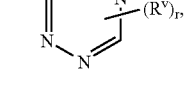, U-47
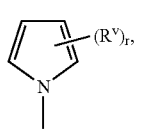, U-36
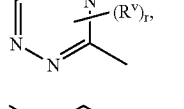, U-48
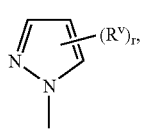, U-37
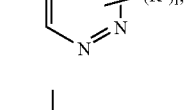, U-49
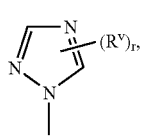, U-38
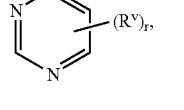, U-50
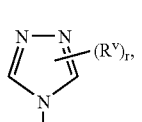, U-39
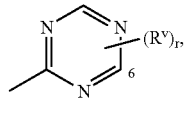, U-51
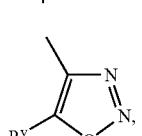, U-40
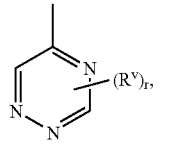, U-52

-continued
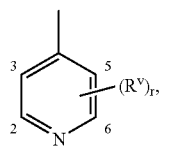 U-53
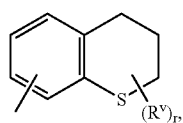 U-54
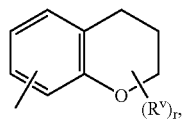 U-55
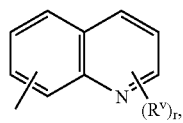 U-56
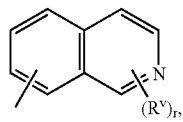 U-57
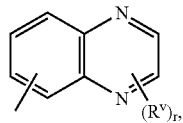 U-58
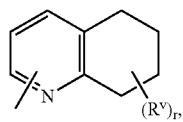 U-59
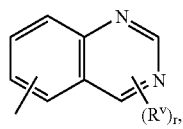 U-60
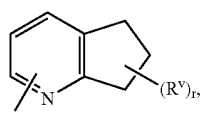 U-61
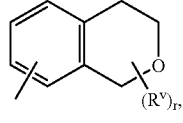 U-62
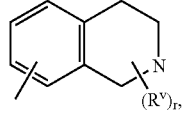 U-63
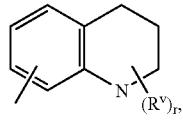 U-64
-continued
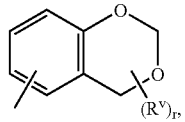 U-65
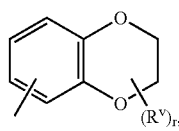 U-66
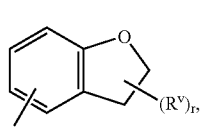 U-67
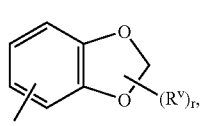 U-68
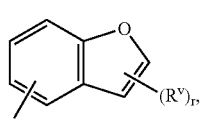 U-69
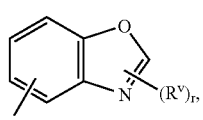 U-70
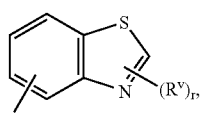 U-71
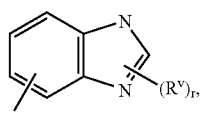 U-72
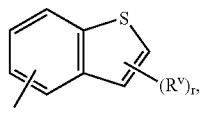 U-73
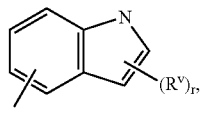 U-74
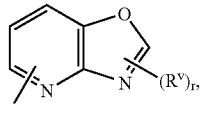 U-75
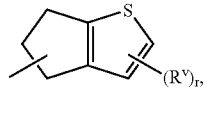 U-76
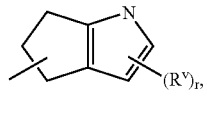 U-77

-continued

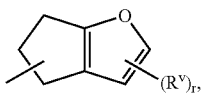 U-78

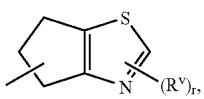 U-79

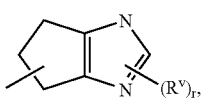 U-80

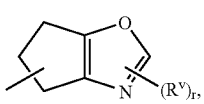 U-81

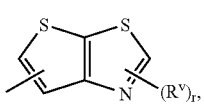 U-82

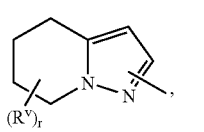 U-83

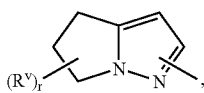 U-84

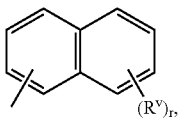 U-85

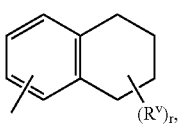 U-86

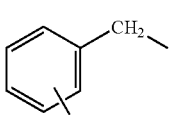 U-87 or

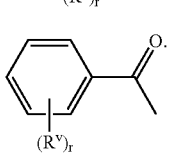 U-88

As indicated above, the carbon moiety J may be (among others) saturated or partially saturated carbocyclic and heterocyclic rings, which can be further optionally substituted. The term "optionally substituted" in connection with these J groups refers to groups that are unsubstituted or have at least one non-hydrogen substituent. These carbon moieties may be substituted with as many optional substituents as can be accommodated by replacing a hydrogen atom with a non-hydrogen substituent on any available carbon or nitrogen atom. Commonly, the number of optional substituents (when present) ranges from one to four. Examples of saturated or partially saturated carbocyclic rings include optionally substituted $C_3$-$C_8$ cycloalkyl and optionally substituted $C_3$-$C_8$ cycloalkenyl. Examples of saturated or partially saturated heterocyclic rings include optionally substituted 5- or 6-membered nonaromatic heterocyclic rings optionally including one or two ring members selected from the group consisting of C(=O), SO or S(O)$_2$. Examples of such J groups include those illustrated as G-1 through G-35 in Exhibit 2. Note that when the attachment point on these G groups is illustrated as floating, the G group can be attached to the remainder of Formula 1 through any available carbon or nitrogen of the G group by replacement of a hydrogen atom. The optional substituents can be attached to any available carbon or nitrogen by replacing a hydrogen atom (said substituents are not illustrated in Exhibit 2 since they are optional substituents). Note that when G comprises a ring selected from G-24 through G-31, G-34 and G-35, $Q^2$ may be selected from O, S, NH or substituted N.

Exhibit 2

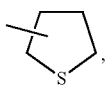 G-1

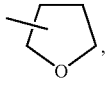 G-2

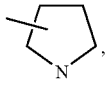 G-3

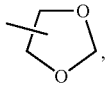 G-4

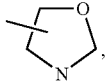 G-5

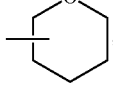 G-6

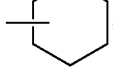 G-7

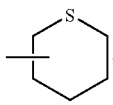 G-8

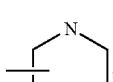 G-9

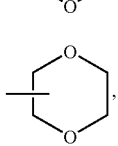 G-10

-continued

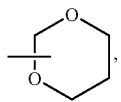

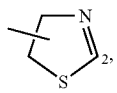

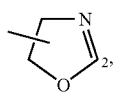

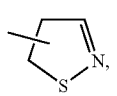

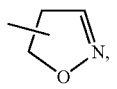

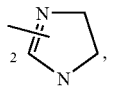

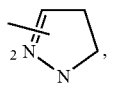

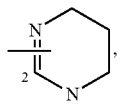

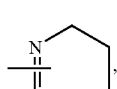

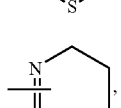

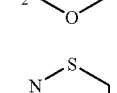

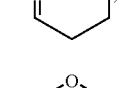

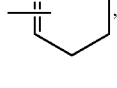

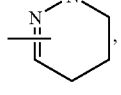

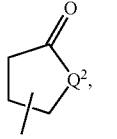

G-11

G-12

G-13

G-14

G-15

G-16

G-17

G-18

G-19

G-20

G-21

G-22

G-23

G-24

-continued

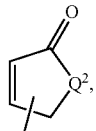

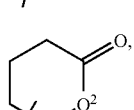

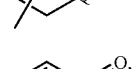

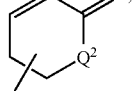

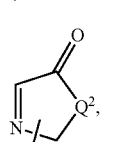

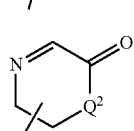

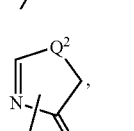

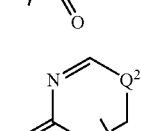

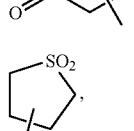

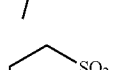

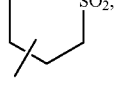

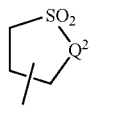

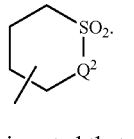

G-25

G-26

G-27

G-28

G-29

G-30

G-31

G-32

G-33

G-34 and

G-35

It is noted that the J group may be optionally substituted. As noted above, a J group may commonly comprise a U group or a G group further substituted with from one to four substituents. Thus J groups may comprise a U group or a G group selected from U-1 through U-88 or G-1 through G-35, and further substituted with additional substituents including from one to four U or G groups (which may be the same or different) and both the core U or G group and substituent U or G groups optionally further substituted. Of note are J groups comprising a U or G group substituted with one U or G group and optionally substituted with from one to three additional substituents. For example, J can be U-11, in which an $R^v$ attached to the 1-nitrogen is the group U-41.

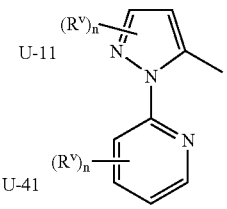

As noted above, K is, together with the two contiguous linking carbon atoms, a fused phenyl ring or a fused 5- or 6-membered heteroaromatic ring, each ring optionally substituted. The term "optionally substituted" in connection with these K rings refers to K rings that are unsubstituted or have at least one non-hydrogen substituent. An example of a K ring wherein the K ring is optionally substituted with from one to four $R^t$ includes the ring system illustrated as K-38 (fused phenyl ring) in Exhibit 3 wherein n is an integer from 0 to 4 and $R^t$ is any substituent Example of said K rings wherein the K ring is optionally substituted with from one to three $R^t$ include the ring systems K-1 to K-37 (5- or 6-membered heteroaromatic rings) in Exhibit 3, wherein n is an integer from 0 to 3 and $R^t$ is any substituent. As with the carbon atoms in the ring, the nitrogen atoms that require substitution to fill their valence are substituted with hydrogen or with Rt. Although $(R^t)_n$ groups are shown in the structures K-1 to K-38, it is noted that $R^t$ does not need to be present since it is an optional substituent. Note that some K rings can only be substituted with less than 3 $R^t$ groups (e.g. K-7 through K-10, K-15, K-16, K-20, K-21, K-23, K-24, K-26 and K-27 can only be substituted with one $R^t$). In the exemplified K groups, the upper right bond is attached through the available linking carbon atom to the nitrogen atom of the oxazinone portion of Formula 1 and the lower right bond is attached through the available linking carbon atom to the carbonyl atom of the oxazinone portion of Formula 1. The wavy line indicates that the K ring is attached to the remainder of Formula 1 as illustrated below.

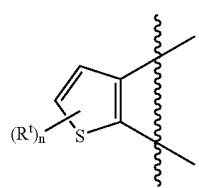

Exhibit 3

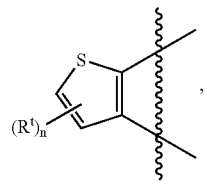

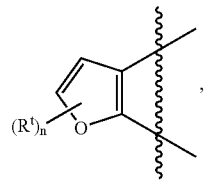

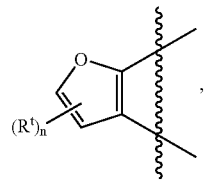

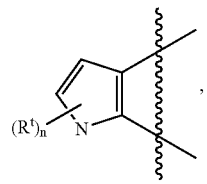

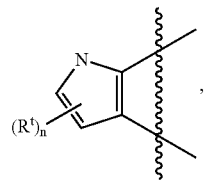

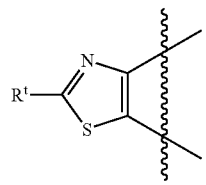

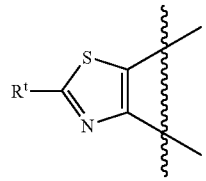

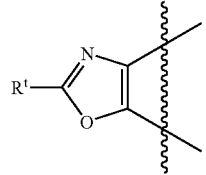

-continued
K-10 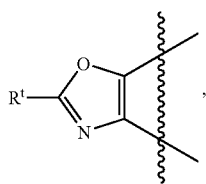
K-11 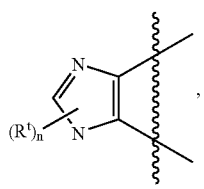
K-12 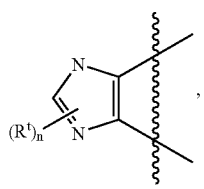
K-13 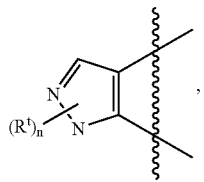
K-14 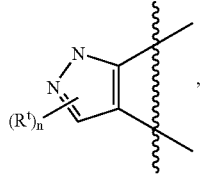
K-15 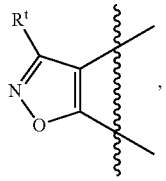
K-16 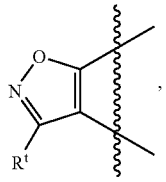
K-17 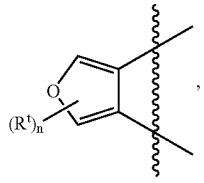
-continued
K-18 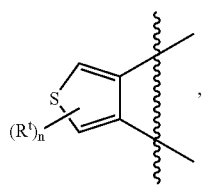
K-19 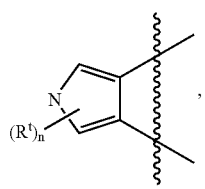
K-20 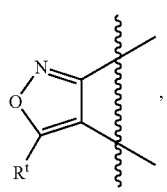
K-21 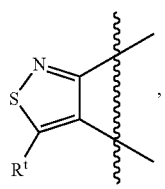
K-22 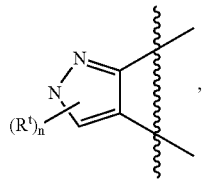
K-23 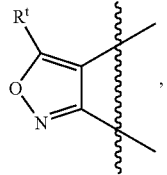
K-24 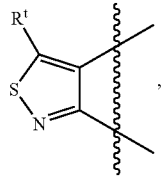
K-25 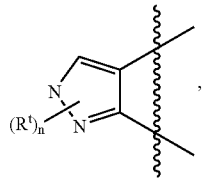

K-26 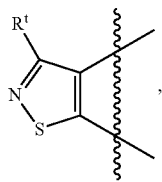,

K-27 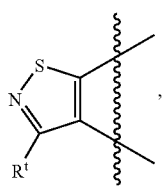,

K-28 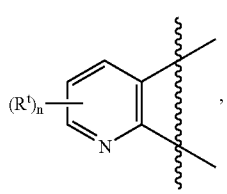,

K-29 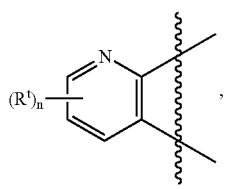,

K-30 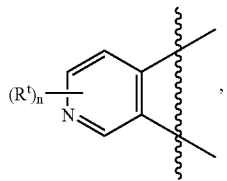,

K-31 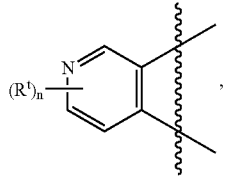,

K-32 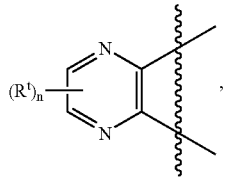,

K-33 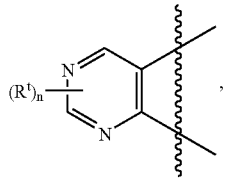,

K-34 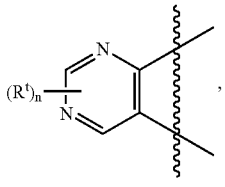,

K-35 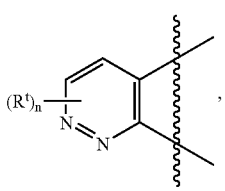,

K-36 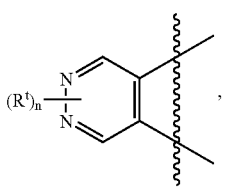,

K-37 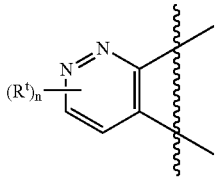 and

K-38 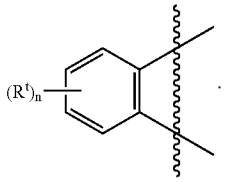.

Of note are K rings including optionally substituted thiophene, isoxazole, isothiazole, pyrazole, pyridine and pyrimidine rings. Of particular note are K rings K-1, K-14, K-15, K-18, K-23, K-28, K-29, K-30, K-31 and K-33, especially K-28, K-31 and K-33. Also of particular note is K-38 (optionally substituted phenyl).

Examples of optional substituents that can be attached to the U, G or K groups illustrated above include substituents selected from W. The K rings may also be substituted with the previously described optionally substituted U or optionally substituted G groups.

Each W is independently $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, ($C_1$-$C_4$ alkyl)($C_3$-$C_6$ cycloalkyl)amino or $C_3$-$C_6$ trialkylsilyl.

Other suitable substituents include
$B(OR^{17})_2$; $NH_2$; SH; thiocyanato; $C_3$-$C_8$ trialkylsilyloxy, $C_1$-$C_4$ alkyldisulfide; $SF_5$; $R^{19}C(=E)$-; $R^{19}C(=E)M$-; $R^{19}MC(=E)$-; $(R^{19})MC(=E)M$-; $-OP(=O)(OR^{19})_2$; $-S(O)_2MR^{19}$; $R^{19}S(O)_2M$-;

wherein
  each E is independently O, S, $NR^{15}$, $NOR^{15}$, $NN(R^{15})_2$, N—S=O, N—CN or N—$NO_2$;
  each M is independently O, $NR^{18}$ or S;
  Q is O or S;
  each $R^{15}$ and each $R^{19}$ is independently H; $C_1$-$C_6$ alkyl optionally substituted with one or more substituents selected from the group consisting of CN, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $CO_2H$, $C_2$-$C_6$ alkoxycarbonyl, $C_2$-$C_6$ alkylcarbonyl, $C_3$-$C_6$ trialkylsilyl, and a phenyl ring optionally substituted with one to three substituents independently selected from W; $C_1$-$C_6$ haloalkyl; $C_3$-$C_6$ cycloalkyl; or a phenyl ring optionally substituted with from one to three substituents independently selected from W;
  each $R^{17}$ is independently H or $C_1$-$C_4$ alkyl; or
  $B(OR^{17})_2$ can form a ring wherein the two oxygen atoms are linked by a chain of two to three carbons optionally substituted with one or two substituents independently selected from methyl or $C_2$-$C_6$ alkoxycarbonyl; and
  each $R^{18}$ is independently H, $C_1$-$C_6$ alkyl or $C_1$-$C_6$ haloalkyl.

Of note are methods for preparing compounds of Formula 1 wherein J is $C_1$-$C_6$ alkyl, $C_2$-$C_6$ alkenyl, $C_2$-$C_6$ alkynyl, $C_3$-$C_8$ cycloalkyl or $C_3$-$C_8$ cycloalkenyl, each optionally substituted; or J is a phenyl ring, a benzyl group, a benzoyl group, a 5- or 6-membered heteroaromatic ring, an aromatic 8-, 9- or 10-membered fused carbobicyclic ring system, an aromatic 8-, 9- or 10-membered fused heterobicyclic ring system or a 5- or 6-membered nonaromatic heterocyclic ring optionally including one or two ring members selected from the group consisting of C(=O), SO or $S(O)_2$, each optionally substituted. Of particular note are such methods wherein
  K is, together with the two contiguous linking carbon atoms, a fused phenyl ring optionally substituted with from one to four substituents independently selected from G, U, W or $R^{13}$; or a fused 5- or 6-membered heteroaromatic ring optionally substituted with from one to three substituents independently selected from G, U, W or $R^{13}$;
  J is $C_1$-$C_6$ alkyl, $C_2$-$C_6$ alkenyl, $C_2$-$C_6$ alkynyl, $C_3$-$C_8$ cycloalkyl or $C_3$-$C_8$ cycloalkenyl, each optionally substituted with one or more substituents selected from the group consisting of $R^{12}$, halogen, CN, $NO_2$, hydroxy, $C_1$-$C_4$ alkoxy, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino and ($C_1$-$C_4$ alkyl)($C_3$-$C_6$ cycloalkyl)amino; or
  J is a phenyl ring, a benzyl group, a benzoyl group, a 5- or 6-membered heteroaromatic ring, an aromatic 8-, 9- or 10-membered fused carbobicyclic ring system, an aromatic 8-, 9- or 10-membered fused heterobicyclic ring system or a 5- or 6-membered nonaromatic heterocyclic ring optionally including one or two ring members selected from the group consisting of C(=O), SO or $S(O)_2$, each optionally substituted with from one to four substituents independently selected from G, U, W or $R^{13}$;
  each G is a 5- or 6-membered nonaromatic heterocyclic ring optionally including one or two ring members selected from the group consisting of C(=O), SO or $S(O)_2$, each optionally substituted with from one to four substituents independently selected from W;
  each U is a phenyl ring, a benzyl group, a benzoyl group, a 5- or 6-membered heteroaromatic ring, an aromatic 8-, 9- or 10-membered fused carbobicyclic ring system, an aromatic 8-, 9- or 10-membered fused heterobicyclic ring system, each optionally substituted with from one to four substituents independently selected from W;
  each W is independently $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, ($C_1$-$C_4$ alkyl)($C_{3-6}$ cycloalkyl)amino or $C_3$-$C_6$ trialkylsilyl;
  each $R^{12}$ is independently $R^{19}C(=E)$-; $R^{19}C(=E)L$-; $R^{19}LC(=E)$-; ($R^{19}$)LC(=E)L; —O(Q=)$P(OR^{19})_2$; —$SO_2LR^{18}$; or $R^{19}SO_2L$-;
  each $R^{13}$ is $B(OR^{17})_2$; $NH_2$; SH; thiocyanato; $C_3$-$C_8$ trialkylsilyloxy, $C_1$-$C_4$ alkyldisulfide; $SF_5$; $R^{19}C(=E)$-; $R^{19}C(=E)M$-; $R^{19}MC(=E)$-, ($R^{19}$)MC(=E)M-; —OP(=O)$(OR^{19})_2$; —$S(O)_2MR^{19}$; $R^{19}S(O)_2M$-;
  each E is independently O, S, $NR^{15}$, $NOR^{15}$, $NN(R^{15})_2$, N—S=O, N—CN or N—$NO_2$;
  each M is independently O, $NR^{18}$ or S;
  Q is O or S;
  each $R^{15}$ and each $R^{19}$ is independently H; $C_1$-$C_6$ alkyl optionally substituted with one or more substituents selected from the group consisting of CN, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $CO_2H$, $C_2$-$C_6$ alkoxycarbonyl, $O_2$-$C_6$ alkylcarbonyl, $C_3$-$C_6$ trialkylsilyl, and a phenyl ring optionally substituted with one to three substituents independently selected from W; $C_1$-$C_6$ haloalkyl; $C_3$-$C_6$ cycloalkyl; or a phenyl ring optionally substituted with from one to three substituents independently selected from W;
  each $R^{17}$ is independently H or $C_1$-$C_4$ alkyl; or
  $B(OR^{17})_2$ can form a ring wherein the two oxygen atoms are linked by a chain of two to three carbons optionally substituted with one or two substituents independently selected from methyl or $C_2$-$C_6$ alkoxycarbonyl; and
  each $R^{18}$ is independently H, $C_1$-$C_6$ alkyl or $C_1$-$C_6$ haloalkyl.

Preferably, K is, together with the two contiguous linking carbon atoms, a fused phenyl ring optionally substituted with from one to four substituents independently selected from W or $R^{13}$.

The compounds of Formula 1 can be prepared by one or more of the following methods and variations as described in Schemes 1-27. The definitions of J, K, L, M, $R^4$, through $R^9$, $R^v$ X, Y and n in the compounds of Formulae 2-76 below are as defined above. Compounds of Formulae 1a, 2a-p and 5a-c are various subsets of the compounds of Formulae 1, 2 and 5, respectively. Of note are compounds wherein K is selected from the group consisting of optionally substituted thiophene, isoxazole, isothiazole, pyrazole, pyridine and pyrimidine rings. Also of note are compounds wherein K is K-1, K-14, K-15, K-18, K-23, K-28, K-29, K-30, K-31 and K-33. Of particular note are compounds of the formulae wherein K is K-28, K-31 and K-33. Also of particular note are compounds wherein K is an optionally substituted fused phenyl ring (K-38).

As shown in Scheme 1, according to the method of this invention a fused oxazinone of Formula 1 is prepared via coupling of a carboxylic acid of Formula 2 with an ortho-amino carboxylic acid of Formula 5.

Scheme 1

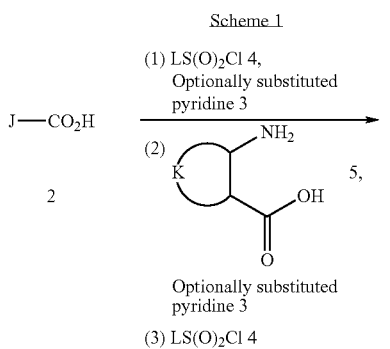

(1) LS(O)₂Cl 4,
Optionally substituted
pyridine 3

(2) [anthranilic acid structure]

Optionally substituted
pyridine 3

(3) LS(O)₂Cl 4

The reaction sequence (i.e. Steps (1), (2) and (3)) is typically conducted sequentially in the same reaction vessel and without isolation or purification of the products until the overall reaction sequence is complete. Normally, Steps (1), (2) and (3) are all conducted in a suitable solvent Typically the same solvent is used throughout the reaction sequence. The solvent(s) should be inert under the conditions of the reaction steps. Suitable solvents include aromatic hydrocarbons such as chlorobenzene or toluene, and preferred solvents include esters such as ethyl acetate or butyl acetate; ketones such as acetone, 2-butanone, or 4-methyl-2-pentanone; ethers-such as tetrahydrofuran (THF) or dioxane; nitriles such as acetonitrile; and halocarbons such as dichloromethane or chloroform. More preferred solvents include acetonitrile, ethyl acetate, acetone, THF and dichloromethane. Most preferred are acetonitrile and acetone. The overall reaction sequence is typically conducted at temperatures ranging from −30° C. to +50° C. Preferred is the addition to the reaction vessel (charging) of all components at temperatures from −10° C. to +5° C., with reaction periods of from 1 to 60 minutes (preferred are reaction periods of from 5 to 15 minutes) between additions. Except where noted otherwise, the components can be added as mixtures, followed by warming to from +20° C. to +30° C. for 0.5 to 24 hours (preferably 2 to 4 hours). Charging of a component (for example, a reactant, a solvent, etc.) means adding the component during the step. One of ordinary skill in the art will recognize that a component may be added (i.e. charged) in various ways, for example as a batch, intermittent or continuous feed depending on process design. The manner in which a component is added and/or reacted can influence the actual mole ratio of that component to others over the duration of the step. However, the overall amount of a component added during a step is considered to be the amount charged, and is used herein for determining nominal mole ratios.

In Step (1) a carboxylic acid of Formula 2

   2 is contacted with a sulfonyl chloride of Formula 4

LS(O)₂Cl    4 in the presence of an optionally substituted pyridine compound of Formula 3. The nominal mole ratio (i.e. the ratio of reactants charged during Step (1)) of the Formula 4 compound to the Formula 2 compound is typically from about 1.0 to 1.5, and preferably is from about 1.1 to 1.3. Preferred Formula 4 compounds include methanesulfonyl chloride, propanesulfonyl chloride and benzenesulfonyl chloride. Methanesulfonyl chloride is more preferred for reasons of lower cost and/or less waste. The nominal mole ratio of the Formula 3 compound charged in Step (1) to the Formula 2 compound charged in Step (1) is typically from about 1.0 to 2.0, and is preferably from about 1.4 to 1.7. Preferred Formula 3 compounds include 2-picoline, 3-picoline, 2,6-lutidine, and pyridine. The compounds of Formulae 2, 3 and 4 may be combined in any order except that compound 2 cannot be added to the reaction mixture last. A preferred order of addition is to add a mixture of Formula 2 and Formula 3 in a solvent to a solution of Formula 4 in the same solvent.

In Step (2), the mixture prepared in (1) is contacted with an anthranilic acid of Formula 5

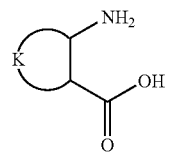   5 in the presence of an optionally substituted pyridine compound of Formula 3. Typically, the optionally substituted pyridine compound of Formula 3 in Step (2) is the same compound as that used in Step (1). The nominal mole ratio of the Formula 5 compound used in Step (2) to the Formula 2 compound charged in Step (1) is typically from about 0.9 to 1.1, and is preferably about 1.0. Normally, a second portion of Formula 3 compound is charged during Step (2); and the nominal mole ratio of the second portion of Formula 3 compound charged in Step (2) to the Formula 2 compound charged in Step (1) is typically from about 2.0 to 4.0, and preferably is from about 2.9 to 3.5. The compounds of Formulae 5 and 3 can be added to the mixture prepared in Step (1) in either order or as a mixture in solvent.

In Step (3) the mixture prepared in Step (2) is contacted with a sulfonyl chloride of Formula 4. Typically, the sulfonyl chloride in Step (3) is the same compound as that used in Step (1). The nominal mole ratio of the second portion of the Formula 4 compound charged in Step (3) to the Formula 2 compound charged in Step (1) is typically from about 1.0 to 1.5, and preferably is from about 1.1 to 1.3. Typically, Formula 4 is added to the mixture in the reaction solvent.

Preferred methods of this invention include the method wherein the carboxylic acid of Formula 2 is Formula 2', the ortho-amino carboxylic acid of Formula 5 is Formula 5' and the product compound of Formula 1 is Formula 1a

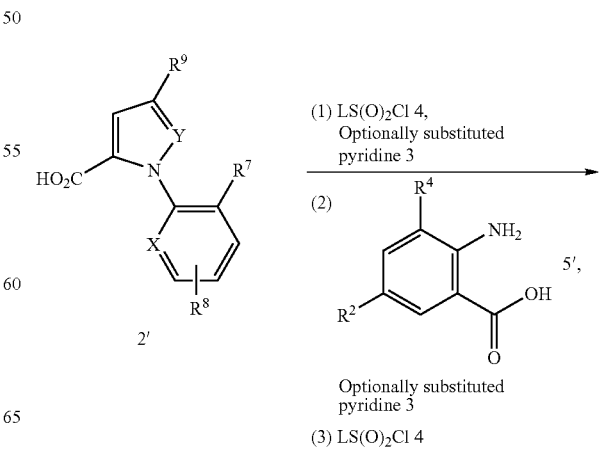

(1) LS(O)₂Cl 4,
Optionally substituted
pyridine 3

(2)

Optionally substituted
pyridine 3

(3) LS(O)₂Cl 4

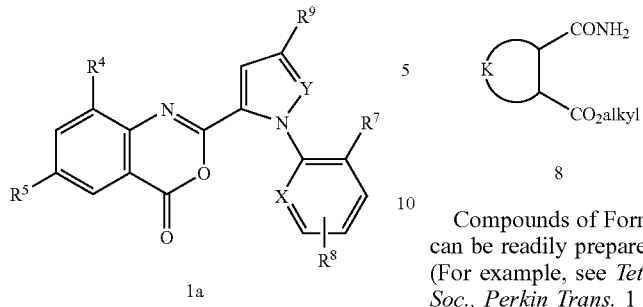

1a

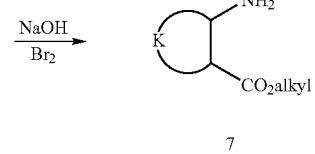

Scheme 3

8 → 7

Compounds of Formulae 6 and 8 are known in the art or can be readily prepared from compounds known in the art. (For example, see *Tetrahedron* 1997, 53, 14497; *J. Chem. Soc., Perkin Trans.* 1 1996, 10, 1035; PCT Patent Publication WO 92/08724 and European Patent Application EP 418667).

Carboxylic ester compounds of Formula 7 can be converted to the corresponding carboxylic acid compounds of Formula 5 by numerous methods including nucleophilic cleavage under anhydrous conditions or hydrolytic methods involving the use of either acids or bases (see T. W. Greene and P. G. M. Wuts, *Protective Groups in Organic Synthesis*, 2nd ed., John Wiley & Sons, Inc., New York, 1991, pp. 224-269 for a review of methods). In many cases, base-catalyzed hydrolytic methods are preferred. Suitable bases include alkali metal (such as lithium, sodium or potassium) hydroxides. For example, the ester can be dissolved in a mixture of water and an alcohol such as ethanol. Upon treatment with sodium hydroxide or potassium hydroxide, the ester is saponified to provide the sodium or potassium salt of the carboxylic acid. Acidification with a strong acid, such as hydrochloric acid or sulfuric acid, yields the carboxylic acid of Formula 5. The carboxylic acid can be isolated by methods known to those skilled in the art, including crystallization, extraction and distillation.

Anthranilic acids (or esters thereof) of Formula 5a (compounds of Formula 5 wherein K is a fused phenyl ring) are typically available from the corresponding 2-nitrobenzoic acids (or esters) of Formula 9 via catalytic hydrogenation of the nitro group (Scheme 4). Typical procedures involve reduction with hydrogen in the presence of a metal catalyst such as palladium on carbon or platinum oxide in hydroxylic solvents such as ethanol and isopropanol. They can also be prepared by reduction with zinc in acetic acid. These methods for reducing nitro groups are well documented in the chemical literature.

wherein

X is N or $CR^6$;

Y is N or CH;

$R^4$ is $C_1$-$C_4$ alkyl or halogen;

$R^5$ is H, $C_1$-$C_4$ alkyl, $C_1$-$C_4$ haloalkyl or halogen;

$R^6$ and $R^7$ are independently H, $C_1$-$C_4$ alkyl, $C_1$-$C_4$ haloalkyl, halogen, CN or $C_1$-$C_4$ haloalkoxy;

$R^8$ is H, $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, ($C_1$-$C_4$ alkyl)($C_3$-$C_6$ cycloalkyl)amino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl;

$R^9$ is $CF_3$, $OCF_3$, $OCHF_2$, $OCH_2CF_3$, $S(O)_pCF_3$, $S(O)_pCHF_2$ or halogen; and p is 0, 1 or 2.

Compounds of Formula 1a may be prepared in this way and used for preparing compounds of Formula III.

Esters of Formula 5 ortho-amino carboxylic acids (Formula 7) can be prepared from monoesters of ortho-dicarboxylic acids of Formula 6 via rearrangement of the corresponding acyl azide and hydrolysis of the resulting isocyanate (or alternatively by trapping of the isocyanate with an alcohol and cleaving of the resulting carbamate) as shown in Scheme 2.

Scheme 2

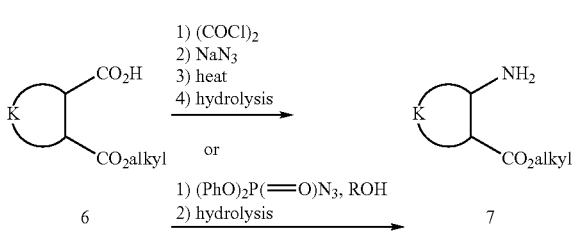

6 → 7

The conditions for cleaving the carbamate can hydrolyze the ester of Formula 7 to the carboxylic acid of Formula 5.

Alternatively ortho-amino carboxylic acid esters of Formula 7 can be prepared from ortho-carboxamide carboxylic esters of Formula 8 by Hoffmann rearrangement with reagents such as sodium hydroxide and bromine as shown in Scheme 3.

Scheme 4

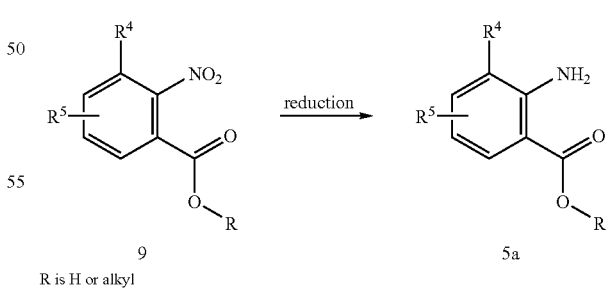

9 → 5a

R is H or alkyl

As shown in Scheme 5, anthranilic acids containing an $R^5$ substituent of chloro, bromo or iodo can be prepared by direct halogenation of an anthranilic acid of Formula 5b with N-chlorosuccinimide (NCS), N-bromosuccinimide (NBS) or N-iodosuccinimide (NIS) respectively in solvents such as NN-dimethylformamide (D)MF) to produce the corresponding substituted acid of Formula 5c.

Scheme 5

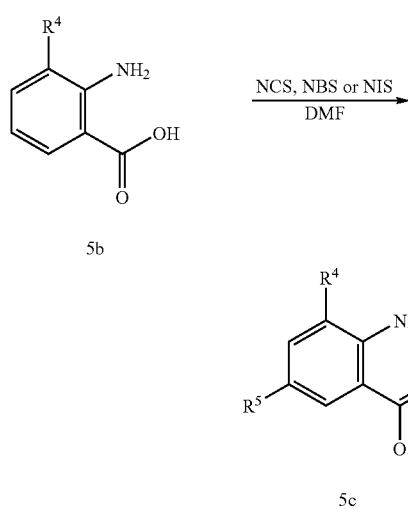

(R⁵ is Cl, Br or I)

Benzoic acids of Formula 2 (wherein J is optionally substituted phenyl) are generally well known in the art, as are procedures for their preparation.

Benzoic acids of Formula 2a may be prepared from the benzonitriles of Formula 10 by hydrolysis (Scheme 6). The conditions used may involve the use of a base such as an alkaline metal hydroxide or alkoxide (e.g., potassium or sodium hydroxide) in a solvent such as water, ethanol or ethylene glycol (see e.g., *J. Chem. Soc.* 1948, 1025). Alternatively, the hydrolysis may be carried out using an acid such as sulfuric acid or phosphoric acid in a suitable solvent such as water (see e.g., *Org. Synth.* 1955, Coll vol. 3, 557). The choice of the conditions is contingent on the stability of any optional substituents present on the aromatic ring to the reaction conditions and elevated temperatures are usually employed to achieve this transformation.

Scheme 6

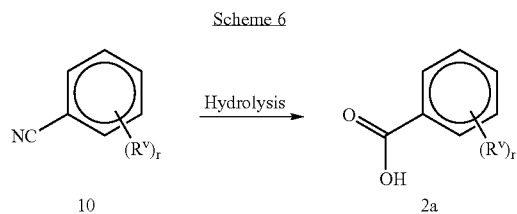

Nitriles of Formula 10 may be prepared from anilines of Formula 11 by the classical sequence involving diazotization and treatment of the intermediate diazonium salt with a copper cyanide salt (see e.g., *J. Amer. Chem. Soc.* 1902, 24, 1035).

Scheme 7

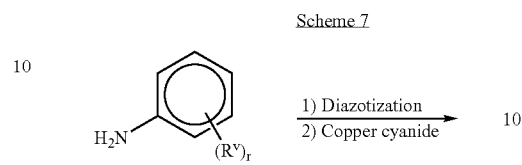

Certain heterocyclic acids of Formula 2, wherein J is an optionally substituted heterocycle, can be prepared by procedures outlined in Schemes 8 through 27. Both general and specific references to a wide variety of heterocyclic acids including thiophenes, furans, pyridines, pyrimidines, triazoles, imidazoles, pyrazoles, thiazoles, oxazoles, isothiazoles, thiadiazoles, oxadiazoles, triazines, pyrazines, pyridazines, and isoxazoles can be found in the following compendia: *Rodd's Chemistry of Chemistry of Carbon Compounds*, Vol. IVa to IVl., S. Coffey editor, Elsevier Scientific Publishing, New York, 1973; *Comprehensive Heterocyclic Chemistry*, Vol. 1-7, A. R. Katritzky and C. W. Rees editors, Pergamon Press, New York, 1984; *Comprehensive Heterocyclic Chemistry II*, Vol 1-9, A. R. Katritzky, C. W. Rees, and E. F. Scriven editors, Pergamon Press, New York, 1996; and the series, *The Chemistry of Heterocyclic Compounds*, E. C. Taylor, editor, Wiley, New York. Noteworthy heterocyclic acids suitable for use in this invention include pyridine acids, pyrimidine acids, pyrazole acids and pyrrole acids. Procedures for the synthesis of representative examples of each are detailed in Schemes 8 through 27. A variety of heterocyclic acids and general methods for their synthesis may be found in PCT Patent Publication WO 98/57397.

The synthesis of representative pyridine acids of Formula 2b is depicted in Scheme 8. This procedure involves the known synthesis of pyridines from β-ketoesters (Formula 16) and 4-aminobutenones (Formula 15). Substituent groups $R^a$ and $R^b$ include, for example, alky, haloalkyl, and optionally substituted aromatic and heteroaromatic rings.

Scheme 8

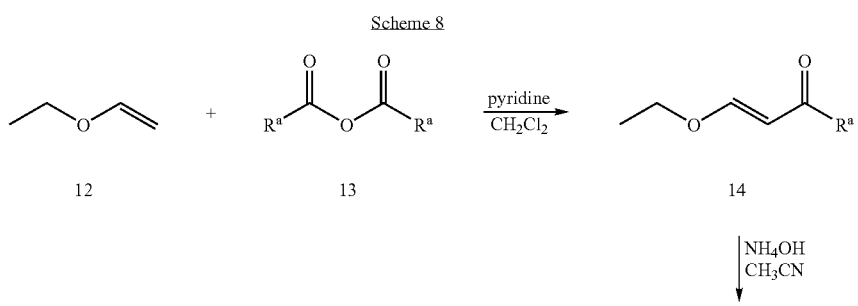

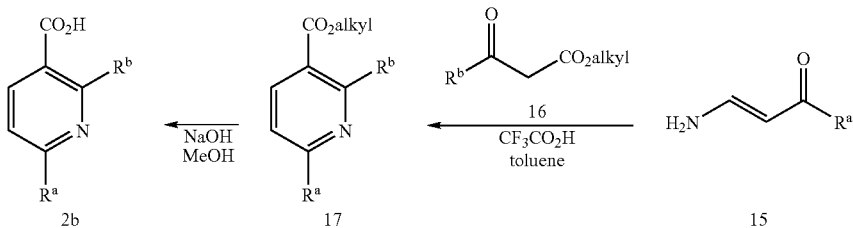

The synthesis of representative pyrimidine acids (Formula 2c) is depicted in Scheme 9. This procedure involves the known synthesis of pyrimidines from vinylidene-β-ketoesters (Formula 16) and amidines (Formula 20). Substituent groups $R^a$ and $R^b$ include, for example, alkyl, haloalkyl, and optionally substituted aromatic and heteroaromatic rings.

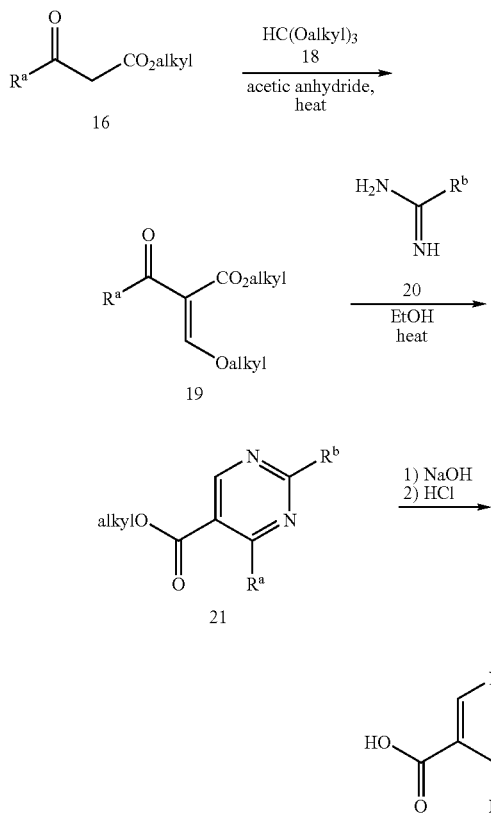

Syntheses of representative pyrazole acids (Formula 2d-2g) are depicted in Schemes 10 through 13. The synthesis of 2d in Scheme 10 involves as the key step introduction of the $R^a$ substituent via alkylation of the pyrazole. The alkylating agent $R^a$-Lg (wherein Lg is a leaving group such as Cl, Br, I, sulfonates such as p-toluenesulfonate, methanesulfonate or trifluoromethanesulfonate, or sulfates such as —$SO_2OR^a$) includes $R^a$ groups such as $C_1$-$C_6$ alkyl, $C_2$-$C_6$ alkenyl, $C_2$-$C_6$ alkyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, $C_2$-$C_6$ alkylcarbonyl, $C_2$-$C_6$ alkoxycarbonyl, $C_3$-$C_8$ dialkylamino-carbonyl, $C_3$-$C_6$ trialkylsilyl; or phenyl, benzyl, benzoyl, 5- or 6-membered heteroaromatic rings or aromatic 8-, 9- or 10-membered fused heterobicyclic ring systems, each ring or ring system optionally substituted. (As referred to herein, the terms "alkylation" and "alkylating agent" are not limited to $R^a$ being an alkyl group.) Oxidation of the methyl group affords the pyrazole carboxylic acid. Some notable $R^b$ groups include haloalkyl.

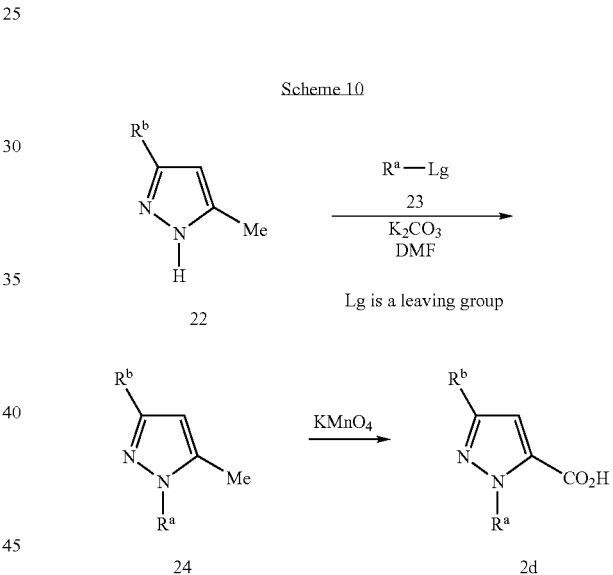

Alkylation of pyrazoles using potassium carbonate and NN-dimethylformamide (DMF) are described by T. Kitazaki et al., *Chem. Pharm. Bull.* 2000, 48(12), 1935-1946. One skilled in the art recognizes that a variety of bases and solvents can be used for alkylation of pyrazoles. For example, C. T. Alabaster et al., *J. Med. Chem.* 1989, 32, 575-583 discloses use of sodium carbonate in DMF, X. Wang et al., *Org. Lett.* 2000, 2(20), 3107-3109 discloses use of potassium tert-butoxide in methyl sulfoxide, and European Patent Application Publication EP-1081146-A1 describes the use of methyl sulfoxide and sodium or potassium hydroxide in the presence of a phase transfer catalyst or cesium carbonate. One skilled in the art also recognizes that a variety of alternative synthetic methods are applicable to the coupling of a pyrazole of Formula 22 to form a pyrazole of Formula 24 (or coupling of a pyrazole of Formula 25 below to form a pyrazole of Formula 26 below). These methods include, for example, condensation with aryl iodides in the presence of copper(I) iodide and trans-cyclohexanediamine as reported by A. Klapars, J. C. Antilla, X. Huang and S. L. Buchwald, *J. Am. Chem. Soc.* 2001, 123, 7727-7729, and condensation with aryl boronic acids in the presence of copper(II) acetate and pyridine as reported by P. Y. S. Lam, C. G. Clark, S. Saubern, J. Adams, M. P. Winters, D. M. T. Chan and A. Combs, *Tetrahedron Lett.* 1998, 39, 2941-2944.

Some pyrazole acids of Formula 2d may be prepared via metallation and carboxylation of pyrazoles of Formula 26 as the key step (Scheme 11). This reaction is typically conducted by treating compounds of Formula 25 with lithium diisopropylamide (LDA) to form an anion and then contacting the anion with carbon dioxide. The $R^a$ group is introduced in a manner similar to that of Scheme 10, i.e. via alkylation with an $R^a$ alkylating agent Representative $R^b$ groups include, for example, cyano and haloalkyl.

Scheme 11

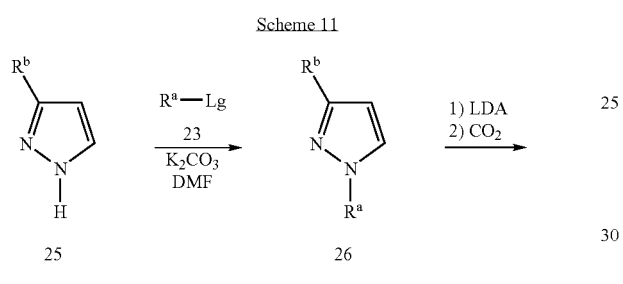

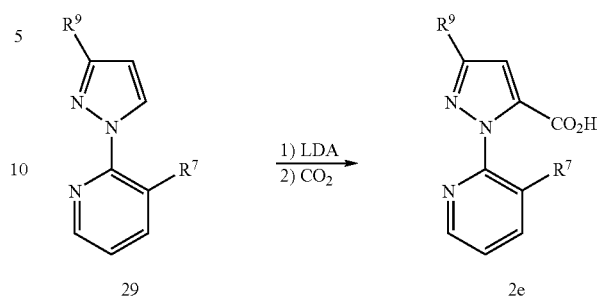

wherein $R^7$ is H, $C_1$-$C_4$ alkyl, $C_1$-$C_4$ haloalkyl, halogen, CN or $C_1$-$C_4$ haloalkoxy; and $R^9$ is $CF_3$, $OCF_3$, $OCHF_2$, $OCH_2CF_3$, $S(O)_pCF_3$, $S(O)_pCHF_2$ or halogen This method is illustrated by Example 1, Steps D and E.

Other pyrazoles of Formula 2d can be prepared via reaction of hydrazine of Formula 31 with a pyruvate of Formula 30 to yield pyrazole esters of Formula 32 (Scheme 13). Hydrolysis of the ester affords the pyrazole acids 2d. This procedure is particularly useful for the preparation of compounds wherein $R^a$ is optionally substituted phenyl and $R^b$ is haloalkyl.

Scheme 13

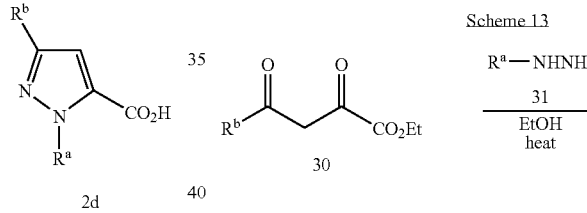

This procedure is particularly useful for preparing 1-(2-pyridinyl)pyrazolecarboxylic acids of Formula 2e, wherein $R^a$ is a substituted 2-pyridinyl ring, as shown in Scheme 12. Reaction of a pyrazole of Formula 27 with a 2-halopyridine of Formula 28 affords good yields of the 1-pyridinylpyrazole of Formula 29 with good specificity for the desired regiochemistry. Metallation of 29 with LDA followed by quenching of the lithium salt with carbon dioxide affords the 1-(2-pyridinyl)pyrazolecarboxylic acid of Formula 2e.

Pyrazole acids of Formula 2d can also be prepared via 3+2 cycloaddition of an appropriately substituted nitrilimine of Formula 33 with either substituted propiolates of Formula 34 or acrylates of Formula 35 (Scheme 14). Cycloaddition with acrylates requires additional oxidation of the intermediate pyrazoline to the pyrazole. Hydrolysis of the ester of Formula 36 affords the pyrazole acids 2d. Preferred iminohalides for this reaction include the tifluoromethyl iminochloride (37) and the iminodibronide (38). Compounds such as 37 are known (*J. Heterocycl. Chem.* 1985, 22(2), 565-8). Compounds such as 38 are available by known methods (*Tetrahedron Letters* 1999, 40, 2605). These procedures are particularly useful for the preparation of compounds where $R^a$ is optionally substituted phenyl and $R^b$ is haloalkyl or bromo.

Scheme 12

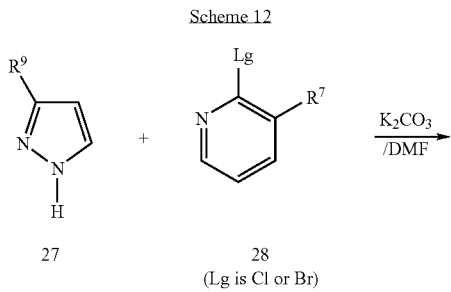

(Lg is Cl or Br)

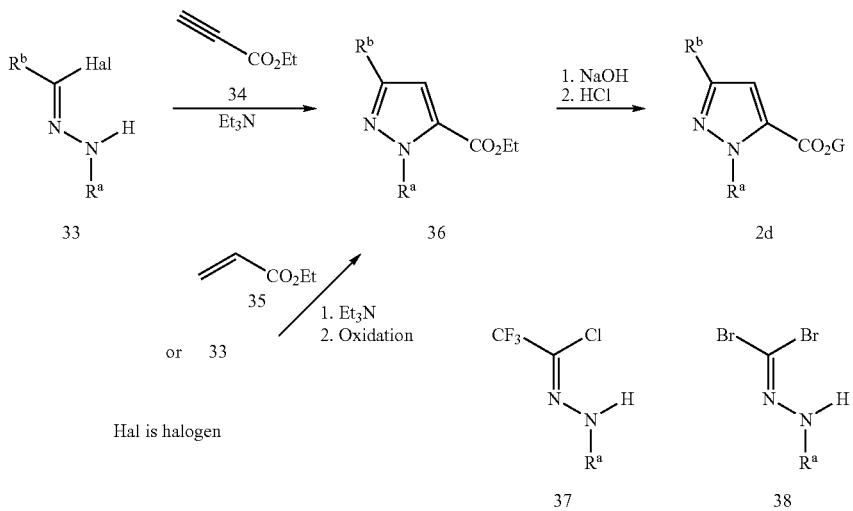

The starting pyrazoles of Formula 25 are known compounds or can be prepared according to known methods. The pyrazole of Formula 25a (the compound of Formula 25 wherein $R^b$ is $CF_3$) can be prepared by literature procedures (*J. Fluorine Chem.* 1991, 53(1), 61-70). The pyrazoles of Formula 25b (compounds of Formula 25 wherein $R^b$ is Cl or Br) can be prepared by literature procedures (*Chem. Ber.* 1966, 99(10), 3350-7). A useful alternative method for the preparation of a compound of Formula 25b is depicted in Scheme 15. Metallation of the sulfamoyl pyrazole of Formula 39 with n-butyllithium followed by direct halogenation of the anion with either hexachloroethane (for $R^b$ being Cl) or 1,2-dibromotetrachloroethane (for $R^b$ being Br) affords the halogenated derivatives of Formula 40. Removal of the sulfamoyl group with trifluoroacetic acid (TFA) at room temperature proceeds cleanly and in good yield to afford the pyrazoles of Formula 25c. One skilled in the art will recognize that Formula 25c is a tautomer of Formula 25b.

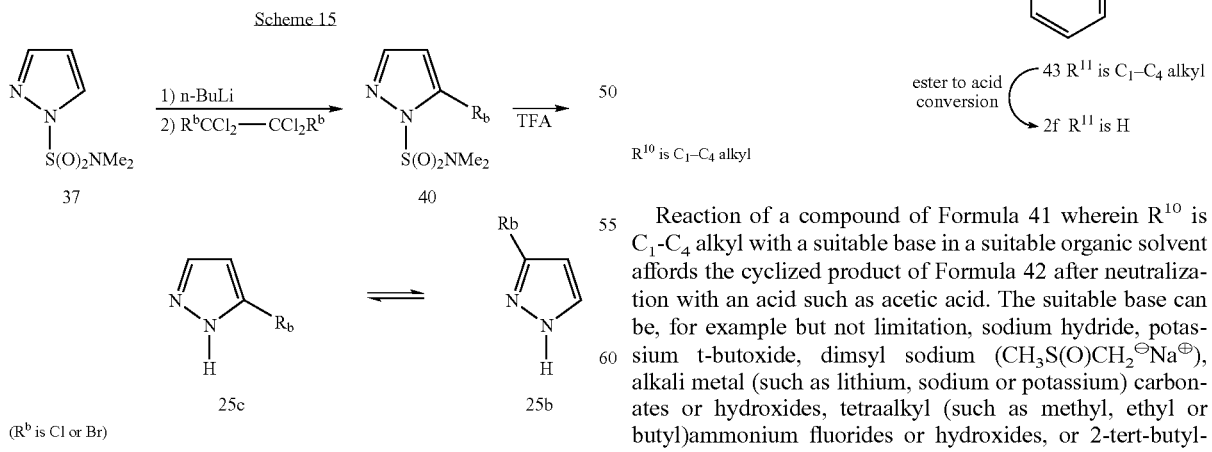

Pyrazolecarboxylic acids of Formula 2f wherein $R^{10}$ is $CF_3$ can be prepared by the method outlined in Scheme 16.

Reaction of a compound of Formula 41 wherein $R^{10}$ is $C_1$-$C_4$ alkyl with a suitable base in a suitable organic solvent affords the cyclized product of Formula 42 after neutralization with an acid such as acetic acid. The suitable base can be, for example but not limitation, sodium hydride, potassium t-butoxide, dimsyl sodium ($CH_3S(O)CH_2^\ominus Na^\oplus$), alkali metal (such as lithium, sodium or potassium) carbonates or hydroxides, tetraalkyl (such as methyl, ethyl or butyl)ammonium fluorides or hydroxides, or 2-tert-butyl-imino-2-diethylamino-1,3-dimethyl-perhydro-1,3,2-diaza-phosphonine. The suitable organic solvent can be, for example but not limitation, acetone, acetonitrile, tetrahydrofuran, dichloromethane, dimethylsulfoxide, or N,N-dimethylformamide. The cyclization reaction is usually conducted in a temperature range from about 0 to 120° C. The effects of solvent, base, temperature and addition time are all interdependent, and choice of reaction conditions is important to minimize the formation of byproducts. A preferred base is tetrabutyl-ammonium fluoride.

Dehydration of the compound of Formula 42 to give the compound of Formula 43, followed by converting the carboxylic ester function to carboxylic acid, affords the compound of Formula 2f. The dehydration is effected by treatment with a catalytic amount of a suitable acid. This catalytic acid can be, for example but not limitation, sulfuric acid. The reaction is generally conducted using an organic solvent. As one skilled in the art will realize, dehydration reactions may be conducted in a wide variety of solvents in a temperature range generally between about 0 and 200° C., more preferably between about 0 and 100° C. For the dehydration in the method of Scheme 16, a solvent comprising acetic acid and temperatures of about 65° C. are preferred Carboxylic ester compounds can be converted to carboxylic acid compounds by numerous methods including nucleophilic cleavage under anhydrous conditions or hydrolytic methods involving the use of either acids or bases (see T. W. Greene and P. G. M. Wuts, *Protective Groups in Organic Synthesis*, 2nd ed., John Wiley & Sons, Inc., New York, 1991, pp. 224-269 for a review of methods). For the method of Scheme 16, base-catalyzed hydrolytic methods are preferred. Suitable bases include alkali metal (such as lithium, sodium or potassium) hydroxides. For example, the ester can be dissolved in a mixture of water and an alcohol such as ethanol. Upon treatment with sodium hydroxide or potassium hydroxide, the ester is saponified to provide the sodium or potassium salt of the carboxylic acid. Acidification with a strong acid, such as hydrochloric acid or sulfuric acid, yields the carboxylic acid of Formula 2f. The carboxylic acid can be isolated by methods known to those skilled in the art, including crystallization, extraction and distillation.

Compounds of Formula 41 can be prepared by the method outlined in Scheme 17.

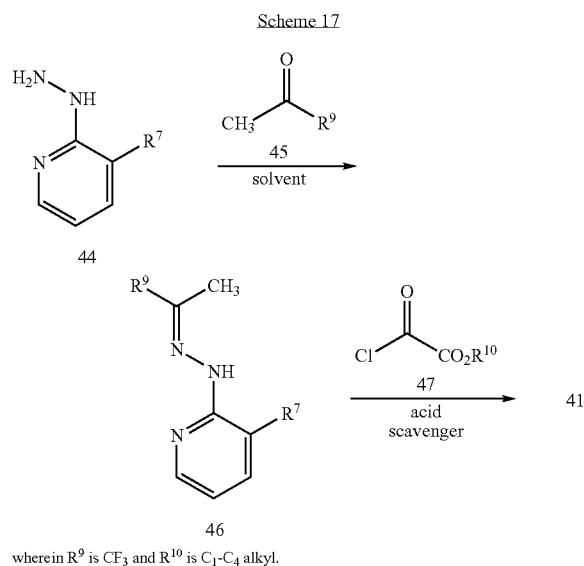

wherein $R^9$ is $CF_3$ and $R^{10}$ is $C_1$-$C_4$ alkyl.

Treatment of a hydrazine compound of Formula 44 with a ketone of Formula 45 in a solvent such as water, methanol or acetic acid gives the hydrazone of Formula 46. One skilled in the art will recognize that this reaction may require catalysis by an optional acid and may also require elevated temperatures depending on the molecular substitution pattern of the hydrazone of Formula 46. Reaction of the hydrazone of Formula 46 with the compound of Formula 47 in a suitable organic solvent such as, for example but not limitation, dichloromethane or tetrahydrofuran in the presence of an acid scavenger such as triethylamine provides the compound of Formula 41. The reaction is usually conducted at a temperature between about 0 and 100° C. Hydrazine compounds of Formula 44 can be prepared by standard methods, such as by contacting the corresponding halo compound of Formula 28 (Scheme 12) with hydrazine.

Pyrazolecarboxylic acids of Formula 2g wherein $R^9$ is halogen such as Cl or Br can be prepared by the method outlined in Scheme 18.

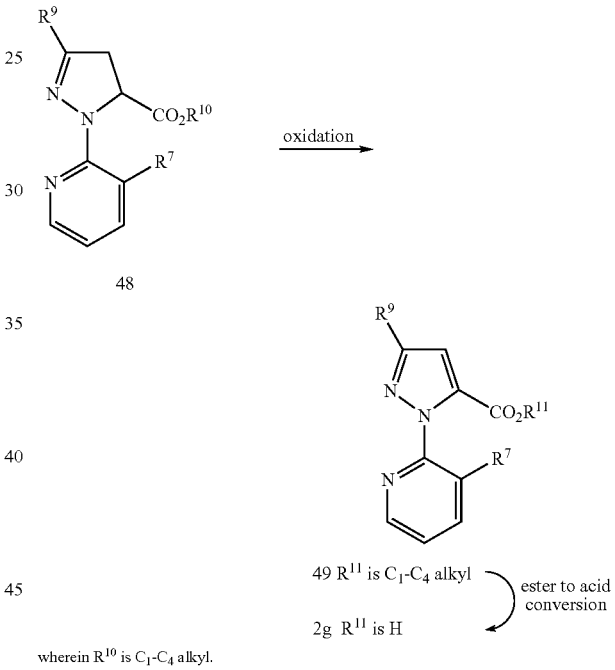

wherein $R^{10}$ is $C_1$-$C_4$ alkyl.

Oxidation of the compound of Formula 48 optionally in the presence of acid to give the compound of Formula 49 followed by conversion of the carboxylic ester function to the carboxylic acid provides the compound of Formula 2g. The oxidizing agent can be hydrogen peroxide, organic peroxides, potassium persulfate, sodium persulfate, ammonium persulfate, potassium monopersulfate (e.g., Oxone®) or potassium permanganate. To obtain complete conversion, at least one equivalent of oxidizing agent versus the compound of Formula 48 should be used, preferably between about one to two equivalents. This oxidation is typically carried out in the presence of a solvent. The solvent can be an ether, such as tetrahydrofuran, p-dioxane and the like, an organic ester, such as ethyl acetate, dimethyl carbonate and the like, or a polar aprotic organic such as N,N-dimethylformamide, acetonitrile and the like. Acids suitable for use in the oxidation step include inorganic acids, such as sulfuric acid, phosphoric acid and the like, and organic acids, such as acetic acid, benzoic acid and the like. The acid, when used, should be used in greater than 0.1 equivalents versus the compound of Formula 48. To obtain complete conversion, one to five equivalents of acid can be used. The preferred oxidant is potassium persulfate, and the oxidation is preferably carried out in the presence of sulfuric acid. The reaction can be carried out by mixing the compound of Formula 48 in the desired solvent and, if used, the acid. The oxidant can then be added at a convenient rate. The reaction temperature is typically varied from as low as about 0° C. up to the boiling point of the solvent in order to obtain a reasonable reaction time to complete the reaction, preferably less than 8 hours. The desired product, a compound of Formula 49, can be isolated by methods known to those skilled in the art, including crystallization, extraction and distillation. Methods suitable for converting the ester of Formula 49 to the carboxylic acid of Formula 2g are already described for Scheme 16.

Compounds of Formula 48 wherein $R^9$ is halogen such as Cl or Br can be prepared from corresponding compounds of Formula 50 as shown in Scheme 19.

Scheme 19

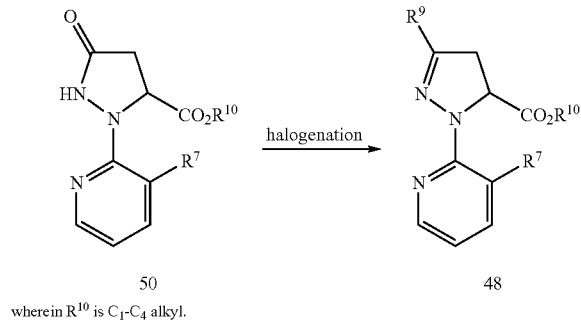

wherein $R^{10}$ is $C_1$-$C_4$ alkyl.

Treatment of a compound of Formula 50 with a halogenating reagent, usually in the presence of a solvent, affords the corresponding halo compound of Formula 48 ($R^9$ is halogen). Halogenating reagents that can be used include phosphorus oxyhalides, phosphorus trihalides, phosphorus pentahalides, thionyl chloride, dihalotrialkylphophoranes, dihaldtriphenylphosphoranes, oxalyl chloride and phosgene. Preferred are phosphorus oxyhalides and phosphorus pentahalides. To obtain complete conversion, at least 0.33 equivalents of phosphorus oxyhalide versus the compound of Formula 50 should be used (i.e. the mole ratio of phosphorus oxyhalide to the compound of Formula 50 is 0.33), preferably between about 0.33 and 1.2 equivalents. To obtain complete conversion, at least 0.20 equivalents of phosphorus pentahalide versus the compound of Formula 50 should be used, preferably between about 0.20 and 1.0 equivalents. Compounds of Formula 50 wherein $R^{10}$ is $C_1$-$C_4$ alkyl are preferred for this reaction. Typical solvents for this halogenation include halogenated alkanes, such as dichloromethane, chloroform, chlorobutane and the like, aromatic solvents, such as benzene, xylene, chlorobenzene and the like, ethers, such as tetrahydrofuran, p-dioxane, diethyl ether, and the like, and polar aprotic solvents such as acetonitrile, N,N-dimethylformamide, and the like. Optionally, an organic base, such as triethylamine, pyridine, N,N-dimethylaniline or the like, can be added. Addition of a catalyst, such as NN-dimethylformamide, is also an option.

Preferred is the process in which the solvent is acetonitrile and a base is absent. Typically, neither a base nor a catalyst is required when acetonitrile solvent is used. The preferred process is conducted by mixing the compound of Formula 50 in acetonitrile. The halogenating reagent is then added over a convenient time, and the mixture is then held at the desired temperature until the reaction is complete. The reaction temperature is typically between 20° C. and the boiling point of acetonitrile, and the reaction time is typically less than 2 hours. The reaction mass is then neutralized with an inorganic base, such as sodium bicarbonate, sodium hydroxide and the like, or an organic base, such as sodium acetate. The desired product, a compound of Formula 48, can be isolated by methods known to those skilled in the art, including crystallization, extraction and distillation.

Alternatively, compounds of Formula 48 wherein $R^9$ is halogen such as Br or Cl can be prepared by treating the corresponding compounds of Formula 48 wherein $R^9$ is a different halogen (e.g., Cl for making Formula 48 wherein $R^9$ is Br) or a sulfonate group such as methanesulfonate, benzenesulfonate or p-toluenesulfonate with hydrogen bromide or hydrogen chloride, respectively. By this method the $R^9$ halogen or sulfonate substituent on the Formula 48 starting compound is replaced with Br or Cl from hydrogen bromide or hydrogen chloride, respectively. The reaction is conducted in a suitable solvent such as dibromomethane, dichloromethane, acetic acid, ethyl acetate or acetonitrile. The reaction can be conducted at or near atmospheric pressure or above atmospheric pressure in a pressure vessel. The hydrogen halide starting material can be added in the form of a gas to the reaction mixture containing the Formula 48 starting compound and solvent. When $R^9$ in the starting compound of Formula 48 is a halogen such as Cl, the reaction is preferably conducted in such a way that the hydrogen halide generated from the reaction is removed by sparging or other suitable means. Alternatively, the hydrogen halide starting material can be first dissolved in an inert solvent in which it is highly soluble (such as acetic acid) before contacting with the starting compound of Formula 48 either neat or in solution. Also when $R^9$ in the starting compound of Formula 48 is a halogen such as Cl, substantially more than one equivalent of hydrogen halide starting material (e.g., 4 to 10 equivalents) is typically needed depending upon the level of conversion desired. One equivalent of hydrogen halide starting material can provide high conversion when $R^9$ in the starting compound of Formula 48 is a sulfonate group, but when the starting compound of Formula 48 comprises at least one basic function (e.g., a nitrogen-containing heterocycle), more than one equivalent of hydrogen halide starting material is typically needed. The reaction can be conducted between about 0 and 100° C., most conveniently near ambient temperature (e.g., about 10 to 40° C.), and more preferably between about 20 and 30° C. Addition of a Lewis acid catalyst (such as aluminum tribromide for preparing Formula 48 wherein $R^9$ is Br) can facilitate the reaction. The product of Formula 48 is isolated by the usual methods known to those skilled in the art, including extraction, distillation and crystallization.

Starting compounds of Formula 48 wherein $R^9$ is Cl or Br can be prepared from corresponding compounds of Formula 50 as already described. Starting compounds of Formula 48 wherein $R^9$ is a sulfonate group can likewise be prepared from corresponding compounds of Formula 50 by standard methods such as treatment with a sulfonyl chloride (e.g., methanesulfonyl chloride, benzenesulfonyl chloride or p-toluenesulfonyl chloride) and base such as a tertiary amine (e.g., triethylamine) in a suitable solvent such as dichloromethane.

Pyrazolecarboxylic acids of Formula 2h wherein $R^9$ is $OCH_2CF_3$ or Formula 2i wherein $R^9$ is $OCHF_2$ can be prepared by the method outlined in Scheme 20. In this method, instead of being halogenated as shown in Scheme 19, the compound of Formula 50 is oxidized to the compound of Formula 51. The reaction conditions for this oxidation are as already described for the conversion of the compound of Formula 48 to the compound of Formula 49 in Scheme 18.

The compound of Formula 51 is then alkylated to form the compound of Formula 54 ($R^9$ is $OCH_2CF_3$) by contact with an alkylating agent $CF_3CH_2Lg$ (52) in the presence of a base. In the alkylating agent 52, Lg is a nucleophilic reaction leaving group such as halogen (e.g., Br, I), $OS(O)_2CH_3$ (methanesulfonate), $OS(O)_2CF_3$, $OS(O)_2Ph$-p-$CH_3$ (p-toluenesulfonate), and the like; methanesulfonate works well. The reaction is conducted in the presence of at least one equivalent of a base. Suitable bases include inorganic bases, such as alkali metal (such as lithium, sodium or potassium) carbonates and hydroxides, and organic bases, such as triethylamine, diisopropylethylamine and 1,8-diazabicyclo[5.4.0]undec-7-ene. The reaction is generally conducted in a solvent, which can comprise alcohols, such as methanol and ethanol, halogenated alkanes, such as dichloromethane, aromatic solvents, such as benzene, toluene and chlorobenzene, ethers, such as tetrahydrofuran, and polar aprotic solvents, such as acetonitrile, N,N-dimethylformamide, and the like. Alcohols and polar aprotic solvents are preferred for use with inorganic bases. Potassium carbonate as base and acetonitrile as solvent are preferred. The reaction is typically conducted between about 0 and 150° C., and more typically between ambient temperature and 100° C.

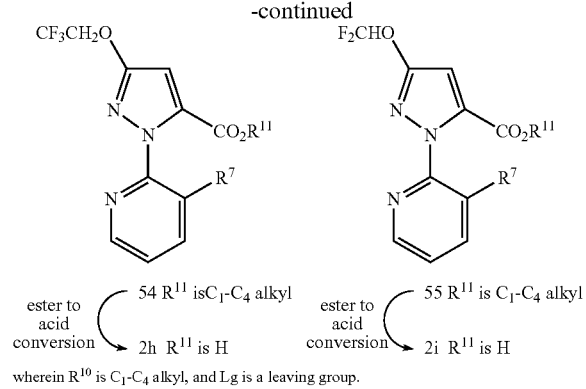

wherein $R^{10}$ is $C_1$-$C_4$ alkyl, and Lg is a leaving group.

The compound of Formula 51 can also be alkylated to form the compound of Formula 55 ($R^9$ is $OCHF_2$) by contact with difluorocarbene, prepared from $CHClF_2$ (53) in the presence of a base. The reaction is generally conducted in a solvent, which can comprise ethers, such as tetrahydrofuran or dioxane, and polar aprotic solvents, such as acetonitrile, N,N-dimethylformamide, and the like. The base can be selected from inorganic bases such as potassium carbonate, sodium hydroxide or sodium hydride. Preferably the reaction is conducted using potassium carbonate with NN-dimethylformamide as the solvent. The product of Formula 54 or 55 can be isolated by conventional techniques such as extraction. The esters can then be converted to the carboxylic acids of Formula 2h or 2i by the methods already described for the conversion of Formula 43 to Formula 2f in Scheme 16.

Compounds of Formula 50 can be prepared from compounds of Formula 44 (see Scheme 17) as outlined in Scheme 21.

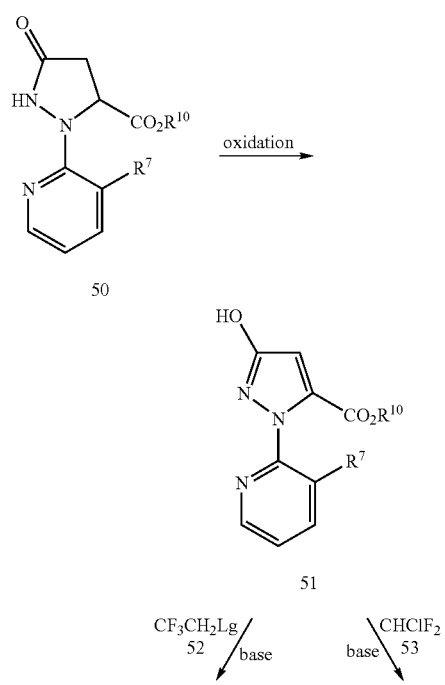

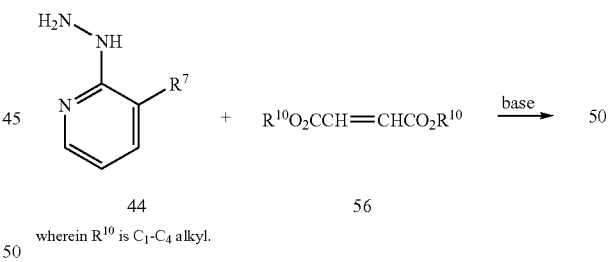

wherein $R^{10}$ is $C_1$-$C_4$ alkyl.

In this method, a hydrazine compound of Formula 44 is contacted with a compound of Formula 56 (a fumarate ester or maleate ester or a mixture thereof may be used) in the presence of a base and a solvent. The base is typically a metal alkoxide salt, such as sodium methoxide, potassium methoxide, sodium ethoxide, potassium ethoxide, potassium tert-butoxide, lithium tert-butoxide, and the like. Greater than 0.5 equivalents of base versus the compound of Formula 56 should be used, preferably between 0.9 and 1.3 equivalents. Greater than 1.0 equivalents of the compound of Formula 44 should be used, preferably between 1.0 to 1.3 equivalents. Polar protic and polar aprotic organic solvents can be used, such as alcohols, acetonitrile, tetrahydrofuran, N,N-diethylformamide, dimethyl sulfoxide and the like. Preferred solvents are alcohols such as methanol and ethanol. It is especially preferred that the alcohol be the same as that making up the fumarate or maleate ester and the alkoxide base. The reaction is typically conducted by mixing the compound of Formula 56 and the base in the solvent. The mixture can be heated or cooled to a desired temperature and the compound of Formula 44 added over a period of time. Typically reaction temperatures are between 0° C. and the boiling point of the solvent used. The reaction may be conducted under greater than atmospheric pressure in order to increase the boiling point of the solvent. Temperatures between about 30 and 90° C. are typically preferred. The addition time can be as quick as heat transfer allows. Typical addition times are between 1 minute and 2 hours. Optimum reaction temperature and addition time vary depending upon the identities of the compounds of Formula 44 and Formula 56. After addition, the reaction mixture can be held for a time at the reaction temperature. Depending upon the reaction temperature, the required hold time may be from 0 to 2 hours. Typical hold times are 10 to 60 minutes. The reaction mass then can be acidified by adding an organic acid, such as acetic acid and the like, or an inorganic acid, such as hydrochloric acid, sulfuric acid and the like. Depending on the reaction conditions and the means of isolation, the —$CO_2R^{10}$ function on the compound of Formula 50 may be hydrolyzed to —$CO_2H$; for example, the presence of water in the reaction mixture can promote such hydrolysis. If the carboxylic acid (—$CO_2H$) is formed, it can be converted back to —$CO_2R^{10}$ wherein $R^{10}$ is $C_1$-$C_4$ alkyl using esterification methods well known in the art. The desired product, a compound of Formula 50, can be isolated by methods known to those skilled in the art, such as crystallization, extraction or distillation.

The synthesis of representative pyrazole acids of Formula 2j is depicted in Scheme 22. Reaction of a dimethylaminoylidene ketoester of Formula 58 with substituted hydrazines of Formula 31 affords the pyrazoles of Formula 59. Notable $R^a$ substituents include alkyl and haloalkyl, with 2,2,2-trifluoroethyl especially noteworthy. The esters of Formula 59 are converted to the acids of Formula 2j by standard hydrolysis methods.

The synthesis of pyrazole acids of Formula 2k, wherein $R^b$ is a substituted 2-pyridyl moiety attached to the 5-position of the pyrazole ring, is depicted in Scheme 23. This synthesis is conducted according to the general synthesis described in Scheme 22.

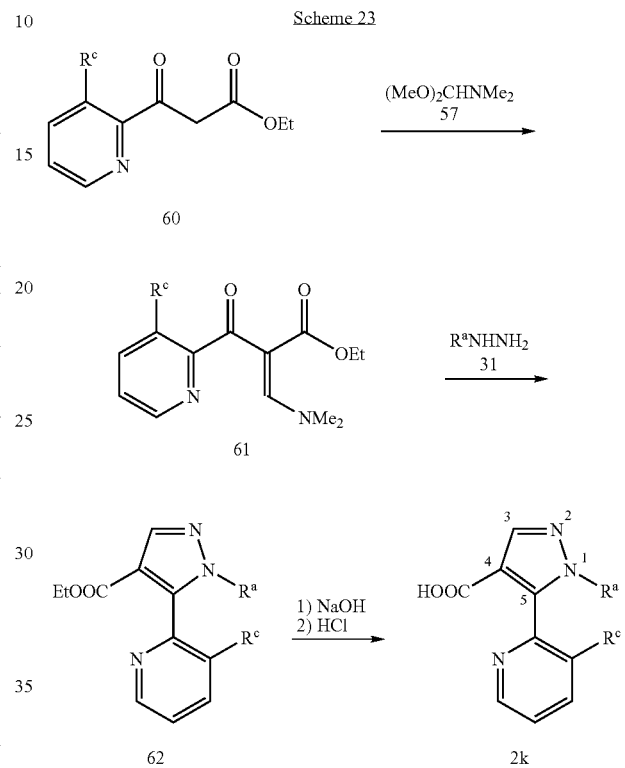

The synthesis of representative pyrazole acids of Formula 2m, as well as an alternative synthesis of Formula 2j, is depicted in Scheme 24. Reaction of the dimethylaminoylidene ketoester of Formula 58 with hydrazine affords the pyrazole of Formula 63. Reaction of the pyrazole 63 with alkylating agents of Formula 23 ($R^a$-Lg wherein Lg is a leaving group such as halogen (e.g., Br, I), $OS(O)_2CH_3$ (methanesulfonate), $OS(O)_2CF_3$, $OS(O)_2Ph$-p-$CH_3$ (p-toluenesulfonate), and the like) affords a mixture of pyrazoles of Formulae 64 and 65. This mixture of pyrazole isomers is readily separated by chromatographic methods and converted to the corresponding acids 2m and 2j. Noteworthy $R^a$ substituents include alkyl and haloalkyl groups.

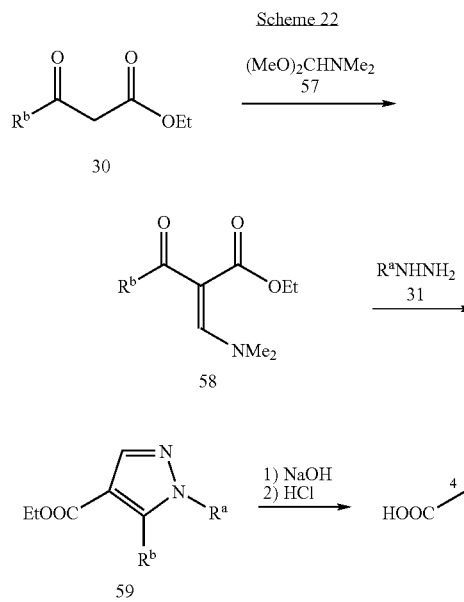

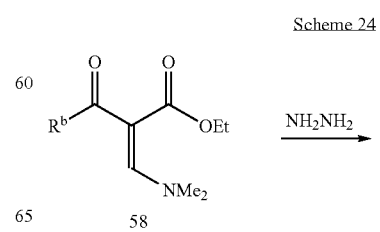

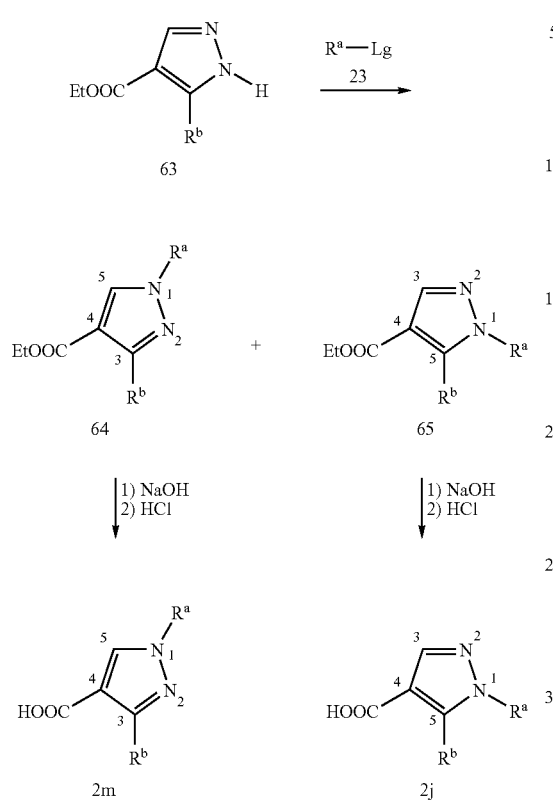

Of note is the synthesis of pyridinylpyrazole acids of Formula 2n, wherein $R^b$ is a substituted 2-pyridinyl and attached to the 3-position of the pyrazole ring, as well as an alternative synthesis of Formula 2k, is depicted in Scheme 25. This synthesis is conducted according to the general synthesis described in Scheme 24.

A general synthesis of pyrrole acids of Formula 20 is depicted in Scheme 26. Treatment of a compound of Formula 69 with 2,5-dimethoxytetrahydrofuran (70) affords a pyrrole of Formula 71. Formylation of the pyrrole 71 to provide the aldehyde of Formula 72 can be accomplished by using standard Vilsmeier-Haack formulation conditions, such as N,N-dimethylformamide (DMF) and phosphorus oxychloride. Halogenation of the compound of Formula 72 with N-halosuccinimides (NXS) such as N-chlorosuccinimide or N-bromosuccinimide occurs preferentially at the 4-position of the pyrrole ring. Oxidation of the halogenated aldehyde affords the pyrrole acid of Formula 2o. The oxidation can be accomplished by using a variety of standard oxidation conditions.

Scheme 25

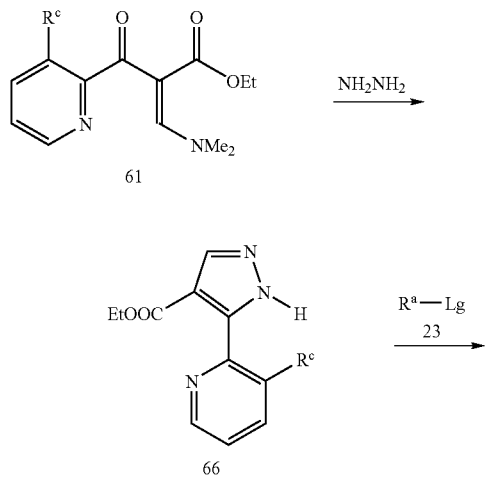

Scheme 26

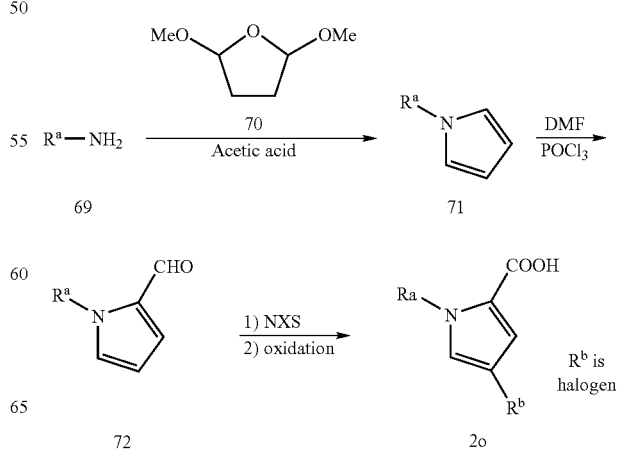

The synthesis of certain pyridinylpyrrole acids of Formula 2p is depicted in Scheme 27. The compound of Formula 74, 3-chloro-2-aminopyridine, is a known compound (see *J. Heterocycl. Chem.* 1987, 24(5), 1313-16). A convenient preparation of 74 from the 2-aminopyridine of Formula 73 involves protection, ortho-metallation, chlorination and subsequent deprotection. The remaining synthesis is conducted according to the general synthesis described in Scheme 26.

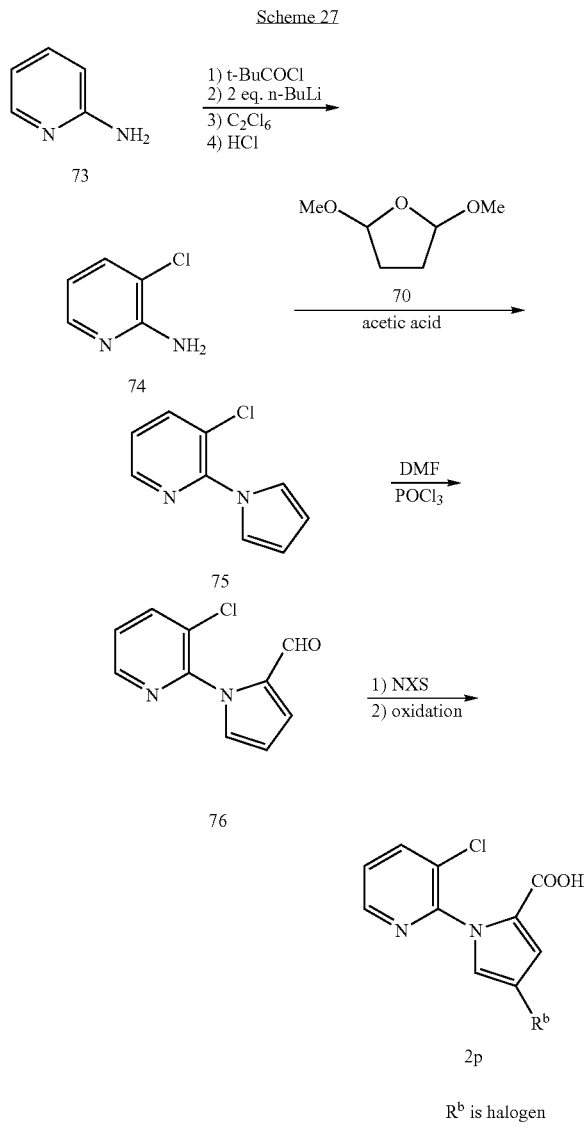

Scheme 27

R$^b$ is halogen

It is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, 't' means triplet, "q" means quartet, "m" means multiplet, "dd" means doublet of doublets, "dt" means doublet of triplets, and "br s" means broad singlet.

EXAMPLE 1

Preparation of 2-[3-bromo-1-(3-chloro-2-pyridinyl)-1H-pyrazol-5-yl]-6-chloro-8-methyl-4H-3,1-benzoxazin-4-one Step A: Preparation of 2-amino-3-methyl-5-chlorobenzoic acid To a solution of 2-amino-3-methylbenzoic acid (Aldrich, 15.0 g, 99.2 mmol) in N,N-dimethylformamide (50 mL) was added N-chlorosuccinimide (13.3 g, 99.2 mmol) and the reaction mixture was heated to 100° C. for 30 minutes. The heat was removed and the reaction mixture was cooled to room temperature and allowed to stand overnight. The reaction mixture was then slowly poured into ice water (250 mL) to precipitate a white solid. The solid was filtered and washed four times with water and then taken up in ethyl acetate (900 mL). The ethyl acetate solution was dried over magnesium sulfate, evaporated under reduced pressure and the residual solid was washed with ether to afford the desired intermediate as a white solid (13.9 g).
$^1$H NMR (DMSO-d$_6$) δ 2.11 (s, 3H), 7.22 (s, 1H), 7.55 (s, 1H).

Step B: Preparation of 3-bromo-N,N-dimethyl-1H-pyrazole-1-sulfonamide

To a solution of N-dimethylsulfamoylpyrazole (44.0 g, 0.251 mol) in dry tetrahydrofuran (500 mL) at −78° C. was added dropwise a solution of n-butyllithium (2.5 M in hexane, 105.5 mL, 0.264 mol) while maintaining the temperature below −60° C. A thick solid formed during the addition. Upon completion of the addition the reaction mixture was maintained for an additional 15 minutes, after which time a solution of 1,2-dibromo-tetrachloroethane (90 g, 0.276 mol) in tetrahydrofuran (150 mL) was added dropwise while maintaining the temperature below −70° C. The reaction mixture turned a clear orange; stirring was continued for an additional 15 minutes. The −78° C. bath was removed and the reaction was quenched with water (600 mL). The reaction mixture was extracted with dichloromethane (4×) and the organic extracts were dried over magnesium sulfate and concentrated. The crude product was further purified by chromatography on silica gel using dichloromethane-hexane (50:50) as eluent to afford the title product as a clear colorless oil (57.04 g).
$^1$H NMR (CDCl$_3$) δ 3.07 (d, 6H), 6.44 (m, 1H), 7.62 (m, 1H).

Step C: Preparation of 3-bromopyrazole

To trifluoroacetic acid (70 mL) was slowly added 3-bromo-N,N-dimethyl-1H-pyrazole-1-sulfonamide (i.e. the bromopyrazole product of Step B) (57.04 g). The reaction mixture was stirred at room temperature for 30 minutes and then concentrated at reduced pressure. The residue was taken up in hexane, insoluble solids were filtered off, and the hexane was evaporated to afford the crude product as an oil. The crude product was further purified by chromatography on silica gel using ethyl acetate/dichloromethane (10:90) as eluent to afford an oil. The oil was taken up in dichloromethane, neutralized with aqueous sodium bicarbonate solution, extracted with dichloromethane (3×), dried over magnesium sulfate and concentrated to afford the title product as a white solid (25.9 g), m.p. 61-64° C.

$^1$H NMR (CDCl$_3$) δ 6.37 (d, 1H), 7.59 (d, 1H), 12.4 (br s, 1H).

Step D: Preparation of 2-(3-bromo-1H-pyrazol-1-yl)-3-chloropyridine

To a mixture of 2,3-dichloropyridine (27.4 g, 185 mmol) and 3-bromopyrazole (i.e. the product of Step C) (25.4 g, 176 mmol) in dry N,N-dimethylformamide (88 mL) was added potassium carbonate (48.6 g, 352 mmol), and the reaction mixture was heated to 125° C. for 18 hours. The reaction mixture was cooled to room temperature and poured into ice water (800 mL). A precipitate formed. The precipitated solids were stirred for 1.5 hours, filtered and washed with water (2×100 mL). The solid filter cake was taken up in dichloromethane and washed sequentially with water, 1N hydrochloric acid, saturated aqueous sodium bicarbonate solution, and brine. The organic extracts were then dried over magnesium sulfate and concentrated to afford 39.9 g of a pink solid. The crude solid was suspended in hexane and stirred vigorously for 1 hour. The solids were filtered, washed with hexane and dried to afford the title product as an off-white powder (30.4 g) determined to be >94% pure by NMR. This material was used without further purification in Step D.

$^1$H NMR (CDCl$_3$) δ 6.52 (s, 1H), 7.30 (dd, 1H), 7.92 (d, 1H), 8.05 (s, 1H), 8.43 (d, 1H).

Step E: Preparation of 3-bromo-1-(3-chloro-2-pyridinyl)-1H-pyrazole-5-carboxylic acid To a solution of 2-(3-bromo-1H-pyrazol-1-yl)-3-chloropyridine (i.e. the pyrazole product of Step D) (30.4 g, 118 mmol) in dry tetrahydrofuran (250 mL) at −76° C. was added dropwise a solution of lithium diisopropylamide (118 mmol) in tetrahydrofuran at such a rate as to maintain the temperature below −71° C. The reaction mixture was stirred for 15 minutes at −76° C., and carbon dioxide was then bubbled through for 10 minutes, causing warming to −57° C. The reaction mixture was warmed to −20° C. and quenched with water. The reaction mixture was concentrated and then taken up in water (1 L) and ether (500 mL), and then aqueous sodium hydroxide solution (1 N, 20 mL) was added. The phases were separated and the aqueous phase was washed with ether and acidified with hydrochloric acid. The precipitated solids were filtered, washed with water and dried to afford the title product as a tan solid (27.7 g). (Product from another run following similar procedure melted at 200-201° C.)

$^1$H NMR (DMSO-d$_6$) δ 7.25 (s, 1H), 7.68 (dd, 1H), 8.24 (d, 1H), 8.56 (d, 1H).

Step F: Preparation of 2-[3-bromo-1-(3-chloro-2-pyridinyl)-1H-pyrazol-5-yl]-6-chloro-8-methyl-4H-3,1-benzoxazin-4-one Methanesulfonyl chloride (1.0 mL, 1.5 g, 13 mmol) was dissolved in acetonitrile (10 mL), and the mixture was cooled to −5° C. A solution of 3-bromo-1-(3-chloro-2-pyridinyl)-1H-pyrazole-5-carboxylic acid (i.e. the pyrazolecarboxylic acid product of Step E) (3.02 g, 10 mmol) and pyridine (1.4 mL, 1.4 g, 17 mmol) in acetonitrile (10 mL) was added dropwise over five minutes at −5 to 0° C. A slurry formed during the addition. The mixture was stirred five minutes at this temperature, and then a mixture of 2-amino-3-methyl-5-chlorobenzoic acid (i.e. the product of Step A) (1.86 g, 10 mmol) and pyridine (2.8 mL, 2.7 g, 35 mmol) in acetonitrile (10 mL) was added, rinsing with more acetonitrile (5 mL). The mixture was stirred 15 minutes at −5 to 0° C., and then methanesulfonyl chloride (1.0 mL, 1.5 g, 13 mmol) in acetonitrile (5 mL) was added dropwise over five minutes at a temperature of −5 to 0° C. The reaction mixture was stirred 15 minutes more at this temperature, then allowed to warm slowly to room temperature, and stirred 4 hours. Water (20 mL) was added dropwise, and the mixture was stirred 15 minutes. The mixture was filtered, and the solids were washed with 2:1 acetonitrile-water (3×3 mL), then with acetonitrile (2×3 mL), and dried under nitrogen to afford the title product as a light yellow powder, 4.07 g (90.2% crude yield), melting at 203-205° C. HPLC of the product using a Zorbax® RX-C8 chromatography column (reversed phase column manufactured by Agilent Technologies containing n-octyldimethylsilyl groups bonded to 5-mm porous silica microspheres with 80 Å pore size) (4.6 mm×25 cm, eluent 25-95% acetonitrile/pH 3 water) showed a major peak corresponding to the title compound and having 95.7% of total chromatogram peak area.

$^1$H NMR (DMSO-d$_6$) δ 1.72 (s, 3H) 7.52 (s, 1H), 7.72-7.78 (m, 2H), 7.88 (m, 1H), 8.37 (dd, 1H), 8.62 (dd, 1H).

EXAMPLES 2-5

Preparation of 2-[3-bromo-1-(3-chloro-2-pyridinyl)-1H-pyrazol-5-yl]-6-chloro-8-methyl-4H-3,1-benzoxazin-4-one in Alternate Solvents Examples 2-5 were conducted by the method described for Example 1, Step F, except that the solvents shown in Table 1 were used in place of acetonitrile. In those cases where the filtrate formed two phases, the organic phase was separated, dried over magnesium sulfate, filtered, and evaporated, and the residue was triturated with acetonitrile to afford a second crop of 2-[3-bromo-1-(3-chloro-2-pyridinyl)-1H-pyrazol-5-yl]-6-chloro-8-methyl-4H-3,1-benzoxazin-4-one, though of lower purity.

TABLE 1

| Example | Solvent | First Crop (% Yield) | Second Crop (% Yield) | Total % Yield |
|---|---|---|---|---|
| 2 | Ethyl Acetate | 62.2 | 21 | 83.3 |
| 3 | Acetone | 86.2 | — | 86.2 |
| 4 | Tetrahydrofuran | 58.9 | 21 | 80.0 |
| 5 | Dichloromethane | 79.5 | 10 | 89.7 |

EXAMPLES 6-10

Preparation of 2-[3-bromo-1-(3-chloro-2-pyridinyl)-1H-pyrazol-5-yl]-6-chloro-8-methyl-4H-3,1-benzoxazin-4-one with Alternate Bases Examples 6-10 were conducted by the method described for Example 1, Step F, except that the bases shown in Table 2 were used in place of pyridine. In each case, the molar quantity of the base used was the same as the molar quantity of pyridine for which it was substituted.

TABLE 2

| Example | Base | % Yield | HPLC Area % |
|---|---|---|---|
| 6 | 3-picoline | 92.4 | 95.2 |
| 7 | 2,6-lutidine | 95.5 | 92.1 |
| 8 | Collidine | 90.4 | 78.1 |
| 9 | 2-picoline | 93.3 | 90.2 |
| 10 | 4-picoline | 68.5 | 78.0 |

EXAMPLES 11-12

Preparation of 2-[3-bromo-1-(3-chloro-2-pyridinyl)-1H-pyrazol-5-yl]-6-chloro-8-methyl-4H-3,1-benzoxazin-4-one with Alternate Sulfonyl Chlorides Examples 11 and 12 were conducted by the method described for Example 1, Step F, except that the sulfonyl chlorides shown in Table 3 were used in place of methanesulfonyl chloride. In each case, the molar quantity of the sulfonyl chloride used was the same as the molar quantity of methanesulfonyl chloride for which it was substituted.

TABLE 3

| Example | Sulfonyl Chloride | % Yield | HPLC Area % |
| --- | --- | --- | --- |
| 11 | Benzenesulfonyl Chloride | 87.5 | 96.5 |
| 12 | n-Propanesulfonyl Chloride | 93.5 | 95.0 |

EXAMPLE 13

Preparation of 6-chloro-2-[3-chloro-1-(3-chloro-2-pyridinyl)-1H-pyrazol-5-yl]-8-methyl-4H-3,1-benzoxazin-4-one Step A: Preparation of 3-chloro-N,N-dimethyl-1H-pyrazole-1-sulfonamide To a solution of N-dimethylsulfamoylpyrazole (188.0 g, 1.07 mol) in dry tetrahydrofuran (1500 mL) at −78° C. was added dropwise a solution of 2.5 M n-butyllithium (472 mL, 1.18 mol) in hexane while maintaining the temperature below −65° C. Upon completion of the addition the reaction mixture was maintained at −78° C. for an additional 45 minutes, after which time a solution of hexachloroethane (279 g, 1.18 mol) in tetrahydrofuran (120 mL) was added dropwise. The reaction mixture was maintained for an hour at −78° C., warmed to −20° C. and then quenched with water (1 L). The reaction mixture was extracted with dichloromethane (4×500 mL); the organic extracts were dried over magnesium sulfate and concentrated. The crude product was further purified by chromatography on silica gel using dichloromethane as eluent to afford the title compound as a yellow oil (160 g).

$^1$H NMR (CDCl$_3$) δ 3.07 (d, 6H), 6.33 (s, 1H), 7.61 (s, 1H).

Step B: Preparation of 3-chloropyrazole

To trifluoroacetic acid (290 mL) was added dropwise 3-chloro-N,N-dimethyl-1H-pyrazole-1-sulfonamide (i.e. the chloropyrazole product of Step A) (160 g), and the reaction mixture was stirred at room temperature for 1.5 hours and then concentrated at reduced pressure. The residue was taken up in hexane, insoluble solids were filtered off, and the hexane was concentrated to afford the crude product as an oil. The crude product was further purified by chromatography on silica gel using ether/hexane (40:60) as eluent to afford the title compound as a yellow oil (64.44 g).

$^1$H NMR (CDCl$_3$) δ 6.39 (s, 1H), 7.66 (s, 1H), 9.6 (br s, 1H).

Step C: Preparation of 3-chloro-2-(3-chloro-1H-pyrazol-1-yl)pyridine

To a mixture of 2,3-dichloropyridine (92.60 g, 0.629 mol) and 3-chloropyrazole (i.e. the product of Step B) (64.44 g, 0.629 mol) in N,N-dimethylformamide (400 mL) was added potassium carbonate (147.78 g, 1.06 mol), and the reaction mixture was then heated to 100° C. for 36 hours. The reaction mixture was cooled to room temperature and slowly poured into ice water. The precipitated solids were filtered and washed with water. The solid filter cake was taken up in ethyl acetate, dried over magnesium sulfate and concentrated. The crude solid was chromatographed on silica gel using 20% ethyl acetate/hexane as eluent to afford the title product as a white solid (39.75 g).

$^1$H NMR (CDCl$_3$) δ 6.43 (s, 1H), 7.26 (m, 1H), 7.90 (d, 1H), 8.09 (s, 1H), 8.41 (d, 1H).

Step D: Preparation of 3-chloro-1-(3-chloro-2-pyridinyl)-1H-pyrazole-5-carboxylic acid To a solution of 3-chloro-2-(3-chloro-1H-pyrazol-1-yl)pyridine (i.e. the pyrazole product of Step C) (39.75 g, 186 mmol) in dry tetrahydrofuran (400 mL) at −78° C. was added dropwise a solution of 2.0 M lithium diisopropylamide (93 mL, 186 mmol) in tetrahydrofuran. Carbon dioxide was bubbled through the amber solution for 14 minutes, after which time the solution became pale brownish-yellow. The reaction was made basic with 1 N aqueous sodium hydroxide solution and extracted with ether (2×500 mL). The aqueous extracts were acidified with 6 N hydrochloric acid and extracted with ethyl acetate (3×500 mL). The ethyl acetate extracts were dried over magnesium sulfate and concentrated to afford the title product as an off-white solid (42.96 g). (Product from another run following a similar procedure melted at 198-199° C.)

$^1$H NMR (DMSO-d$_6$) δ 6.99 (s, 1H), 7.45 (m, 1H), 7.93 (d, 1H), 8.51 (d, 1H).

Step E: Preparation of 6-chloro-2-[3-chloro-1-(3-chloro-2-pyridinyl)-1H-pyrazol-5-yl]-8-methyl-4H-3,1-benzoxazin-4-one Methanesulfonyl chloride (1.0 mL, 1.5 g, 13 mmol) was dissolved in acetonitrile (10 mL), and the mixture was cooled to −5° C. A solution of 3-chloro-1-(3-chloro-2-pyridinyl)-1H-pyrazole-5-carboxylic acid (i.e. the carboxylic acid product of Step D) (2.58 g, 10 mmol) and pyridine (1.4 mL, 1.4 g, 17 mmol) in acetonitrile (10 mL) was added dropwise over five minutes at −5 to 0° C. A slurry formed during the addition. The mixture was stirred five minutes at this temperature, and then 2-amino-3-methyl-5-chlorobenzoic acid (i.e. the product from Example 1, Step A) (1.86 g, 10 mmol) was added all at once. Then a solution of pyridine (2.8 mL, 2.7 g, 35 mmol) in acetonitrile (10 mL) was added dropwise over five minutes at −5 to 0° C. The mixture was stirred 15 minutes at −5 to 0° C., and then methanesulfonyl chloride (1.0 mL, 1.5 mL, 13 mmol) in acetonitrile (5 mL) was added dropwise over five minutes at −5 to 0° C. The reaction mixture was stirred 15 minutes at this temperature, then allowed to warm slowly to room temperature, and stirred for 4 hours. Water (15 mL) was added dropwise, and the mixture was stirred 15 minutes. Then the mixture was filtered, and the solids were washed with 2:1 acetonitrile-water (3×3 mL), then with acetonitrile (2×3 mL), and dried under nitrogen to afford the title product as a pale yellow powder, 3.83 g (94.0% crude yield), melting at 199-201° C. HPLC of the product using a Zorbax® Rx-C8 chromatography column (4.6 mm×25 cm, eluent 25-95% acetonitrile/pH 3 water) showed a major peak corresponding to the title compound and having 97.8% of total chromatogram peak area.

$^1$H NMR (DMSO-d$_6$) δ 1.72 (s, 3H), 7.48 (s, 1H), 7.74-7.80 (m, 2H), 7.87 (m, 1H), 8.37 (dd, 1H), 8.62 (dd, 1H).

EXAMPLE 14

Preparation of a mixture of 2-[3-bromo-1-(3,4-dichloro-2-pyridinyl)-1H-pyrazol-5-yl]-6-chloro-8-methyl-4H-3,1-benzoxazin-4-one and 2-[3-bromo-1-(3,6-dichloro-2-pyridinyl)-1H-pyrazol-5-yl]-6-chloro-8-methyl-4H-3,1-benzoxazin-4-one By the method described above for preparation of Example 13, except that a mixture of 3-bromo-1-(3,4-dichloro-2-pyridinyl)-1H-pyrazole-5-carboxylic acid and 3-bromo-1-(3,6-dichloro-2-pyridinyl)-1H-pyrazole-5-carboxylic acid (mixture of isomers, 3.37 g, 10 mmol) was used in place of 3-chloro-1-(3-chloro-2-pyridinyl)-1H-pyrazole-5-carboxylic acid. The title compound mixture was obtained as light yellow solids, 4.35 g (89.4% crude yield), m.p. 195-210° C. HPLC of the product on a Zorbax® Rx-C8 column (4.6 mm×25 cm, eluent 25-95% acetonitrile/pH 3 water) showed 86.9 area % for the mixture of isomers.

$^1$H NMR (DMSO-$d_6$) δ 1.75 and 1.80 (each s, total 3H) 7.56 and 7.56 (each s, total 1H), 7.80 and 7.90 (each m, total 2H), 7.96 and 8.12 (each d, total 1H), 8.44 and 8.61 (each d, total 1H).

EXAMPLE 15

Preparation of 2-[3-bromo-1-(3-chloro-1-oxido-2-pyridinyl)-1H-pyrazol-5-yl]-6-chloro-8-methyl-4H-3,1-benzoxazin-4-one Methanesulfonyl chloride (0.50 mL, 0.74 g, 6.5 mmol) was dissolved in acetonitrile (5 mL) and the mixture was cooled to −5° C. A mixture of 3-chloro-1-(3-chloro-1-oxido-2-pyridinyl)-1H-pyrazole-5-carboxylic acid (1.59 g, 5.0 mmol) and pyridine (0.69 mL, 0.67 g, 8.5 mmol) in acetonitrile (5 mL) formed a slurry and was added dropwise over five minutes at −5 to 0° C. The mixture was stirred five minutes at this temperature, then 2-amino-3-methyl-5-chlorobenzoic acid (i.e. the product from Example 1, Step A) (0.93 g, 5.0 mmol) was added all at once. Then a solution of pyridine (1.4 mL, 1.4 g, 17 mmol) in acetonitrile (2.5 mL) was added dropwise over five minutes at −5 to 0° C. The mixture was stirred 15 minutes at −5 to 0° C., then methanesulfonyl chloride (0.50 mL, 0.74 g, 6.5 mmol) in acetonitrile (2.5 mL) was added dropwise over five minutes at −5 to 0° C. The reaction mixture was stirred 15 minutes at this temperature, then allowed to warm slowly to room temperature, and stirred 3 hours. Water (7.5 mL) was added dropwise, and the mixture was stirred 15 minutes. Then the mixture was filtered and the solids were washed with 2:1 acetonitrile-water (3×1.5 mL), then with acetonitrile (2×1.5 mL), and dried under nitrogen to afford the title compound as an off-white powder, 2.05 g (87.6% crude yield), m.p. 240-245° C. (decomposed). HPLC of the product on a Zorbax® Rx-C8 column (4.6 mm×25 cm, eluent 25-95% acetonitrile/pH 3 water) showed 96.1 area % of the title compound.

$^1$H NMR (DMSO-$d_6$) δ 1.87 (s, 3H), 7.61 (s, 1H), 7.66-7.74 (m, 1H), 7.84 (d, 1H), 7.89 (d, 1H), 8.52 (d, 1H).

By the methods and procedures described herein together with methods known in the art, the following compounds of Table 4 can be prepared.

TABLE 4

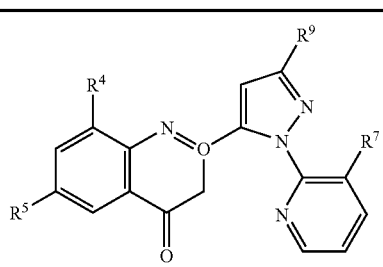

| R$^4$ | R$^5$ | R$^9$ | R$^7$ |
|---|---|---|---|
| CH$_3$ | F | CF$_3$ | Cl |
| CH$_3$ | F | CF$_3$ | Br |
| CH$_3$ | F | Cl | Cl |
| CH$_3$ | F | Cl | Br |
| CH$_3$ | F | Br | Cl |
| CH$_3$ | F | Br | Br |
| CH$_3$ | Cl | CF$_3$ | Cl |
| CH$_3$ | Cl | CF$_3$ | Br |
| CH$_3$ | Cl | Cl | Cl |
| CH$_3$ | Cl | Cl | Br |
| CH$_3$ | Cl | Br | Cl |
| CH$_3$ | Cl | Br | Br |
| CH$_3$ | Br | CF$_3$ | Cl |
| CH$_3$ | Br | CF$_3$ | Br |
| CH$_3$ | Br | Cl | Cl |
| CH$_3$ | Br | Cl | Br |
| CH$_3$ | Br | Br | Cl |
| CH$_3$ | Br | Br | Br |
| CH$_3$ | I | CF$_3$ | Cl |
| CH$_3$ | I | CF$_3$ | Br |
| CH$_3$ | I | Cl | Cl |
| CH$_3$ | I | Cl | Br |
| CH$_3$ | I | Br | Cl |
| CH$_3$ | I | Br | Br |
| CH$_3$ | CF$_3$ | CF$_3$ | Cl |
| CH$_3$ | CF$_3$ | CF$_3$ | Br |
| CH$_3$ | CF$_3$ | Cl | Cl |
| CH$_3$ | CF$_3$ | Cl | Br |
| CH$_3$ | CF$_3$ | Br | Cl |
| CH$_3$ | CF$_3$ | Br | Br |
| CH$_3$ | Cl | Cl | Cl |
| F | F | CF$_3$ | Cl |
| F | F | CF$_3$ | Br |
| F | F | Cl | Cl |
| F | F | Cl | Br |
| F | F | Br | Cl |
| F | F | Br | Br |
| F | Cl | CF$_3$ | Cl |
| F | Cl | CF$_3$ | Br |
| F | Cl | Cl | Cl |
| F | Cl | Cl | Br |
| F | Cl | Br | Cl |
| F | Cl | Br | Br |
| F | Br | CF$_3$ | Cl |
| F | Br | CF$_3$ | Br |
| F | Br | Cl | Cl |
| F | Br | Cl | Br |
| F | Br | Br | Cl |
| F | Br | Br | Br |
| F | I | CF$_3$ | Cl |
| F | I | CF$_3$ | Br |
| F | I | Cl | Cl |
| F | I | Cl | Br |
| F | I | Br | Cl |
| F | I | Br | Br |
| F | CF$_3$ | CF$_3$ | Cl |
| F | CF$_3$ | CF$_3$ | Br |
| F | CF$_3$ | Cl | Cl |
| F | CF$_3$ | Cl | Br |
| F | CF$_3$ | Br | Cl |
| F | CF$_3$ | Br | Br |
| F | F | OCHF$_2$ | Cl |
| F | F | OCHF$_2$ | Br |
| F | Cl | OCHF$_2$ | Cl |

TABLE 4-continued

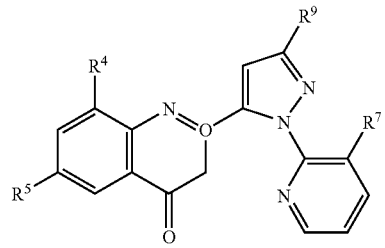

| R4 | R5 | R9 | R7 |
|---|---|---|---|
| F | Cl | OCHF2 | Br |
| F | I | OCHF2 | Cl |
| F | I | OCHF2 | Br |
| Cl | F | CF3 | Cl |
| Cl | F | CF3 | Br |
| Cl | F | Cl | Cl |
| Cl | F | Cl | Br |
| Cl | F | Br | Cl |
| Cl | F | Br | Br |
| Cl | Cl | CF3 | Cl |
| Cl | Cl | CF3 | Br |
| Cl | Cl | Cl | Cl |
| Cl | Cl | Cl | Br |
| Cl | Cl | Br | Cl |
| Cl | Cl | Br | Br |
| Cl | Br | CF3 | Cl |
| Cl | Br | CF3 | Br |
| Cl | Br | Cl | Cl |
| Cl | Br | Cl | Br |
| Cl | Br | Br | Cl |
| Cl | Br | Br | Br |
| Cl | I | CF3 | Cl |
| Cl | I | CF3 | Br |
| Cl | I | Cl | Cl |
| Cl | I | Cl | Br |
| Cl | I | Br | Cl |
| Cl | I | Br | Br |
| Cl | CF3 | CF3 | Cl |
| Cl | CF3 | CF3 | Br |
| Cl | CF3 | Cl | Cl |
| Cl | CF3 | Cl | Br |
| Cl | CF3 | Br | Cl |
| Cl | CF3 | Br | Br |
| Cl | Cl | Cl | Cl |
| Br | F | CF3 | Cl |
| Br | F | CF3 | Br |
| Br | F | Cl | Cl |
| Br | F | Cl | Br |
| Br | F | Br | Cl |
| Br | F | Br | Br |
| Br | Cl | CF3 | Cl |
| Br | Cl | CF3 | Br |
| Br | Cl | Cl | Cl |
| Br | Cl | Cl | Br |
| Br | Cl | Br | Cl |
| Br | Cl | Br | Br |
| Br | Br | CF3 | Cl |
| Br | Br | CF3 | Br |
| Br | Br | Cl | Cl |
| Br | Br | Cl | Br |
| Br | Br | Br | Cl |
| Br | Br | Br | Br |
| Br | I | CF3 | Cl |
| Br | I | CF3 | Br |
| Br | I | Cl | Cl |
| Br | I | Cl | Br |
| Br | I | Br | Cl |
| Br | I | Br | Br |
| Br | CF3 | CF3 | Cl |
| Br | CF3 | CF3 | Br |
| Br | CF3 | Cl | Cl |
| Br | CF3 | Cl | Br |
| Br | CF3 | Br | Cl |
| Br | CF3 | Br | Br |

TABLE 4-continued

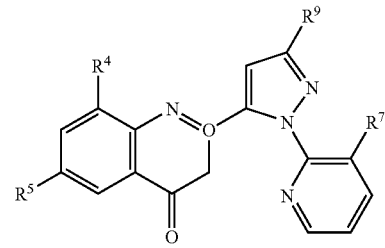

| R4 | R5 | R9 | R7 |
|---|---|---|---|
| Br | F | OCHF2 | Cl |
| Br | F | OCHF2 | Br |
| Br | Cl | OCHF2 | Cl |
| Br | Cl | OCHF2 | Br |
| Br | Br | OCHF2 | Cl |
| Br | Br | OCHF2 | Br |
| CH3 | F | OCH2CF3 | Cl |
| CH3 | F | OCH2CF3 | Br |
| CH3 | F | OCHF2 | Cl |
| CH3 | F | OCHF2 | Br |
| Cl | F | OCH2CF3 | Cl |
| Cl | F | OCH2CF3 | Br |
| Cl | F | OCHF2 | Cl |
| Cl | F | OCHF2 | Br |
| CH3 | Cl | OCH2CF3 | Cl |
| CH3 | Cl | OCH2CF3 | Br |
| CH3 | Cl | OCHF2 | Cl |
| CH3 | Cl | OCHF2 | Br |
| Cl | Cl | OCH2CF3 | Cl |
| Cl | Cl | OCH2CF3 | Br |
| Cl | Cl | OCHF2 | Cl |
| Cl | Cl | OCHF2 | Br |
| CH3 | Br | OCH2CF3 | Cl |
| CH3 | Br | OCH2CF3 | Br |
| CH3 | Br | OCHF2 | Cl |
| CH3 | Br | OCHF2 | Br |
| Cl | Br | OCH2CF3 | Cl |
| Cl | Br | OCH2CF3 | Br |
| Cl | Br | OCHF2 | Cl |
| Cl | Br | OCHF2 | Br |
| Cl | I | OCH2CF3 | Cl |
| Cl | I | OCH2CF3 | Br |
| Cl | I | OCHF2 | Cl |
| Cl | I | OCHF2 | Br |
| CH3 | I | OCH2CF3 | Cl |
| CH3 | I | OCH2CF3 | Br |
| CH3 | I | OCHF2 | Cl |
| CH3 | I | OCHF2 | Br |
| Cl | CF3 | OCH2CF3 | Cl |
| Cl | CF3 | OCH2CF3 | Br |
| Cl | CF3 | OCHF2 | Cl |
| Cl | CF3 | OCHF2 | Br |
| CH3 | CF3 | OCH2CF3 | Cl |
| CH3 | CF3 | OCH2CF3 | Br |
| CH3 | CF3 | OCHF2 | Cl |
| CH3 | CF3 | OCHF2 | Br |
| Br | F | OCH2CF3 | Cl |
| Br | F | OCH2CF3 | Br |
| F | F | OCH2CF3 | Cl |
| F | F | OCH2CF3 | Br |
| Br | Cl | OCH2CF3 | Cl |
| Br | Cl | OCH2CF3 | Br |
| F | Cl | OCH2CF3 | Cl |
| F | Cl | OCH2CF3 | Br |
| Br | Br | OCH2CF3 | Cl |
| Br | Br | OCH2CF3 | Br |
| F | Br | OCH2CF3 | Cl |
| F | Br | OCH2CF3 | Br |
| F | Br | OCHF2 | Cl |
| F | Br | OCHF2 | Br |
| Br | I | OCH2CF3 | Cl |
| Br | I | OCH2CF3 | Br |
| Br | I | OCHF2 | Cl |
| Br | I | OCHF2 | Br |

TABLE 4-continued

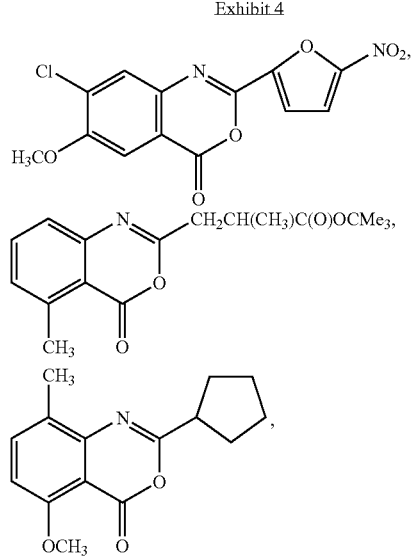

| R$^4$ | R$^5$ | R$^9$ | R$^7$ |
|---|---|---|---|
| F | I | OCH$_2$CF$_3$ | Cl |
| F | I | OCH$_2$CF$_3$ | Br |
| Br | CF$_3$ | OCH$_2$CF$_3$ | Cl |
| Br | CF$_3$ | OCH$_2$CF$_3$ | Br |
| Br | CF$_3$ | OCHF$_2$ | Cl |
| Br | CF$_3$ | OCHF$_2$ | Br |
| F | CF$_3$ | OCH$_2$CF$_3$ | Cl |
| F | CF$_3$ | OCH$_2$CF$_3$ | Br |
| F | CF$_3$ | OCHF$_2$ | Cl |
| F | CF$_3$ | OCHF$_2$ | Br |

The fused oxazinone preparation method of the present invention can be used to prepare a wide variety of compounds of Formula 1 that are useful as intermediates for the preparation of crop protection agents, pharmaceuticals and other fine chemicals. Exhibit 4 lists examples of fused oxazinones which can be prepared according to the method of the present invention from corresponding carboxylic acids of Formula 2 and ortho-amino carboxylic acids of Formula 5, including fused oxazinones which are useful in the preparation of products having antiviral, nematocidal, microbiocidal, acaricidal, fungicidal and herbicidal utility. These examples are to be construed as illustrative, but not limiting, of the diverse scope of applicability of the method of the present invention. Other compounds preparable according to the method of the present invention may be useful for preparation of pharmaceutical products having additional utilities, such as anti-tumor activity, anti-allergenic activity, protease inhibition, etc.

Exhibit 4

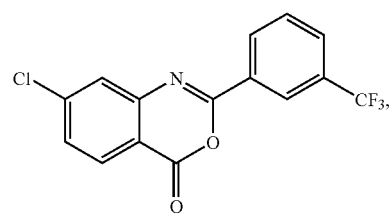

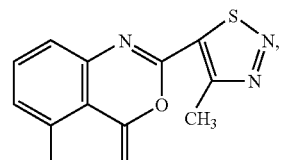

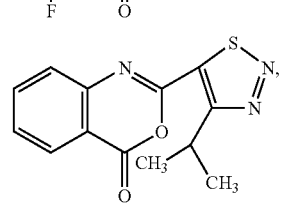

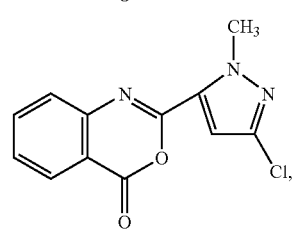

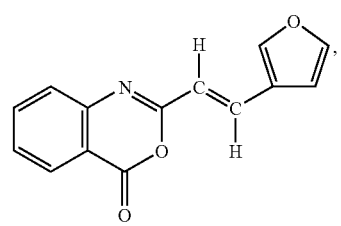

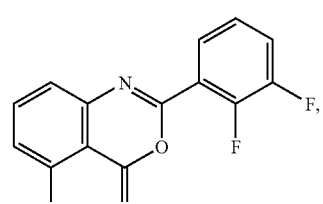

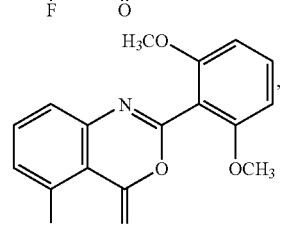

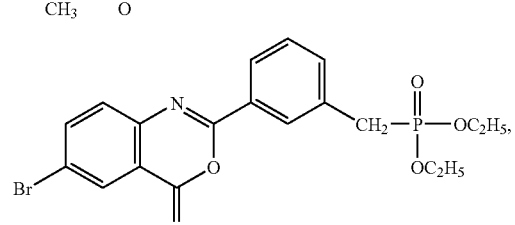

-continued
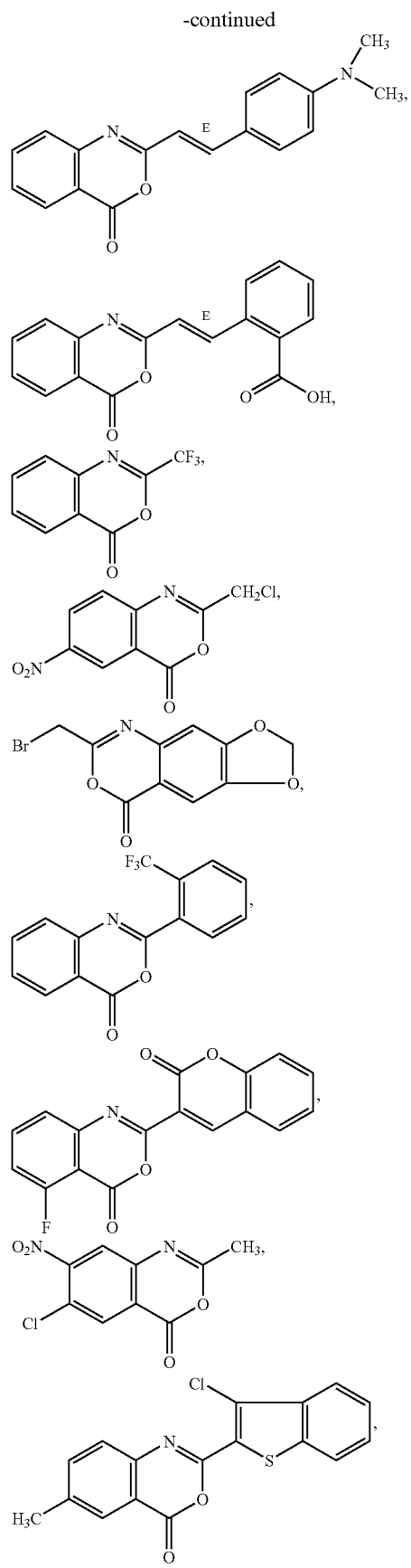
-continued
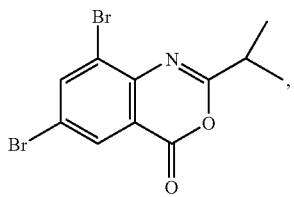
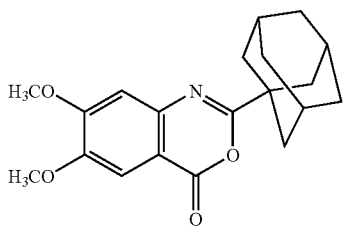
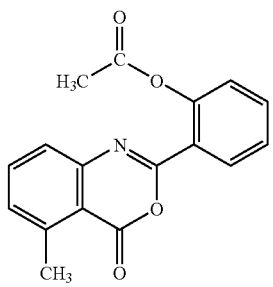
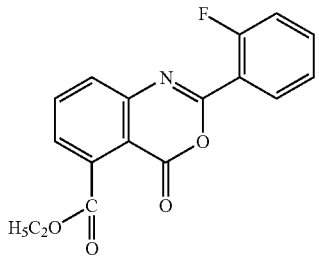
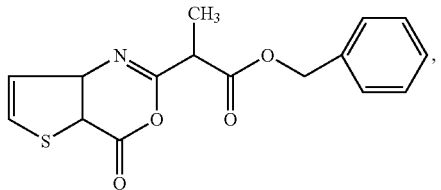
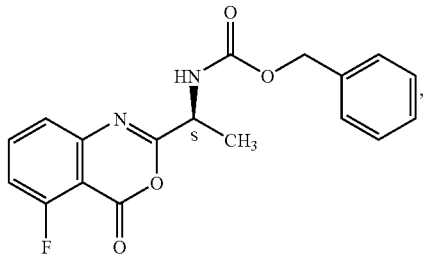
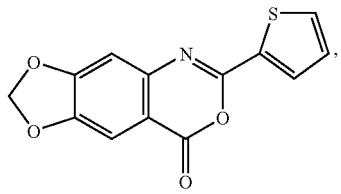

-continued

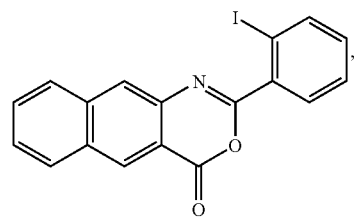

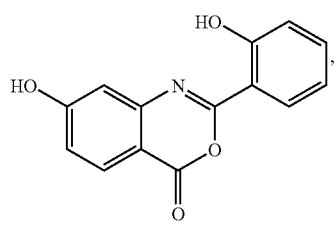

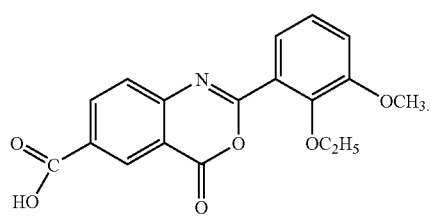

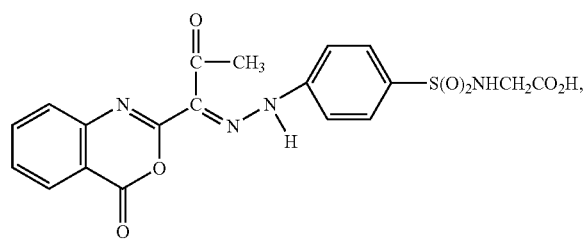

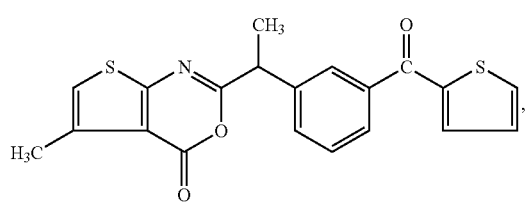

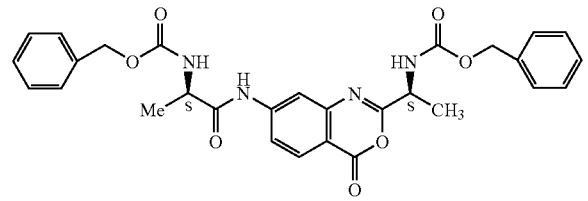

Furthermore as shown in Scheme A, compounds of Formula 1 can be used to prepare compounds of Formula II by reaction with nucleophiles (Nuc), optionally in the presence of additional base.

Scheme A

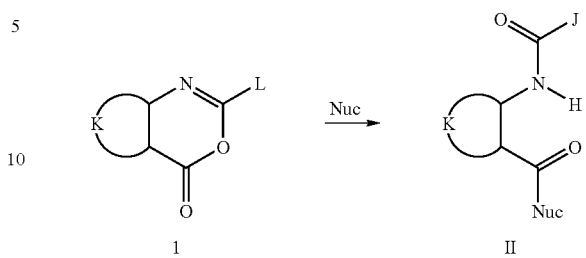

As shown in Scheme 28, reaction of Formula 1 with nucleophiles of Formula 77 wherein $R^d$ can be an optionally substituted carbon moiety (i.e. alcohols) leads to esters of Formula IIa. Reaction of Formula 1 with nucleophiles of Formula 78 wherein $R^e$ and $R^f$ can be independently H or an optionally substituted carbon moiety (i.e. ammonia, primary amines or secondary amines) leads to amides of Formula IIb.

Scheme 28

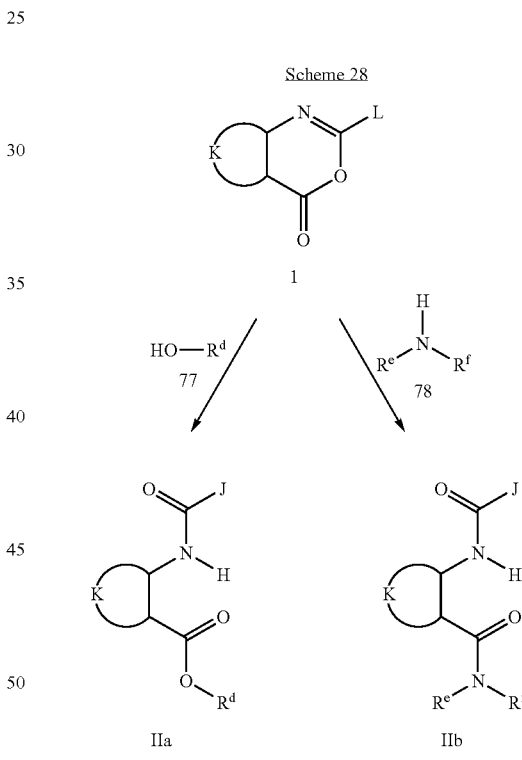

Typical procedures for preparation of compounds of Formula IIb involve combination of an amine of Formula 78 with the fused oxazinone of Formula 1. The reaction can be run neat or in a variety of suitable solvents including acetonitrile, tetrahydrofuran, diethyl ether, dichloromethane or chloroform with optimum temperatures ranging from room temperature to the reflux temperature of the solvent. For references to the chemistry of heterocyclic fused oxazinones see Jakobsen et al., *Biorganic and Medicinal Chemistry* 2000, 8, 2803 2812 and references cited therein.

As a particular example, compounds of Formula Ia are useful for preparing compounds of Formula III

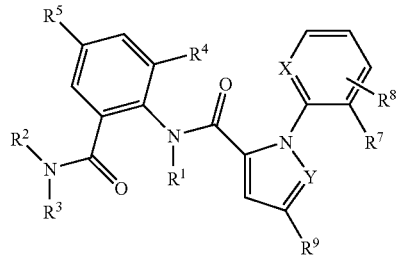

wherein
X is N or CR$^6$;
Y is N or CH;
R$^1$ is H;
R$^2$ is H or CH$_3$;
R$^3$ is C$_1$-C$_6$ alkyl;
R$^4$ is C$_1$-C$_4$ alkyl or halogen;
R$^5$ is H, C$_1$-C$_4$ alkyl, C$_1$-C$_4$ haloalkyl or halogen;
R$^6$ and R$^7$ are independently H, C$_1$-C$_4$ alkyl, C$_1$-C$_4$ haloalkyl, halogen, CN or C$_1$-C$_4$ haloalkoxy;
R$^8$ is H, C$_1$-C$_4$ alkyl, C$_2$-C$_4$ alkenyl, C$_2$-C$_4$ alkynyl, C$_3$-C$_6$ cycloalkyl, C$_1$-C$_4$ haloalkyl, C$_2$-C$_4$ haloalkenyl, C$_2$-C$_4$ haloalkynyl, C$_3$-C$_6$ halocycloalkyl, halogen, CN, NO$_2$, C$_1$-C$_4$ alkoxy, C$_1$-C$_4$ haloalkoxy, C$_1$-C$_4$ alkylthio, C$_1$-C$_4$ alkylsulfinyl, C$_1$-C$_4$ alkylsulfonyl, C$_1$-C$_4$ alkylamino, C$_2$-C$_8$ dialkylamino, C$_3$-C$_6$ cycloalkylamino, (C$_1$-C$_4$ alkyl)(C$_3$-C$_6$ cycloalkyl)amino, C$_2$-C$_4$ alkylcarbonyl, C$_2$-C$_6$ alkoxycarbonyl, C$_2$-C$_6$ alkylaminocarbonyl, C$_3$-C$_8$ dialkylaminocarbonyl or C$_3$-C$_6$ trialkylsilyl;
R$^9$ is CF$_3$, OCF$_3$, OCHF$_2$, OCH$_2$CF$_3$, S(O)$_p$CF$_3$, S(O)$_p$CHF$_2$ or halogen; and
p is 0, 1 or 2.

Compounds of Formula III are useful as insecticides, as described, for example, in PCT Publication No. WO 01/70671, published Sep. 27, 2001, as well as in U.S. Patent Application 60/324,173, filed Sep. 21, 2001, U.S. Patent Application 60/323,941, filed Sep. 21, 2001 and U.S. Patent Application 60/369,661, filed Apr. 2, 2002. The preparation of compounds of Formula 1a and Formula III is described in U.S. Patent Application 60/400,356, filed Jul. 31, 2002 [BA9307 US PRV], and U.S. Patent Application 60/446,451, filed Feb. 11, 2003 [BA9307 US PRV1] and hereby incorporated herein in their entirety by reference; as well as in U.S. Patent Application 60/369,659, filed Apr. 2, 2002 and U.S. Patent Application 60/369,660, filed Apr. 2, 2002.

Compounds of Formula III can be prepared by the reaction of benzoxazinones of Formula 1a with C$_1$-C$_6$ alkylamines and (C$_1$-C$_6$ alkyl)(methyl)amines of Formula 79 as outlined in Scheme 29.

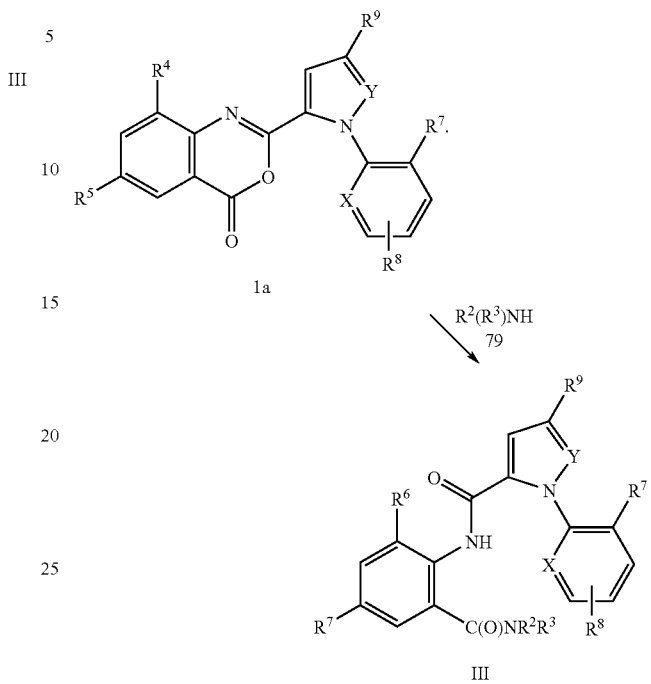

The reaction can be run neat or in a variety of suitable solvents including acetonitrile, tetrahydrofuran, diethyl ether, dichloromethane or chloroform with optimum temperatures ranging from room temperature to the reflux temperature of the solvent. The general reaction of benzoxazinones with amines to produce anthranilamides is well documented in the chemical literature. For a review of benzoxazinone chemistry see Jakobsen et al., *Biorganic and Medicinal Chemistry* 2000, 8, 2095-2103 and references cited within. See also Coppola, *J. Heterocyclic Chemistry* 1999, 36, 563-588.

Of note are methods for preparing compounds of Formula 1a or Formula III wherein R$^9$ is CF$_3$, OCF$_3$, OCHF$_2$, OCH$_2$CF$_3$ or halogen. Of particular note are methods for preparing compounds of Formula 1a or Formula III wherein R$^9$ is CF$_3$, OCHF$_2$, OCH$_2$CF$_3$, Cl or Br. Preferred are methods for preparing compounds of Formula 1a or Formula III
wherein
X is N;
Y is N;
R$^2$ is H or CH$_3$;
R$^3$ is C$_1$-C$_4$ alkyl;
R$^4$ is CH$_3$, F, Cl or Br;
R$^5$ is CF$_3$, F, Cl, Br or I;
R$^7$ is Cl or Br;
R$^8$ is H, and
R$^9$ is CF$_3$, OCHF$_2$, OCH$_2$CF$_3$, Cl or Br.

Also of particular note are compounds of Formula III wherein R$^9$ is OCHF$_2$.

By the procedures described herein together with methods known in the art, the following compounds of Table 5 can be prepared. The following abbreviations are used in the Tables which follow: t means tertiary, s means secondary, n means normal, i means iso, Me means methyl, Et means ethyl, Pr means propyl, i-Pr means isopropyl, and Bu means butyl.

TABLE 5

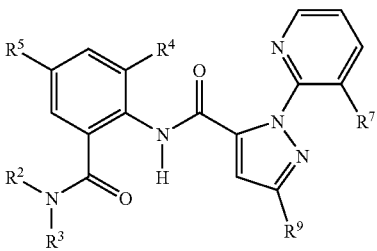

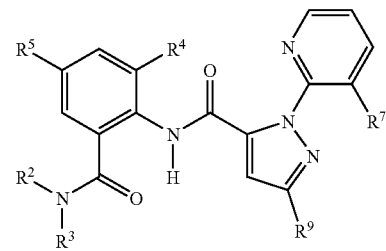

| R⁴ | R⁵ | R⁹ | R³ | R² | R⁷ |
|---|---|---|---|---|---|
| CH₃ | F | CF₃ | Me | H | Cl |
| CH₃ | F | CF₃ | Et | H | Cl |
| CH₃ | F | CF₃ | i-Pr | H | Cl |
| CH₃ | F | CF₃ | t-Bu | H | Cl |
| CH₃ | F | CF₃ | Me | Me | Cl |
| CH₃ | F | CF₃ | Me | H | Br |
| CH₃ | F | CF₃ | Et | H | Br |
| CH₃ | F | CF₃ | i-Pr | H | Br |
| CH₃ | F | CF₃ | t-Bu | H | Br |
| CH₃ | F | CF₃ | Me | Me | Br |
| CH₃ | F | Cl | Me | H | Cl |
| CH₃ | F | Cl | Et | H | Cl |
| CH₃ | F | Cl | i-Pr | H | Cl |
| CH₃ | F | Cl | t-Bu | H | Cl |
| CH₃ | F | Cl | Me | Me | Cl |
| CH₃ | F | Cl | Me | H | Br |
| CH₃ | F | Cl | Et | H | Br |
| CH₃ | F | Cl | i-Pr | H | Br |
| CH₃ | F | Cl | t-Bu | H | Br |
| CH₃ | F | Cl | Me | Me | Br |
| CH₃ | F | Br | Me | H | Cl |
| CH₃ | F | Br | Et | H | Cl |
| CH₃ | F | Br | i-Pr | H | Cl |
| CH₃ | F | Br | t-Bu | H | Cl |
| CH₃ | F | Br | Me | Me | Cl |
| CH₃ | F | Br | Me | H | Br |
| CH₃ | F | Br | Et | H | Br |
| CH₃ | F | Br | i-Pr | H | Br |
| CH₃ | F | Br | t-Bu | H | Br |
| CH₃ | F | Br | Me | Me | Br |
| CH₃ | F | OCH₂CF₃ | Me | H | Cl |
| CH₃ | F | OCH₂CF₃ | Et | H | Cl |
| CH₃ | F | OCH₂CF₃ | i-Pr | H | Cl |
| CH₃ | F | OCH₂CF₃ | t-Bu | H | Cl |
| CH₃ | F | OCH₂CF₃ | Me | Me | Cl |
| CH₃ | F | OCH₂CF₃ | Me | H | Br |
| CH₃ | F | OCH₂CF₃ | Et | H | Br |
| CH₃ | F | OCH₂CF₃ | i-Pr | H | Br |
| CH₃ | F | OCH₂CF₃ | t-Bu | H | Br |
| CH₃ | F | OCH₂CF₃ | Me | Me | Br |
| CH₃ | Cl | CF₃ | Me | H | Cl |
| CH₃ | Cl | CF₃ | Et | H | Cl |
| CH₃ | Cl | CF₃ | i-Pr | H | Cl |
| CH₃ | Cl | CF₃ | t-Bu | H | Cl |
| CH₃ | Cl | CF₃ | Me | Me | Cl |
| CH₃ | Cl | CF₃ | Me | H | Br |
| CH₃ | Cl | CF₃ | Et | H | Br |
| CH₃ | Cl | CF₃ | i-Pr | H | Br |
| CH₃ | Cl | CF₃ | t-Bu | H | Br |
| CH₃ | Cl | CF₃ | Me | Me | Br |
| CH₃ | Cl | Cl | Me | H | Cl |
| CH₃ | Cl | Cl | Et | H | Cl |
| CH₃ | Cl | Cl | i-Pr | H | Cl |
| CH₃ | Cl | Cl | t-Bu | H | Cl |
| CH₃ | Cl | Cl | Me | Me | Cl |
| CH₃ | Cl | Cl | Me | H | Br |
| CH₃ | Cl | Cl | Et | H | Br |
| CH₃ | Cl | Cl | i-Pr | H | Br |
| CH₃ | Cl | Cl | t-Bu | H | Br |
| CH₃ | Cl | Cl | Me | Me | Br |
| CH₃ | Cl | Br | Me | H | Cl |
| CH₃ | Cl | Br | Et | H | Cl |
| CH₃ | Cl | Br | i-Pr | H | Cl |
| CH₃ | Cl | Br | t-Bu | H | Cl |
| CH₃ | Cl | Br | Me | Me | Cl |
| CH₃ | Cl | Br | Me | H | Br |
| CH₃ | Cl | Br | Et | H | Br |
| CH₃ | Cl | Br | i-Pr | H | Br |
| CH₃ | Cl | Br | t-Bu | H | Br |
| CH₃ | Cl | Br | Me | Me | Br |
| CH₃ | Cl | OCH₂CF₃ | Me | H | Cl |
| CH₃ | Cl | OCH₂CF₃ | Et | H | Cl |
| CH₃ | Cl | OCH₂CF₃ | i-Pr | H | Cl |
| CH₃ | Cl | OCH₂CF₃ | t-Bu | H | Cl |
| CH₃ | Cl | OCH₂CF₃ | Me | Me | Cl |
| CH₃ | Cl | OCH₂CF₃ | Me | H | Br |
| CH₃ | Cl | OCH₂CF₃ | Et | H | Br |
| CH₃ | Cl | OCH₂CF₃ | i-Pr | H | Br |
| CH₃ | Cl | OCH₂CF₃ | t-Bu | H | Br |
| CH₃ | Cl | OCH₂CF₃ | Me | Me | Br |
| CH₃ | Br | CF₃ | Me | H | Cl |
| CH₃ | Br | CF₃ | Et | H | Cl |
| CH₃ | Br | CF₃ | i-Pr | H | Cl |
| CH₃ | Br | CF₃ | t-Bu | H | Cl |
| CH₃ | Br | CF₃ | Me | Me | Cl |
| CH₃ | Br | CF₃ | Me | H | Br |
| CH₃ | Br | CF₃ | Et | H | Br |
| CH₃ | Br | CF₃ | i-Pr | H | Br |
| CH₃ | Br | CF₃ | t-Bu | H | Br |
| CH₃ | Br | CF₃ | Me | Me | Br |
| CH₃ | Br | Cl | Me | H | Cl |
| CH₃ | Br | Cl | Et | H | Cl |
| CH₃ | Br | Cl | i-Pr | H | Cl |
| CH₃ | Br | Cl | t-Bu | H | Cl |
| CH₃ | Br | Cl | Me | Me | Cl |
| CH₃ | Br | Cl | Me | H | Br |
| CH₃ | Br | Cl | Et | H | Br |
| CH₃ | Br | Cl | i-Pr | H | Br |
| CH₃ | Br | Cl | t-Bu | H | Br |
| CH₃ | Br | Cl | Me | Me | Br |
| CH₃ | Br | Br | Me | H | Cl |
| CH₃ | Br | Br | Et | H | Cl |
| CH₃ | Br | Br | i-Pr | H | Cl |
| CH₃ | Br | Br | t-Bu | H | Cl |
| CH₃ | Br | Br | Me | Me | Cl |
| CH₃ | Br | Br | Me | H | Br |
| CH₃ | Br | Br | Et | H | Br |
| CH₃ | Br | Br | i-Pr | H | Br |
| CH₃ | Br | Br | t-Bu | H | Br |
| CH₃ | Br | Br | Me | Me | Br |
| CH₃ | Br | OCH₂CF₃ | Me | H | Cl |
| CH₃ | Br | OCH₂CF₃ | Et | H | Cl |
| CH₃ | Br | OCH₂CF₃ | i-Pr | H | Cl |
| CH₃ | Br | OCH₂CF₃ | t-Bu | H | Cl |
| CH₃ | Br | OCH₂CF₃ | Me | Me | Cl |
| CH₃ | Br | OCH₂CF₃ | Me | H | Br |
| CH₃ | Br | OCH₂CF₃ | Et | H | Br |
| CH₃ | Br | OCH₂CF₃ | i-Pr | H | Br |
| CH₃ | Br | OCH₂CF₃ | t-Bu | H | Br |
| CH₃ | Br | OCH₂CF₃ | Me | Me | Br |
| CH₃ | I | CF₃ | Me | H | Cl |
| CH₃ | I | CF₃ | Et | H | Cl |
| CH₃ | I | CF₃ | i-Pr | H | Cl |
| CH₃ | I | CF₃ | t-Bu | H | Cl |
| CH₃ | I | CF₃ | Me | Me | Cl |
| CH₃ | I | CF₃ | Me | H | Br |
| CH₃ | I | CF₃ | Et | H | Br |
| CH₃ | I | CF₃ | i-Pr | H | Br |

TABLE 5-continued

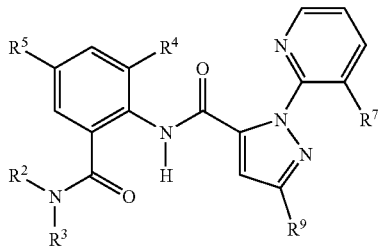

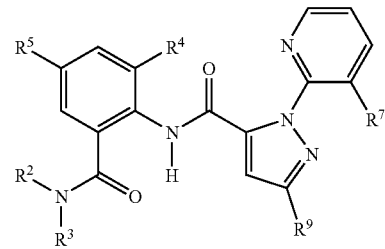

| R⁴ | R⁵ | R⁹ | R³ | R² | R⁷ |
|---|---|---|---|---|---|
| CH₃ | I | CF₃ | t-Bu | H | Br |
| CH₃ | I | CF₃ | Me | Me | Br |
| CH₃ | I | Cl | Me | H | Cl |
| CH₃ | I | Cl | Et | H | Cl |
| CH₃ | I | Cl | i-Pr | H | Cl |
| CH₃ | I | Cl | t-Bu | H | Cl |
| CH₃ | I | Cl | Me | Me | Cl |
| CH₃ | I | Cl | Me | H | Br |
| CH₃ | I | Cl | Et | H | Br |
| CH₃ | I | Cl | i-Pr | H | Br |
| CH₃ | I | Cl | t-Bu | H | Br |
| CH₃ | I | Cl | Me | Me | Br |
| CH₃ | I | Br | Me | H | Cl |
| CH₃ | I | Br | Et | H | Cl |
| CH₃ | I | Br | i-Pr | H | Cl |
| CH₃ | I | Br | t-Bu | H | Cl |
| CH₃ | I | Br | Me | Me | Cl |
| CH₃ | I | Br | Me | H | Br |
| CH₃ | I | Br | Et | H | Br |
| CH₃ | I | Br | i-Pr | H | Br |
| CH₃ | I | Br | t-Bu | H | Br |
| CH₃ | I | Br | Me | Me | Br |
| CH₃ | I | OCH₂CF₃ | Me | H | Cl |
| CH₃ | I | OCH₂CF₃ | Et | H | Cl |
| CH₃ | I | OCH₂CF₃ | i-Pr | H | Cl |
| CH₃ | I | OCH₂CF₃ | t-Bu | H | Cl |
| CH₃ | I | OCH₂CF₃ | Me | Me | Cl |
| CH₃ | I | OCH₂CF₃ | Me | H | Br |
| CH₃ | I | OCH₂CF₃ | Et | H | Br |
| CH₃ | I | OCH₂CF₃ | i-Pr | H | Br |
| CH₃ | I | OCH₂CF₃ | t-Bu | H | Br |
| CH₃ | I | OCH₂CF₃ | Me | Me | Br |
| CH₃ | CF₃ | CF₃ | Me | H | Cl |
| CH₃ | CF₃ | CF₃ | Et | H | Cl |
| CH₃ | CF₃ | CF₃ | i-Pr | H | Cl |
| CH₃ | CF₃ | CF₃ | t-Bu | H | Cl |
| CH₃ | CF₃ | CF₃ | Me | Me | Cl |
| CH₃ | CF₃ | CF₃ | Me | H | Br |
| CH₃ | CF₃ | CF₃ | Et | H | Br |
| CH₃ | CF₃ | CF₃ | i-Pr | H | Br |
| CH₃ | CF₃ | CF₃ | t-Bu | H | Br |
| CH₃ | CF₃ | CF₃ | Me | Me | Br |
| CH₃ | CF₃ | Cl | Me | H | Cl |
| CH₃ | CF₃ | Cl | Et | H | Cl |
| CH₃ | CF₃ | Cl | i-Pr | H | Cl |
| CH₃ | CF₃ | Cl | t-Bu | H | Cl |
| CH₃ | CF₃ | Cl | Me | Me | Cl |
| CH₃ | CF₃ | Cl | Me | H | Br |
| CH₃ | CF₃ | Cl | Et | H | Br |
| CH₃ | CF₃ | Cl | i-Pr | H | Br |
| CH₃ | CF₃ | Cl | t-Bu | H | Br |
| CH₃ | CF₃ | Cl | Me | Me | Br |
| CH₃ | CF₃ | Br | Me | H | Cl |
| CH₃ | CF₃ | Br | Et | H | Cl |
| CH₃ | CF₃ | Br | i-Pr | H | Cl |
| CH₃ | CF₃ | Br | t-Bu | H | Cl |
| CH₃ | CF₃ | Br | Me | Me | Cl |
| CH₃ | CF₃ | Br | Me | H | Br |
| CH₃ | CF₃ | Br | Et | H | Br |
| CH₃ | CF₃ | Br | i-Pr | H | Br |
| CH₃ | CF₃ | Br | t-Bu | H | Br |
| CH₃ | CF₃ | Br | Me | Me | Br |
| CH₃ | CF₃ | OCH₂CF₃ | Me | H | Cl |
| CH₃ | CF₃ | OCH₂CF₃ | Et | H | Cl |
| CH₃ | CF₃ | OCH₂CF₃ | i-Pr | H | Cl |
| CH₃ | CF₃ | OCH₂CF₃ | t-Bu | H | Cl |
| CH₃ | CF₃ | OCH₂CF₃ | Me | Me | Cl |
| CH₃ | CF₃ | OCH₂CF₃ | Me | H | Br |
| CH₃ | CF₃ | OCH₂CF₃ | Et | H | Br |
| CH₃ | CF₃ | OCH₂CF₃ | i-Pr | H | Br |
| CH₃ | CF₃ | OCH₂CF₃ | t-Bu | H | Br |
| CH₃ | CF₃ | OCH₂CF₃ | Me | Me | Br |
| CH₃ | Cl | Cl | n-Pr | H | Cl |
| CH₃ | Cl | Cl | n-Bu | H | Cl |
| CH₃ | Cl | Cl | s-Bu | H | Cl |
| CH₃ | Cl | Cl | i-Bu | H | Cl |
| CH₃ | Cl | Cl | Et | Me | Cl |
| F | F | CF₃ | Me | H | Cl |
| F | F | CF₃ | Et | H | Cl |
| F | F | CF₃ | i-Pr | H | Cl |
| F | F | CF₃ | t-Bu | H | Cl |
| F | F | CF₃ | Me | Me | Cl |
| F | F | CF₃ | Me | H | Br |
| F | F | CF₃ | Et | H | Br |
| F | F | CF₃ | i-Pr | H | Br |
| F | F | CF₃ | t-Bu | H | Br |
| F | F | CF₃ | Me | Me | Br |
| F | F | Cl | Me | H | Cl |
| F | F | Cl | Et | H | Cl |
| F | F | Cl | i-Pr | H | Cl |
| F | F | Cl | t-Bu | H | Cl |
| F | F | Cl | Me | Me | Cl |
| F | F | Cl | Me | H | Br |
| F | F | Cl | Et | H | Br |
| F | F | Cl | i-Pr | H | Br |
| F | F | Cl | t-Bu | H | Br |
| F | F | Cl | Me | Me | Br |
| F | F | Br | Me | H | Cl |
| F | F | Br | Et | H | Cl |
| F | F | Br | i-Pr | H | Cl |
| F | F | Br | t-Bu | H | Cl |
| F | F | Br | Me | Me | Cl |
| F | F | Br | Me | H | Br |
| F | F | Br | Et | H | Br |
| F | F | Br | i-Pr | H | Br |
| F | F | Br | t-Bu | H | Br |
| F | F | Br | Me | Me | Br |
| F | F | OCH₂CF₃ | Me | H | Cl |
| F | F | OCH₂CF₃ | Et | H | Cl |
| F | F | OCH₂CF₃ | i-Pr | H | Cl |
| F | F | OCH₂CF₃ | t-Bu | H | Cl |
| F | F | OCH₂CF₃ | Me | Me | Cl |
| F | F | OCH₂CF₃ | Me | H | Br |
| F | F | OCH₂CF₃ | Et | H | Br |
| F | F | OCH₂CF₃ | i-Pr | H | Br |
| F | F | OCH₂CF₃ | t-Bu | H | Br |
| F | F | OCH₂CF₃ | Me | Me | Br |
| F | Cl | CF₃ | Me | H | Cl |
| F | Cl | CF₃ | Et | H | Cl |
| F | Cl | CF₃ | i-Pr | H | Cl |
| F | Cl | CF₃ | t-Bu | H | Cl |
| F | Cl | CF₃ | Me | Me | Cl |
| F | Cl | CF₃ | Me | H | Br |
| F | Cl | CF₃ | Et | H | Br |
| F | Cl | CF₃ | i-Pr | H | Br |
| F | Cl | CF₃ | t-Bu | H | Br |
| F | Cl | CF₃ | Me | Me | Br |
| F | Cl | Cl | Me | H | Cl |

TABLE 5-continued

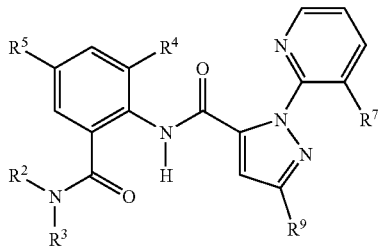

| R⁴ | R⁵ | R⁹ | R³ | R² | R⁷ |
|---|---|---|---|---|---|
| F | Cl | Cl | Et | H | Cl |
| F | Cl | Cl | i-Pr | H | Cl |
| F | Cl | Cl | t-Bu | H | Cl |
| F | Cl | Cl | Me | Me | Cl |
| F | Cl | Cl | Me | H | Br |
| F | Cl | Cl | Et | H | Br |
| F | Cl | Cl | i-Pr | H | Br |
| F | Cl | Cl | t-Bu | H | Br |
| F | Cl | Cl | Me | Me | Br |
| F | Cl | Br | Me | H | Cl |
| F | Cl | Br | Et | H | Cl |
| F | Cl | Br | i-Pr | H | Cl |
| F | Cl | Br | t-Bu | H | Cl |
| F | Cl | Br | Me | Me | Cl |
| F | Cl | Br | Me | H | Br |
| F | Cl | Br | Et | H | Br |
| F | Cl | Br | i-Pr | H | Br |
| F | Cl | Br | t-Bu | H | Br |
| F | Cl | Br | Me | Me | Br |
| F | Cl | OCH₂CF₃ | Me | H | Cl |
| F | Cl | OCH₂CF₃ | Et | H | Cl |
| F | Cl | OCH₂CF₃ | i-Pr | H | Cl |
| F | Cl | OCH₂CF₃ | t-Bu | H | Cl |
| F | Cl | OCH₂CF₃ | Me | Me | Cl |
| F | Cl | OCH₂CF₃ | Me | H | Br |
| F | Cl | OCH₂CF₃ | Et | H | Br |
| F | Cl | OCH₂CF₃ | i-Pr | H | Br |
| F | Cl | OCH₂CF₃ | t-Bu | H | Br |
| F | Cl | OCH₂CF₃ | Me | Me | Br |
| F | Br | CF₃ | Me | H | Cl |
| F | Br | CF₃ | Et | H | Cl |
| F | Br | CF₃ | i-Pr | H | Cl |
| F | Br | CF₃ | t-Bu | H | Cl |
| F | Br | CF₃ | Me | Me | Cl |
| F | Br | CF₃ | Me | H | Br |
| F | Br | CF₃ | Et | H | Br |
| F | Br | CF₃ | i-Pr | H | Br |
| F | Br | CF₃ | t-Bu | H | Br |
| F | Br | CF₃ | Me | Me | Br |
| F | Br | Cl | Me | H | Cl |
| F | Br | Cl | Et | H | Cl |
| F | Br | Cl | i-Pr | H | Cl |
| F | Br | Cl | t-Bu | H | Cl |
| F | Br | Cl | Me | Me | Cl |
| F | Br | Cl | Me | H | Br |
| F | Br | Cl | Et | H | Br |
| F | Br | Cl | i-Pr | H | Br |
| F | Br | Cl | t-Bu | H | Br |
| F | Br | Cl | Me | Me | Br |
| F | Br | Br | Me | H | Cl |
| F | Br | Br | Et | H | Cl |
| F | Br | Br | i-Pr | H | Cl |
| F | Br | Br | t-Bu | H | Cl |
| F | Br | Br | Me | Me | Cl |
| F | Br | Br | Me | H | Br |
| F | Br | Br | Et | H | Br |
| F | Br | Br | i-Pr | H | Br |
| F | Br | Br | t-Bu | H | Br |
| F | Br | Br | Me | Me | Br |
| F | Br | OCH₂CF₃ | Me | H | Cl |
| F | Br | OCH₂CF₃ | Et | H | Cl |
| F | Br | OCH₂CF₃ | i-Pr | H | Cl |
| F | Br | OCH₂CF₃ | t-Bu | H | Cl |
| F | Br | OCH₂CF₃ | Me | Me | Cl |

TABLE 5-continued

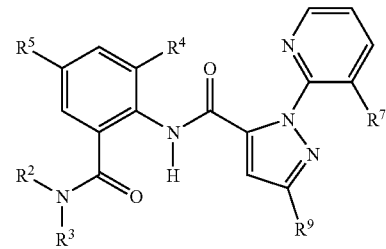

| R⁴ | R⁵ | R⁹ | R³ | R² | R⁷ |
|---|---|---|---|---|---|
| F | Br | OCH₂CF₃ | Me | H | Br |
| F | Br | OCH₂CF₃ | Et | H | Br |
| F | Br | OCH₂CF₃ | i-Pr | H | Br |
| F | Br | OCH₂CF₃ | t-Bu | H | Br |
| F | Br | OCH₂CF₃ | Me | Me | Br |
| F | I | CF₃ | Me | H | Cl |
| F | I | CF₃ | Et | H | Cl |
| F | I | CF₃ | i-Pr | H | Cl |
| F | I | CF₃ | t-Bu | H | Cl |
| F | I | CF₃ | Me | Me | Cl |
| F | I | CF₃ | Me | H | Br |
| F | I | CF₃ | Et | H | Br |
| F | I | CF₃ | i-Pr | H | Br |
| F | I | CF₃ | t-Bu | H | Br |
| F | I | CF₃ | Me | Me | Br |
| F | I | Cl | Me | H | Cl |
| F | I | Cl | Et | H | Cl |
| F | I | Cl | i-Pr | H | Cl |
| F | I | Cl | t-Bu | H | Cl |
| F | I | Cl | Me | Me | Cl |
| F | I | Cl | Me | H | Br |
| F | I | Cl | Et | H | Br |
| F | I | Cl | i-Pr | H | Br |
| F | I | Cl | t-Bu | H | Br |
| F | I | Cl | Me | Me | Br |
| F | I | Br | Me | H | Cl |
| F | I | Br | Et | H | Cl |
| F | I | Br | i-Pr | H | Cl |
| F | I | Br | t-Bu | H | Cl |
| F | I | Br | Me | Me | Cl |
| F | I | Br | Me | H | Br |
| F | I | Br | Et | H | Br |
| F | I | Br | i-Pr | H | Br |
| F | I | Br | t-Bu | H | Br |
| F | I | Br | Me | Me | Br |
| F | I | OCH₂CF₃ | Me | H | Cl |
| F | I | OCH₂CF₃ | Et | H | Cl |
| F | I | OCH₂CF₃ | i-Pr | H | Cl |
| F | I | OCH₂CF₃ | t-Bu | H | Cl |
| F | I | OCH₂CF₃ | Me | Me | Br |
| F | I | OCH₂CF₃ | Me | H | Br |
| F | I | OCH₂CF₃ | Et | H | Br |
| F | I | OCH₂CF₃ | i-Pr | H | Br |
| F | I | OCH₂CF₃ | t-Bu | H | Br |
| F | I | OCH₂CF₃ | Me | Me | Br |
| F | CF₃ | CF₃ | Me | H | Cl |
| F | CF₃ | CF₃ | Et | H | Cl |
| F | CF₃ | CF₃ | i-Pr | H | Cl |
| F | CF₃ | CF₃ | t-Bu | H | Cl |
| F | CF₃ | CF₃ | Me | Me | Cl |
| F | CF₃ | CF₃ | Me | H | Br |
| F | CF₃ | CF₃ | Et | H | Br |
| F | CF₃ | CF₃ | i-Pr | H | Br |
| F | CF₃ | CF₃ | t-Bu | H | Br |
| F | CF₃ | CF₃ | Me | Me | Br |
| F | CF₃ | Cl | Me | H | Cl |
| F | CF₃ | Cl | Et | H | Cl |
| F | CF₃ | Cl | i-Pr | H | Cl |
| F | CF₃ | Cl | t-Bu | H | Cl |
| F | CF₃ | Cl | Me | Me | Cl |
| F | CF₃ | Cl | Me | H | Br |
| F | CF₃ | Cl | Et | H | Br |
| F | CF₃ | Cl | i-Pr | H | Br |
| F | CF₃ | Cl | t-Bu | H | Br |

TABLE 5-continued

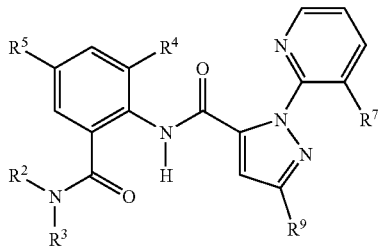

| R4 | R5 | R9 | R3 | R2 | R7 |
|---|---|---|---|---|---|
| F | CF3 | Cl | Me | Me | Br |
| F | CF3 | Br | Me | H | Cl |
| F | CF3 | Br | Et | H | Cl |
| F | CF3 | Br | i-Pr | H | Cl |
| F | CF3 | Br | t-Bu | H | Cl |
| F | CF3 | Br | Me | Me | Cl |
| F | CF3 | Br | Me | H | Br |
| F | CF3 | Br | Et | H | Br |
| F | CF3 | Br | i-Pr | H | Br |
| F | CF3 | Br | t-Bu | H | Br |
| F | CF3 | Br | Me | Me | Br |
| F | CF3 | OCH2CF3 | Me | H | Cl |
| F | CF3 | OCH2CF3 | Et | H | Cl |
| F | CF3 | OCH2CF3 | i-Pr | H | Cl |
| F | CF3 | OCH2CF3 | t-Bu | H | Cl |
| F | CF3 | OCH2CF3 | Me | Me | Cl |
| F | CF3 | OCH2CF3 | Me | H | Br |
| F | CF3 | OCH2CF3 | Et | H | Br |
| F | CF3 | OCH2CF3 | i-Pr | H | Br |
| F | CF3 | OCH2CF3 | t-Bu | H | Br |
| F | CF3 | OCH2CF3 | Me | Me | Br |
| CH3 | F | OCHF2 | Me | H | Cl |
| CH3 | F | OCHF2 | Et | H | Cl |
| CH3 | F | OCHF2 | i-Pr | H | Cl |
| CH3 | F | OCHF2 | t-Bu | H | Cl |
| CH3 | F | OCHF2 | Me | Me | Cl |
| CH3 | F | OCHF2 | Me | H | Br |
| CH3 | F | OCHF2 | Et | H | Br |
| CH3 | F | OCHF2 | i-Pr | H | Br |
| CH3 | F | OCHF2 | t-Bu | H | Br |
| CH3 | F | OCHF2 | Me | Me | Br |
| CH3 | Cl | OCHF2 | Me | H | Cl |
| CH3 | Cl | OCHF2 | Et | H | Cl |
| CH3 | Cl | OCHF2 | i-Pr | H | Cl |
| CH3 | Cl | OCHF2 | t-Bu | H | Cl |
| CH3 | Cl | OCHF2 | Me | Me | Cl |
| CH3 | Cl | OCHF2 | Me | H | Br |
| CH3 | Cl | OCHF2 | Et | H | Br |
| CH3 | Cl | OCHF2 | i-Pr | H | Br |
| CH3 | Cl | OCHF2 | t-Bu | H | Br |
| CH3 | Cl | OCHF2 | Me | Me | Br |
| CH3 | Br | OCHF2 | Me | H | Cl |
| CH3 | Br | OCHF2 | Et | H | Cl |
| CH3 | Br | OCHF2 | i-Pr | H | Cl |
| CH3 | Br | OCHF2 | t-Bu | H | Cl |
| CH3 | Br | OCHF2 | Me | Me | Cl |
| CH3 | Br | OCHF2 | Me | H | Br |
| CH3 | Br | OCHF2 | Et | H | Br |
| CH3 | Br | OCHF2 | i-Pr | H | Br |
| CH3 | Br | OCHF2 | t-Bu | H | Br |
| CH3 | Br | OCHF2 | Me | Me | Br |
| CH3 | I | OCHF2 | Me | H | Cl |
| CH3 | I | OCHF2 | Et | H | Cl |
| CH3 | I | OCHF2 | i-Pr | H | Cl |
| CH3 | I | OCHF2 | t-Bu | H | Cl |
| CH3 | I | OCHF2 | Me | Me | Cl |
| CH3 | I | OCHF2 | Me | H | Br |
| CH3 | I | OCHF2 | Et | H | Br |
| CH3 | I | OCHF2 | i-Pr | H | Br |
| CH3 | I | OCHF2 | t-Bu | H | Br |
| CH3 | I | OCHF2 | Me | Me | Br |
| CH3 | CF3 | OCHF2 | Me | H | Cl |
| CH3 | CF3 | OCHF2 | Et | H | Cl |
| CH3 | CF3 | OCHF2 | i-Pr | H | Cl |

TABLE 5-continued

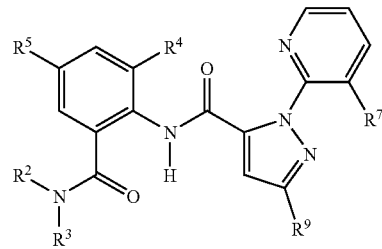

| R4 | R5 | R9 | R3 | R2 | R7 |
|---|---|---|---|---|---|
| CH3 | CF3 | OCHF2 | t-Bu | H | Cl |
| CH3 | CF3 | OCHF2 | Me | Me | Cl |
| CH3 | CF3 | OCHF2 | Me | H | Br |
| CH3 | CF3 | OCHF2 | Et | H | Br |
| CH3 | CF3 | OCHF2 | i-Pr | H | Br |
| CH3 | CF3 | OCHF2 | t-Bu | H | Br |
| CH3 | CF3 | OCHF2 | Me | Me | Br |
| F | F | OCHF2 | Me | H | Cl |
| F | F | OCHF2 | Et | H | Cl |
| F | F | OCHF2 | i-Pr | H | Cl |
| F | F | OCHF2 | t-Bu | H | Cl |
| F | F | OCHF2 | Me | Me | Cl |
| F | F | OCHF2 | Me | H | Br |
| F | F | OCHF2 | Et | H | Br |
| F | F | OCHF2 | i-Pr | H | Br |
| F | F | OCHF2 | t-Bu | H | Br |
| F | F | OCHF2 | Me | Me | Br |
| F | Cl | OCHF2 | Me | H | Cl |
| F | Cl | OCHF2 | Et | H | Cl |
| F | Cl | OCHF2 | i-Pr | H | Cl |
| F | Cl | OCHF2 | t-Bu | H | Cl |
| F | Cl | OCHF2 | Me | Me | Cl |
| F | Cl | OCHF2 | Me | H | Br |
| F | Cl | OCHF2 | Et | H | Br |
| F | Cl | OCHF2 | i-Pr | H | Br |
| F | Cl | OCHF2 | t-Bu | H | Br |
| F | Cl | OCHF2 | Me | Me | Br |
| F | Br | OCHF2 | Me | H | Cl |
| F | Br | OCHF2 | Et | H | Cl |
| F | Br | OCHF2 | i-Pr | H | Cl |
| F | Br | OCHF2 | t-Bu | H | Cl |
| F | Br | OCHF2 | Me | Me | Cl |
| F | Br | OCHF2 | Me | H | Br |
| F | Br | OCHF2 | Et | H | Br |
| F | Br | OCHF2 | i-Pr | H | Br |
| F | Br | OCHF2 | t-Bu | H | Br |
| F | Br | OCHF2 | Me | Me | Br |
| F | I | OCHF2 | Me | H | Cl |
| F | I | OCHF2 | Et | H | Cl |
| F | I | OCHF2 | i-Pr | H | Cl |
| F | I | OCHF2 | t-Bu | H | Cl |
| F | I | OCHF2 | Me | Me | Cl |
| F | I | OCHF2 | Me | H | Br |
| F | I | OCHF2 | Et | H | Br |
| F | I | OCHF2 | i-Pr | H | Br |
| F | I | OCHF2 | t-Bu | H | Br |
| F | I | OCHF2 | Me | Me | Br |
| F | CF3 | OCHF2 | Me | H | Cl |
| F | CF3 | OCHF2 | Et | H | Cl |
| F | CF3 | OCHF2 | i-Pr | H | Cl |
| F | CF3 | OCHF2 | t-Bu | H | Cl |
| F | CF3 | OCHF2 | Me | Me | Cl |
| F | CF3 | OCHF2 | Me | H | Br |
| F | CF3 | OCHF2 | Et | H | Br |
| F | CF3 | OCHF2 | i-Pr | H | Br |
| F | CF3 | OCHF2 | t-Bu | H | Br |
| F | CF3 | OCHF2 | Me | Me | Br |
| Cl | F | CF3 | Me | H | Cl |
| Cl | F | CF3 | Et | H | Cl |
| Cl | F | CF3 | i-Pr | H | Cl |
| Cl | F | CF3 | t-Bu | H | Cl |
| Cl | F | CF3 | Me | Me | Cl |
| Cl | F | CF3 | Me | H | Br |
| Cl | F | CF3 | Et | H | Br |

TABLE 5-continued

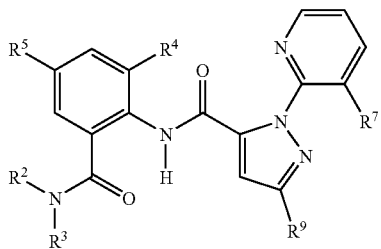

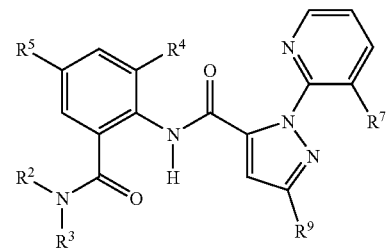

| R4 | R5 | R9 | R3 | R2 | R7 | R4 | R5 | R9 | R3 | R2 | R7 |
|---|---|---|---|---|---|---|---|---|---|---|---|
| Cl | F | CF3 | i-Pr | H | Br | Cl | Cl | OCH2CF3 | Et | H | Cl |
| Cl | F | CF3 | t-Bu | H | Br | Cl | Cl | OCH2CF3 | i-Pr | H | Cl |
| Cl | F | CF3 | Me | Me | Br | Cl | Cl | OCH2CF3 | t-Bu | H | Cl |
| Cl | F | Cl | Me | H | Cl | Cl | Cl | OCH2CF3 | Me | Me | Cl |
| Cl | F | Cl | Et | H | Cl | Cl | Cl | OCH2CF3 | Me | H | Br |
| Cl | F | Cl | i-Pr | H | Cl | Cl | Cl | OCH2CF3 | Et | H | Br |
| Cl | F | Cl | t-Bu | H | Cl | Cl | Cl | OCH2CF3 | i-Pr | H | Br |
| Cl | F | Cl | Me | Me | Cl | Cl | Cl | OCH2CF3 | t-Bu | H | Br |
| Cl | F | Cl | Me | H | Br | Cl | Cl | OCH2CF3 | Me | Me | Br |
| Cl | F | Cl | Et | H | Br | Cl | Br | CF3 | Me | H | Cl |
| Cl | F | Cl | i-Pr | H | Br | Cl | Br | CF3 | Et | H | Cl |
| Cl | F | Cl | t-Bu | H | Br | Cl | Br | CF3 | i-Pr | H | Cl |
| Cl | F | Cl | Me | Me | Br | Cl | Br | CF3 | t-Bu | H | Cl |
| Cl | F | Br | Me | H | Cl | Cl | Br | CF3 | Me | Me | Cl |
| Cl | F | Br | Et | H | Cl | Cl | Br | CF3 | Me | H | Br |
| Cl | F | Br | i-Pr | H | Cl | Cl | Br | CF3 | Et | H | Br |
| Cl | F | Br | t-Bu | H | Cl | Cl | Br | CF3 | i-Pr | H | Br |
| Cl | F | Br | Me | Me | Cl | Cl | Br | CF3 | t-Bu | H | Br |
| Cl | F | Br | Me | H | Br | Cl | Br | CF3 | Me | Me | Br |
| Cl | F | Br | Et | H | Br | Cl | Br | Cl | Me | H | Cl |
| Cl | F | Br | i-Pr | H | Br | Cl | Br | Cl | Et | H | Cl |
| Cl | F | Br | t-Bu | H | Br | Cl | Br | Cl | i-Pr | H | Cl |
| Cl | F | Br | Me | Me | Br | Cl | Br | Cl | t-Bu | H | Cl |
| Cl | F | OCH2CF3 | Me | H | Cl | Cl | Br | Cl | Me | Me | Cl |
| Cl | F | OCH2CF3 | Et | H | Cl | Cl | Br | Cl | Me | H | Br |
| Cl | F | OCH2CF3 | i-Pr | H | Cl | Cl | Br | Cl | Et | H | Br |
| Cl | F | OCH2CF3 | t-Bu | H | Cl | Cl | Br | Cl | i-Pr | H | Br |
| Cl | F | OCH2CF3 | Me | Me | Cl | Cl | Br | Cl | t-Bu | H | Br |
| Cl | F | OCH2CF3 | Me | H | Br | Cl | Br | Cl | Me | Me | Br |
| Cl | F | OCH2CF3 | Et | H | Br | Cl | Br | Br | Me | H | Cl |
| Cl | F | OCH2CF3 | i-Pr | H | Br | Cl | Br | Br | Et | H | Cl |
| Cl | F | OCH2CF3 | t-Bu | H | Br | Cl | Br | Br | i-Pr | H | Cl |
| Cl | F | OCH2CF3 | Me | Me | Br | Cl | Br | Br | t-Bu | H | Cl |
| Cl | Cl | CF3 | Me | H | Cl | Cl | Br | Br | Me | Me | Cl |
| Cl | Cl | CF3 | Et | H | Cl | Cl | Br | Br | Me | H | Br |
| Cl | Cl | CF3 | i-Pr | H | Cl | Cl | Br | Br | Et | H | Br |
| Cl | Cl | CF3 | t-Bu | H | Cl | Cl | Br | Br | i-Pr | H | Br |
| Cl | Cl | CF3 | Me | Me | Cl | Cl | Br | Br | t-Bu | H | Br |
| Cl | Cl | CF3 | Me | H | Br | Cl | Br | Br | Me | Me | Br |
| Cl | Cl | CF3 | Et | H | Br | Cl | Br | OCH2CF3 | Me | H | Cl |
| Cl | Cl | CF3 | i-Pr | H | Br | Cl | Br | OCH2CF3 | Et | H | Cl |
| Cl | Cl | CF3 | t-Bu | H | Br | Cl | Br | OCH2CF3 | i-Pr | H | Cl |
| Cl | Cl | CF3 | Me | Me | Br | Cl | Br | OCH2CF3 | t-Bu | H | Cl |
| Cl | Cl | Cl | Me | H | Cl | Cl | Br | OCH2CF3 | Me | Me | Cl |
| Cl | Cl | Cl | Et | H | Cl | Cl | Br | OCH2CF3 | Me | H | Br |
| Cl | Cl | Cl | i-Pr | H | Cl | Cl | Br | OCH2CF3 | Et | H | Br |
| Cl | Cl | Cl | t-Bu | H | Cl | Cl | Br | OCH2CF3 | i-Pr | H | Br |
| Cl | Cl | Cl | Me | Me | Cl | Cl | Br | OCH2CF3 | t-Bu | H | Br |
| Cl | Cl | Cl | Me | H | Br | Cl | Br | OCH2CF3 | Me | Me | Br |
| Cl | Cl | Cl | Et | H | Br | Cl | I | CF3 | Me | H | Cl |
| Cl | Cl | Cl | i-Pr | H | Br | Cl | I | CF3 | Et | H | Cl |
| Cl | Cl | Cl | t-Bu | H | Br | Cl | I | CF3 | i-Pr | H | Cl |
| Cl | Cl | Cl | Me | Me | Br | Cl | I | CF3 | t-Bu | H | Cl |
| Cl | Cl | Br | Me | H | Cl | Cl | I | CF3 | Me | Me | Cl |
| Cl | Cl | Br | Et | H | Cl | Cl | I | CF3 | Me | H | Br |
| Cl | Cl | Br | i-Pr | H | Cl | Cl | I | CF3 | Et | H | Br |
| Cl | Cl | Br | t-Bu | H | Cl | Cl | I | CF3 | i-Pr | H | Br |
| Cl | Cl | Br | Me | Me | Cl | Cl | I | CF3 | t-Bu | H | Br |
| Cl | Cl | Br | Me | H | Br | Cl | I | CF3 | Me | Me | Br |
| Cl | Cl | Br | Et | H | Br | Cl | I | Cl | Me | H | Cl |
| Cl | Cl | Br | i-Pr | H | Br | Cl | I | Cl | Et | H | Cl |
| Cl | Cl | Br | t-Bu | H | Br | Cl | I | Cl | i-Pr | H | Cl |
| Cl | Cl | Br | Me | Me | Br | Cl | I | Cl | t-Bu | H | Cl |
| Cl | Cl | OCH2CF3 | Me | H | Cl | Cl | I | Cl | Me | Me | Cl |

TABLE 5-continued

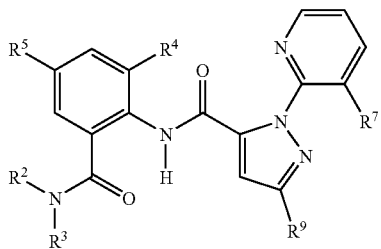

| R⁴ | R⁵ | R⁹ | R³ | R² | R⁷ |
|---|---|---|---|---|---|
| Cl | I | Cl | Me | H | Br |
| Cl | I | Cl | Et | H | Br |
| Cl | I | Cl | i-Pr | H | Br |
| Cl | I | Cl | t-Bu | H | Br. |
| Cl | I | Cl | Me | Me | Br |
| Cl | I | Br | Me | H | Cl |
| Cl | I | Br | Et | H | Cl |
| Cl | I | Br | i-Pr | H | Cl |
| Cl | I | Br | t-Bu | H | Cl |
| Cl | I | Br | Me | Me | Cl |
| Cl | I | Br | Me | H | Br |
| Cl | I | Br | Et | H | Br |
| Cl | I | Br | i-Pr | H | Br |
| Cl | I | Br | t-Bu | H | Br |
| Cl | I | Br | Me | Me | Br |
| Cl | I | OCH₂CF₃ | Me | H | Cl |
| Cl | I | OCH₂CF₃ | Et | H | Cl |
| Cl | I | OCH₂CF₃ | i-Pr | H | Cl |
| Cl | I | OCH₂CF₃ | t-Bu | H | Cl |
| Cl | I | OCH₂CF₃ | Me | Me | Cl |
| Cl | I | OCH₂CF₃ | Me | H | Br |
| Cl | I | OCH₂CF₃ | Et | H | Br |
| Cl | I | OCH₂CF₃ | i-Pr | H | Br |
| Cl | I | OCH₂CF₃ | t-Bu | H | Br |
| Cl | I | OCH₂CF₃ | Me | Me | Br |
| Cl | CF₃ | CF₃ | Me | H | Cl |
| Cl | CF₃ | CF₃ | Et | H | Cl |
| Cl | CF₃ | CF₃ | i-Pr | H | Cl |
| Cl | CF₃ | CF₃ | t-Bu | H | Cl |
| Cl | CF₃ | CF₃ | Me | Me | Cl |
| Cl | CF₃ | CF₃ | Me | H | Br |
| Cl | CF₃ | CF₃ | Et | H | Br |
| Cl | CF₃ | CF₃ | i-Pr | H | Br |
| Cl | CF₃ | CF₃ | t-Bu | H | Br |
| Cl | CF₃ | CF₃ | Me | Me | Br |
| Cl | CF₃ | Cl | Me | H | Cl |
| Cl | CF₃ | Cl | Et | H | Cl |
| Cl | CF₃ | Cl | i-Pr | H | Cl |
| Cl | CF₃ | Cl | t-Bu | H | Cl |
| Cl | CF₃ | Cl | Me | Me | Cl |
| Cl | CF₃ | Cl | Me | H | Br |
| Cl | CF₃ | Cl | Et | H | Br |
| Cl | CF₃ | Cl | i-Pr | H | Br |
| Cl | CF₃ | Cl | i-Bu | H | Br |
| Cl | CF₃ | Cl | Me | Me | Br |
| Cl | CF₃ | Br | Me | H | Cl |
| Cl | CF₃ | Br | Et | H | Cl |
| Cl | CF₃ | Br | i-Pr | H | Cl |
| Cl | CF₃ | Br | t-Bu | H | Cl |
| Cl | CF₃ | Br | Me | Me | Cl |
| Cl | CF₃ | Br | Me | H | Br |
| Cl | CF₃ | Br | Et | H | Br |
| Cl | CF₃ | Br | i-Pr | H | Br |
| Cl | CF₃ | Br | t-Bu | H | Br |
| Cl | CF₃ | Br | Me | Me | Br |
| Cl | CF₃ | OCH₂CF₃ | Me | H | Cl |
| Cl | CF₃ | OCH₂CF₃ | Et | H | Cl |
| Cl | CF₃ | OCH₂CF₃ | i-Pr | H | Cl |
| Cl | CF₃ | OCH₂CF₃ | t-Bu | H | Cl |
| Cl | CF₃ | OCH₂CF₃ | Me | Me | Cl |
| Cl | CF₃ | OCH₂CF₃ | Me | H | Br |
| Cl | CF₃ | OCH₂CF₃ | Et | H | Br |
| Cl | CF₃ | OCH₂CF₃ | i-Pr | H | Br |
| Cl | CF₃ | OCH₂CF₃ | t-Bu | H | Br |

TABLE 5-continued

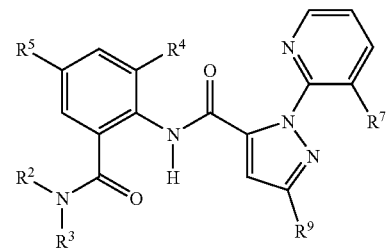

| R⁴ | R⁵ | R⁹ | R³ | R² | R⁷ |
|---|---|---|---|---|---|
| Cl | CF₃ | OCH₂CF₃ | Me | Me | Br |
| Cl | Cl | Cl | n-Pr | H | Cl |
| Cl | Cl | Cl | n-Bu | H | Cl |
| Cl | Cl | Cl | s-Bu | H | Cl |
| Cl | Cl | Cl | i-Bu | H | Cl |
| Cl | Cl | Cl | Et | Me | Cl |
| Br | F | CF₃ | Me | H | Cl |
| Br | F | CF₃ | Et | H | Cl |
| Br | F | CF₃ | i-Pr | H | Cl |
| Br | F | CF₃ | t-Bu | H | Cl |
| Br | F | CF₃ | Me | Me | Cl |
| Br | F | CF₃ | Me | H | Br |
| Br | F | CF₃ | Et | H | Br |
| Br | F | CF₃ | i-Pr | H | Br |
| Br | F | CF₃ | t-Bu | H | Br |
| Br | F | CF₃ | Me | Me | Br |
| Br | F | Cl | Me | H | Cl |
| Br | F | Cl | Et | H | Cl |
| Br | F | Cl | i-Pr | H | Cl |
| Br | F | Cl | t-Bu | H | Cl |
| Br | F | Cl | Me | Me | Cl |
| Br | F | Cl | Me | H | Br |
| Br | F | Cl | Et | H | Br |
| Br | F | Cl | i-Pr | H | Br |
| Br | F | Cl | t-Bu | H | Br |
| Br | F | Cl | Me | Me | Br |
| Br | F | Br | Me | H | Cl |
| Br | F | Br | Et | H | Cl |
| Br | F | Br | i-Pr | H | Cl |
| Br | F | Br | t-Bu | H | Cl |
| Br | F | Br | Me | Me | Cl |
| Br | F | Br | Me | H | Br |
| Br | F | Br | Et | H | Br |
| Br | F | Br | i-Pr | H | Br |
| Br | F | Br | t-Bu | H | Br |
| Br | F | Br | Me | Me | Br |
| Br | F | OCH₂CF₃ | Me | H | Cl |
| Br | F | OCH₂CF₃ | Et | H | Cl |
| Br | F | OCH₂CF₃ | i-Pr | H | Cl |
| Br | F | OCH₂CF₃ | t-Bu | H | Cl |
| Br | F | OCH₂CF₃ | Me | Me | Cl |
| Br | F | OCH₂CF₃ | Me | H | Br |
| Br | F | OCH₂CF₃ | Et | H | Br |
| Br | F | OCH₂CF₃ | i-Pr | H | Br |
| Br | F | OCH₂CF₃ | t-Bu | H | Br |
| Br | F | OCH₂CF₃ | Me | Me | Br |
| Br | Cl | CF₃ | Me | H | Cl |
| Br | Cl | CF₃ | Et | H | Cl |
| Br | Cl | CF₃ | i-Pr | H | Cl |
| Br | Cl | CF₃ | t-Bu | H | Cl |
| Br | Cl | CF₃ | Me | Me | Cl |
| Br | Cl | CF₃ | Me | H | Br |
| Br | Cl | CF₃ | Et | H | Br |
| Br | Cl | CF₃ | i-Pr | H | Br |
| Br | Cl | CF₃ | t-Bu | H | Br |
| Br | Cl | CF₃ | Me | Me | Br |
| Br | Cl | Cl | Me | H | Cl |
| Br | Cl | Cl | Et | H | Cl |
| Br | Cl | Cl | i-Pr | H | Cl |
| Br | Cl | Cl | t-Bu | H | Cl |
| Br | Cl | Cl | Me | Me | Cl |
| Br | Cl | Cl | Me | H | Br |
| Br | Cl | Cl | Et | H | Br |
| Br | Cl | Cl | i-Pr | H | Br |

TABLE 5-continued

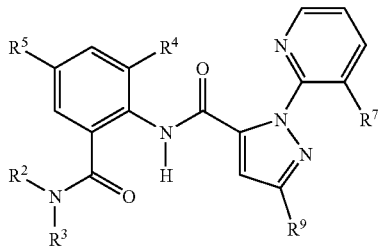

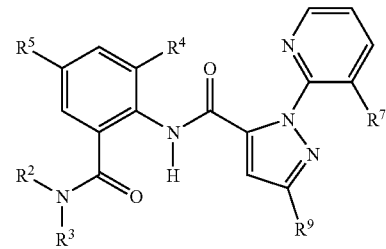

| $R^4$ | $R^5$ | $R^9$ | $R^3$ | $R^2$ | $R^7$ | | $R^4$ | $R^5$ | $R^9$ | $R^3$ | $R^2$ | $R^7$ |
|---|---|---|---|---|---|---|---|---|---|---|---|---|
| Br | Cl | Cl | t-Bu | H | Br | | Br | I | $CF_3$ | Me | H | Cl |
| Br | Cl | Cl | Me | Me | Br | | Br | I | $CF_3$ | Et | H | Cl |
| Br | Cl | Br | Me | H | Cl | | Br | I | $CF_3$ | i-Pr | H | Cl |
| Br | Cl | Br | Et | H | Cl | | Br | I | $CF_3$ | t-Bu | H | Cl |
| Br | Cl | Br | i-Pr | H | Cl | | Br | I | $CF_3$ | Me | Me | Cl |
| Br | Cl | Br | t-Bu | H | Cl | | Br | I | $CF_3$ | Me | H | Br |
| Br | Cl | Br | Me | Me | Cl | | Br | I | $CF_3$ | Et | H | Br |
| Br | Cl | Br | Me | H | Br | | Br | I | $CF_3$ | i-Pr | H | Br |
| Br | Cl | Br | Et | H | Br | | Br | I | $CF_3$ | t-Bu | H | Br |
| Br | Cl | Br | i-Pr | H | Br | | Br | I | $CF_3$ | Me | Me | Br |
| Br | Cl | Br | t-Bu | H | Br | | Br | I | Cl | Me | H | Cl |
| Br | Cl | Br | Me | Me | Br | | Br | I | Cl | Et | H | Cl |
| Br | Cl | $OCH_2CF_3$ | Me | H | Cl | | Br | I | Cl | i-Pr | H | Cl |
| Br | Cl | $OCH_2CF_3$ | Et | H | Cl | | Br | I | Cl | t-Bu | H | Cl |
| Br | Cl | $OCH_2CF_3$ | i-Pr | H | Cl | | Br | I | Cl | Me | Me | Cl |
| Br | Cl | $OCH_2CF_3$ | t-Bu | H | Cl | | Br | I | Cl | Me | H | Br |
| Br | Cl | $OCH_2CF_3$ | Me | Me | Cl | | Br | I | Cl | Et | H | Br |
| Br | Cl | $OCH_2CF_3$ | Me | H | Br | | Br | I | Cl | i-Pr | H | Br |
| Br | Cl | $OCH_2CF_3$ | Et | H | Br | | Br | I | Cl | t-Bu | H | Br |
| Br | Cl | $OCH_2CF_3$ | i-Pr | H | Br | | Br | I | Cl | Me | Me | Br |
| Br | Cl | $OCH_2CF_3$ | t-Bu | H | Br | | Br | I | Br | Me | H | Cl |
| Br | Cl | $OCH_2CF_3$ | Me | Me | Br | | Br | I | Br | Et | H | Cl |
| Br | Br | $CF_3$ | Me | H | Cl | | Br | I | Br | i-Pr | H | Cl |
| Br | Br | $CF_3$ | Et | H | Cl | | Br | I | Br | t-Bu | H | Cl |
| Br | Br | $CF_3$ | i-Pr | H | Cl | | Br | I | Br | Me | Me | Cl |
| Br | Br | $CF_3$ | t-Bu | H | Cl | | Br | I | Br | Me | H | Br |
| Br | Br | $CF_3$ | Me | Me | Cl | | Br | I | Br | Et | H | Br |
| Br | Br | $CF_3$ | Me | H | Br | | Br | I | Br | i-Pr | H | Br |
| Br | Br | $CF_3$ | Et | H | Br | | Br | I | Br | t-Bu | H | Br |
| Br | Br | $CF_3$ | i-Pr | H | Br | | Br | I | Br | Me | Me | Br |
| Br | Br | $CF_3$ | t-Bu | H | Br | | Br | I | $OCH_2CF_3$ | Me | H | Cl |
| Br | Br | $CF_3$ | Me | Me | Br | | Br | I | $OCH_2CF_3$ | Et | H | Cl |
| Br | Br | Cl | Me | H | Cl | | Br | I | $OCH_2CF_3$ | i-Pr | H | Cl |
| Br | Br | Cl | Et | H | Cl | | Br | I | $OCH_2CF_3$ | t-Bu | H | Cl |
| Br | Br | Cl | i-Pr | H | Cl | | Br | I | $OCH_2CF_3$ | Me | Me | Cl |
| Br | Br | Cl | t-Bu | H | Cl | | Br | I | $OCH_2CF_3$ | Me | H | Br |
| Br | Br | Cl | Me | Me | Cl | | Br | I | $OCH_2CF_3$ | Et | H | Br |
| Br | Br | Cl | Me | H | Br | | Br | I | $OCH_2CF_3$ | i-Pr | H | Br |
| Br | Br | Cl | Et | H | Br | | Br | I | $OCH_2CF_3$ | t-Bu | H | Br |
| Br | Br | Cl | i-Pr | H | Br | | Br | I | $OCH_2CF_3$ | Me | Me | Br |
| Br | Br | Cl | t-Bu | H | Br | | Br | $CF_3$ | $CF_3$ | Me | H | Cl |
| Br | Br | Cl | Me | Me | Br | | Br | $CF_3$ | $CF_3$ | Et | H | Cl |
| Br | Br | Br | Me | H | Cl | | Br | $CF_3$ | $CF_3$ | i-Pr | H | Cl |
| Br | Br | Br | Et | H | Cl | | Br | $CF_3$ | $CF_3$ | t-Bu | H | Cl |
| Br | Br | Br | i-Pr | H | Cl | | Br | $CF_3$ | $CF_3$ | Me | Me | Cl |
| Br | Br | Br | t-Bu | H | Cl | | Br | $CF_3$ | $CF_3$ | Me | H | Br |
| Br | Br | Br | Me | Me | Cl | | Br | $CF_3$ | $CF_3$ | Et | H | Br |
| Br | Br | Br | Me | H | Br | | Br | $CF_3$ | $CF_3$ | i-Pr | H | Br |
| Br | Br | Br | Et | H | Br | | Br | $CF_3$ | $CF_3$ | t-Bu | H | Br |
| Br | Br | Br | i-Pr | H | Br | | Br | $CF_3$ | $CF_3$ | Me | Me | Br |
| Br | Br | Br | t-Bu | H | Br | | Br | $CF_3$ | Cl | Me | H | Cl |
| Br | Br | Br | Me | Me | Br | | Br | $CF_3$ | Cl | Et | H | Cl |
| Br | Br | $OCH_2CF_3$ | Me | H | Cl | | Br | $CF_3$ | Cl | i-Pr | H | Cl |
| Br | Br | $OCH_2CF_3$ | Et | H | Cl | | Br | $CF_3$ | Cl | t-Bu | H | Cl |
| Br | Br | $OCH_2CF_3$ | i-Pr | H | Cl | | Br | $CF_3$ | Cl | Me | Me | Cl |
| Br | Br | $OCH_2CF_3$ | t-Bu | H | Cl | | Br | $CF_3$ | Cl | Me | H | Br |
| Br | Br | $OCH_2CF_3$ | Me | Me | Cl | | Br | $CF_3$ | Cl | Et | H | Br |
| Br | Br | $OCH_2CF_3$ | Me | H | Br | | Br | $CF_3$ | Cl | i-Pr | H | Br |
| Br | Br | $OCH_2CF_3$ | Et | H | Br | | Br | $CF_3$ | Cl | t-Bu | H | Br |
| Br | Br | $OCH_2CF_3$ | i-Pr | H | Br | | Br | $CF_3$ | Cl | Me | Me | Br |
| Br | Br | $OCH_2CF_3$ | t-Bu | H | Br | | Br | $CF_3$ | Br | Me | H | Cl |
| Br | Br | $OCH_2CF_3$ | Me | Me | Br | | Br | $CF_3$ | Br | Et | H | Cl |
| | | | | | | | Br | $CF_3$ | Br | i-Pr | H | Cl |
| | | | | | | | Br | $CF_3$ | Br | t-Bu | H | Cl |

TABLE 5-continued

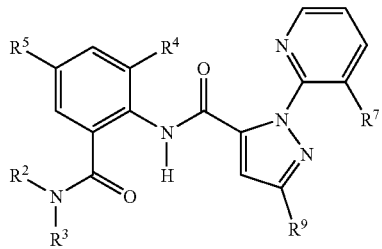

| R⁴ | R⁵ | R⁹ | R³ | R² | R⁷ |
|---|---|---|---|---|---|
| Br | CF₃ | Br | Me | Me | Cl |
| Br | CF₃ | Br | Me | H | Br |
| Br | CF₃ | Br | Et | H | Br |
| Br | CF₃ | Br | i-Pr | H | Br |
| Br | CF₃ | Br | t-Bu | H | Br |
| Br | CF₃ | Br | Me | Me | Br |
| Br | CF₃ | OCH₂CF₃ | Me | H | Cl |
| Br | CF₃ | OCH₂CF₃ | Et | H | Cl |
| Br | CF₃ | OCH₂CF₃ | i-Pr | H | Cl |
| Br | CF₃ | OCH₂CF₃ | t-Bu | H | Cl |
| Br | CF₃ | OCH₂CF₃ | Me | Me | Cl |
| Br | CF₃ | OCH₂CF₃ | Me | H | Br |
| Br | CF₃ | OCH₂CF₃ | Et | H | Br |
| Br | CF₃ | OCH₂CF₃ | i-Pr | H | Br |
| Br | CF₃ | OCH₂CF₃ | t-Bu | H | Br |
| Br | CF₃ | OCH₂CF₃ | Me | Me | Br |
| Cl | F | OCHF₂ | Me | H | Cl |
| Cl | F | OCHF₂ | Et | H | Cl |
| Cl | F | OCHF₂ | i-Pr | H | Cl |
| Cl | F | OCHF₂ | t-Bu | H | Cl |
| Cl | F | OCHF₂ | Me | Me | Cl |
| Cl | F | OCHF₂ | Me | H | Br |
| Cl | F | OCHF₂ | Et | H | Br |
| Cl | F | OCHF₂ | i-Pr | H | Br |
| Cl | F | OCHF₂ | t-Bu | H | Br |
| Cl | F | OCHF₂ | Me | Me | Br |
| Cl | Cl | OCHF₂ | Me | H | Cl |
| Cl | Cl | OCHF₂ | Et | H | Cl |
| Cl | Cl | OCHF₂ | i-Pr | H | Cl |
| Cl | Cl | OCHF₂ | t-Bu | H | Cl |
| Cl | Cl | OCHF₂ | Me | Me | Cl |
| Cl | Cl | OCHF₂ | Me | H | Br |
| Cl | Cl | OCHF₂ | Et | H | Br |
| Cl | Cl | OCHF₂ | i-Pr | H | Br |
| Cl | Cl | OCHF₂ | t-Bu | H | Br |
| Cl | Cl | OCHF₂ | Me | Me | Br |
| Cl | Br | OCHF₂ | Me | H | Cl |
| Cl | Br | OCHF₂ | Et | H | Cl |
| Cl | Br | OOHF₂ | i-Pr | H | Cl |
| Cl | Br | OOHF₂ | t-Bu | H | Cl |
| Cl | Br | OCHF₂ | Me | Me | Cl |
| Cl | Br | OCHF₂ | Me | H | Br |
| Cl | Br | OCHF₂ | Et | H | Br |
| Cl | Br | OCHF₂ | i-Pr | H | Br |
| Cl | Br | OCHF₂ | t-Bu | H | Br |
| Cl | Br | OCHF₂ | Me | Me | Br |
| Cl | I | OCHF₂ | Me | H | Cl |
| Cl | I | OCHF₂ | Et | H | Cl |
| Cl | I | OCHF₂ | i-Pr | H | Cl |
| Cl | I | OCHF₂ | t-Bu | H | Cl |
| Cl | I | OCHF₂ | Me | Me | Cl |
| Cl | I | OCHF₂ | Me | H | Br |
| Cl | I | OCHF₂ | Et | H | Br |
| Cl | I | OCHF₂ | i-Pr | H | Br |
| Cl | I | OCHF₂ | t-Bu | H | Br |
| Cl | I | OCHF₂ | Me | Me | Br |
| Cl | CF₃ | OCHF₂ | Me | H | Cl |
| Cl | CF₃ | OCHF₂ | Et | H | Cl |
| Cl | CF₃ | OCHF₂ | i-Pr | H | Cl |
| Cl | CF₃ | OCHF₂ | t-Bu | H | Cl |
| Cl | CF₃ | OCHF₂ | Me | Me | Cl |
| Cl | CF₃ | OCHF₂ | Me | H | Br |

TABLE 5-continued

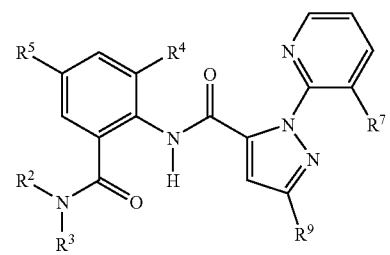

| R⁴ | R⁵ | R⁹ | R³ | R² | R⁷ |
|---|---|---|---|---|---|
| Cl | CF₃ | OCHF₂ | Et | H | Br |
| Cl | CF₃ | OCHF₂ | i-Pr | H | Br |
| Cl | CF₃ | OCHF₂ | t-Bu | H | Br |
| Cl | CF₃ | OCHF₂ | Me | Me | Br |
| Br | F | OCHF₂ | Me | H | Cl |
| Br | F | OCHF₂ | Et | H | Cl |
| Br | F | OCHF₂ | i-Pr | H | Cl |
| Br | F | OCHF₂ | t-Bu | H | Cl |
| Br | F | OCHF₂ | Me | Me | Cl |
| Br | F | OCHF₂ | Me | H | Br |
| Br | F | OCHF₂ | Et | H | Br |
| Br | F | OCHF₂ | i-Pr | H | Br |
| Br | F | OCHF₂ | t-Bu | H | Br |
| Br | F | OCHF₂ | Me | Me | Br |
| Br | Cl | OCHF₂ | Me | H | Cl |
| Br | Cl | OCHF₂ | Et | H | Cl |
| Br | Cl | OCHF₂ | i-Pr | H | Cl |
| Br | Cl | OCHF₂ | t-Bu | H | Cl |
| Br | Cl | OCHF₂ | Me | Me | Cl |
| Br | Cl | OCHF₂ | Me | H | Br |
| Br | Cl | OCHF₂ | Et | H | Br |
| Br | Cl | OCHF₂ | i-Pr | H | Br |
| Br | Cl | OCHF₂ | t-Bu | H | Br |
| Br | Cl | OCHF₂ | Me | Me | Br |
| Br | Br | OCHF₂ | Me | H | Cl |
| Br | Br | OCHF₂ | Et | H | Cl |
| Br | Br | OCHF₂ | i-Pr | H | Cl |
| Br | Br | OCHF₂ | t-Bu | H | Cl |
| Br | Br | OCHF₂ | Me | Me | Cl |
| Br | Br | OCHF₂ | Me | H | Br |
| Br | Br | OCHF₂ | Et | H | Br |
| Br | Br | OCHF₂ | i-Pr | H | Br |
| Br | Br | OCHF₂ | t-Bu | H | Br |
| Br | Br | OCHF₂ | Me | Me | Br |
| Br | I | OCHF₂ | Me | H | Cl |
| Br | I | OCHF₂ | Et | H | Cl |
| Br | I | OCHF₂ | i-Pr | H | Cl |
| Br | I | OCHF₂ | t-Bu | H | Cl |
| Br | I | OCHF₂ | Me | Me | Cl |
| Br | I | OCHF₂ | Me | H | Br |
| Br | I | OCHF₂ | Et | H | Br |
| Br | I | OCHF₂ | i-Pr | H | Br |
| Br | I | OCHF₂ | t-Bu | H | Br |
| Br | I | OCHF₂ | Me | Me | Br |
| Br | CF₃ | OCHF₂ | Me | H | Cl |
| Br | CF₃ | OCHF₂ | Et | H | Cl |
| Br | CF₃ | OCHF₂ | i-Pr | H | Cl |
| Br | CF₃ | OCHF₂ | t-Bu | H | Cl |
| Br | CF₃ | OCHF₂ | Me | Me | Cl |
| Br | CF₃ | OCHF₂ | Me | H | Br |
| Br | CF₃ | OCHF₂ | Et | H | Br |
| Br | CF₃ | OCHF₂ | i-Pr | H | Br |
| Br | CF₃ | OCHF₂ | t-Bu | H | Br |
| Br | CF₃ | OCHF₂ | Me | Me | Br |

What is claimed is:

1. A method for preparing a fused oxazinone of Formula 1,

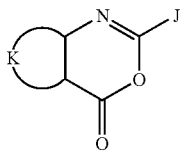

wherein
  K is, together with the two contiguous linking carbon atoms, a fused phenyl ring optionally substituted with from one to four substituents independently selected from G, U, W or $R^{13}$;
  J is a pyrrole ring or a pyrazole ring, each optionally substituted with from one to four substituents independently selected from G, U, W or $R^{13}$;
  each G is a 5- or 6-membered nonaromatic heterocyclic ring optionally with one or two ring members selected from the group consisting of C(=O), SO or $S(O)_2$, each optionally substituted with from one to four substituents independently selected from W;
  each U is a phenyl ring, a benzyl group, a benzoyl group, a 5- or 6-membered heteroaromatic ring, an aromatic 8-, 9- or 10-membered fused carbobicyclic ring system, an aromatic 8-, 9- or 10-membered fused heterobicyclic ring system, each optionally substituted with from one to four substituents independently selected from W;
  each W is independently $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, ($C_1$-$C_4$ alkyl)($C_3$-$C_6$ cycloalkyl)amino or $C_3$-$C_6$ trialkylsilyl;
  each $R^{12}$ is independently $R^{19}$C(=E)- or —O(Q=)P$(OR^{19})_2$;
  each $R^{13}$ is $B(OR^{17})_2$; $NH_2$; SH; thiocyanato; $C_3$-$C_8$ trialkylsilyloxy; $C_1$-$C_4$ alkyldisulfide; $SF_5$; $R^{19}$C(=E)-; $R^{19}$C(=E)M-; $R^{19}$MC(=E)-; $(R^{19})MC(=E)M$-; —OP(=Q)$(OR^{19})_2$; —$S(O)_2MR^{19}$; or $R^{19}S(O)_2M$-;
  each E independently O, S, $NR^{15}$, $NOR^{15}$, $NN(R^{15})_2$, N—S=O, N—CN or N—$NO_2$;
  each M is independently O, $NR^{18}$ or S;
  Q is O or S;
  each $R^{15}$ and each $R^{19}$ is independently H; $C_1$-$C_6$ alkyl optionally substituted with one, or more substituents selected from the group consisting of CN, $NO_2$, hydroxy, $C_1$-$C_4$ alkoxy, $C_1$-$C_4$ haloalkoxy, $C_1$-$C_4$ alkythio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $CO_2H$, $C_2$-$C_6$ alkoxycarbonyl, $C_2$-$C_6$ alkylcarbonyl, $C_3$-$C_6$ trialkylsilyl, and a phenyl ring optionally substituted with one to three substituents independently selected from W; $C_1$-$C_6$ haloalkyl; $C_3$-$C_6$ cycloalkyl; or a phenyl ring optionally substituted with from one to three substituents independently selected from W;
  each $R^{17}$ is independently H or $C_1$-$C_4$ alkyl; or $B(OR^{17})_2$ can form a ring wherein the two oxygen atoms are linked by a chain of two to three carbons optionally substituted with one or two substituents independently selected from methyl or $C_2$-$C_6$ alkoxycarbonyl; and
  each $R^{18}$ is independently H, $C_1$-$C_6$ alkyl or $C_1$-$C_6$ haloalkyl,
comprising:
  (1) contacting a carboxylic acid of Formula 2

$$J-CO_2H \qquad 2$$

with a sulfonyl chloride of Formula 4

$$LS(O)_2Cl \qquad 4$$

wherein
    L is selected from alkyl, haloalkyl, and phenyl optionally substituted with from one to three substituents independently selected from alkyl or halogen;
  in the presence of a Formula 3 compound selected from the group consisting of pyridine, quinoline, isoquinoline and pyridine substituted with alkyl, dimethylamino, or pyrrolidino, the nominal mole ratio of sulfonyl chloride to carboxylic acid being from about 0.75 to 1.5;
  (2) contacting the mixture prepared in (1) with an ortho-amino aromatic carboxylic acid of Formula 5

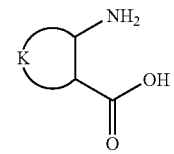

in the presence of a Formula 3 compound selected from the group consisting of pyridine, quinoline, isoquinoline and pyridine substituted with alkyl, dimethylamino, or pyrrolidino, the nominal mole ratio of the ortho-amino aromatic carboxylic acid to carboxylic acid charged in (1) being from about 0.8 to 1.2; and
  (3) adding additional sulfonyl chloride to the mixture prepared in (2), the nominal mole ratio of additional sulfonyl chloride added in (3) to carboxylic acid charged in (1) being at least about 0.5.

2. The method of claim 1 wherein in (1) the carboxylic acid of Formula 2 is contacted with sulfonyl chloride of Formula 4 in the presence of a Formula 3 compound selected from the group consisting of pyridine, 3-picoline, 2,6-lutidine, collidine, 2-picoline and 4-picoline and in (2) the mixture prepared in (1) is contacted with the ortho-amino aromatic carboxylic acid of Formula 5 in the presence of a Formula 3 compound selected from the group consisting of pyridine, 3-picoline, 2,6-lutidine, collidine, 2-picoline and 4-picoline.

3. The method of claim 1 wherein sulfonyl chloride of Formula 4 is selected from the group consisting of methanesulfonyl chloride, propanesulfonyl chloride and benzene sulfonyl chloride.

4. The method of claim 1 wherein the nominal mole ratio of sulfonyl chloride to carboxylic acid in (1) is from about 1.0 to 1.5; the nominal mole ratio of the ortho-amino aromatic carboxylic acid in (2) to carboxylic acid charged in (1) is from about 0.9 to 1.1; the nominal mole ratio of additional sulfonyl chloride added in (3) to carboxylic acid charged in (1) is from about 1.0 to 1.5.

5. The method of claim 4 wherein the nominal mole ratio of the Formula 3 compound charged in (1) to carboxylic acid charged in (1) is from about 1.0 to 2.0; additional Formula 3 compound is charged in (2); and the nominal mole ratio of the additional Formula 3 compound charged in (2) to carboxylic acid charged in (1) is from about 2.0 to 4.0.

6. The method of claim 1 wherein K is, together with the two contiguous linking carbon atoms, a fused phenyl ring optionally substituted with from one to four substituents independently selected from W or $R^{13}$.

7. The method of claim 1 wherein a compound of Formula 1a

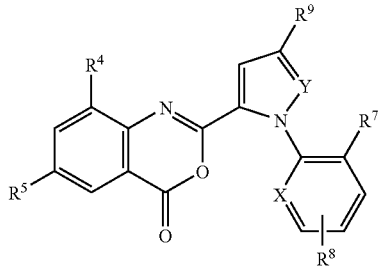

wherein
X is N or $CR^6$;
Y is N or CH;
$R^4$ is $C_1$-$C_4$ alkyl or halogen;
$R^5$ is H, $C_1$-$C_4$ alkyl, $C_1$-$C_4$ haloalkyl or halogen;
$R^6$ and $R^7$ are independently H, $C_1$-$C_4$ alkyl, $C_1$-$C_4$ haloalkyl, halogen, CN or $C_1$-$C_4$ haloalkoxy,
$R^8$ is H, $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, ($C_1$-$C_4$ alkyl)($C_3$-$C_6$ cycloalkyl)amino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl; and
$R^9$ is $CF_3$, $OCF_3$, $OCHF_2$, $OCH_2CF_3$ or halogen;
is prepared using a compound of Formula 2' as the Formula 2 compound and a compound of Formula 5' as the Formula 5 compound

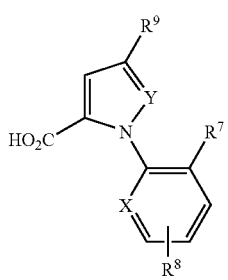

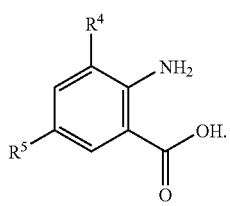

8. The method of claim 7 wherein
X is N;
Y is N;
$R^4$ is $CH_3$, F, Cl or Br;
$R^5$ is $CF_3$, F, Cl, Br or I;
$R^7$ is Cl or Br,
$R^8$ is H; and
$R^9$ is $CF_3$, $OCHF_2$, $OCH_2CF_3$, Cl or Br.

9. A method for preparing a fused oxazinone of Formula 1a

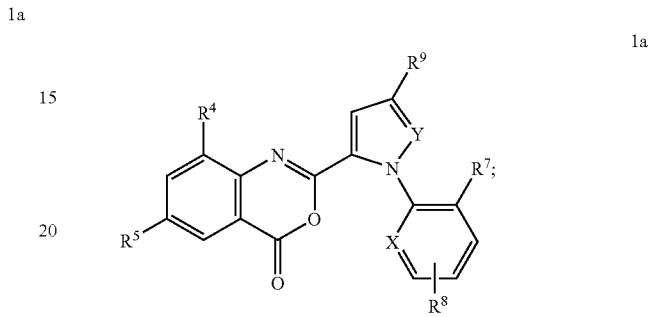

wherein
X is N or $CR_6$;
Y is N or CH;
$R^4$ is $C_1$-$C_4$ alkyl or halogen;
$R^5$ is H, $C_1$-$C_4$ alkyl, $C_1$-$C_4$ haloalkyl or halogen;
$R^6$ and $R^7$ are independently H, $C_1$-$C_4$ alkyl, $C_1$-$C_4$ haloalkyl, halogen, CN or $C_1$-$C_4$ haloalkoxy;
$R^8$ is H, $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_1$-$C_4$ dialkylamino, $C_3$-$C_6$ cycloalkylamino, ($C_1$-$C_4$ alkyl)($C_3$-$C_6$ cycloalkyl)amino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl;
$R^9$ is $CF_3$, $OCF_3$, $OCHF_2$, $OCH_2CF_3$, $S(O)_pCHF_3$, $S(O)_pCHF_2$ or halogen; and
p is 0, 1 or 2;
comprising:
(1) contacting a carboxylic acid of Formula 2'

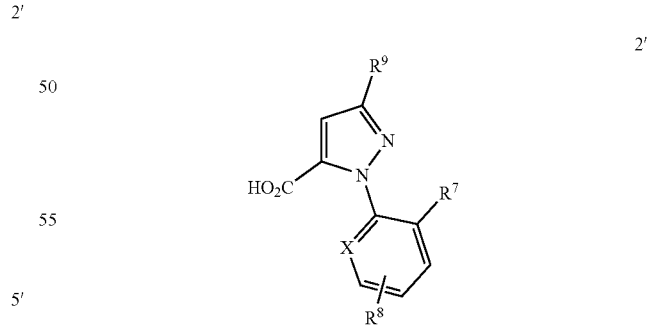

with a sulfonyl chloride of Formula 4

$$LS(O)_2Cl \qquad 4$$

wherein
L is selected from alkyl, haloalkyl, and phenyl optionally substituted with from one to three substituents independently selected from alkyl or halogen;

in the presence of a Formula 3 compound selected from the group consisting of pyridine, quinoline, isoquinoline and pyridine substituted with alkyl, dimethylamino, or pyrrolidino, the nominal mole ratio of sulfonyl chloride to carboxylic acid being from about 0.75 to 1.5;

(2) contacting the mixture prepared in (1) with an ortho-amino aromatic carboxylic acid of Formula 5'

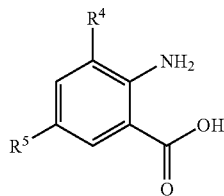

in the presence of a Formula 3 compound selected from the group consisting of pyridine, quinoline, isoquinoline and pyridine substituted with alkyl, dimethylamino, or pyrrolidino, the nominal mole ratio of the ortho-amino aromatic carboxylic acid to carboxylic acid charged in (1) being from about 0.8 to 1.2; and (3) adding additional sulfonyl chloride to the mixture prepared in (2), the nominal mole ratio of additional sulfonyl chloride added in (3) to carboxylic acid charged in (1) being at least about 0.5.

10. The method of claim 9 wherein in (1) the carboxylic acid of Formula 2 is contacted with sulfonyl chloride of Formula 4 in the presence of a Formula 3 compound is selected from the group consisting of pyyridine, 3-picoline, 2,6-lutidine, collidine, 2-picoline and 4-picoline and in (2) the mixture prepared in (1) is contacted with the ortho-amino aromatic carboxylic acid of Formula 5 in the presence of a Formula 3 compound selected from the group consisting of pyridine, 3-picoline, 2,6-lutidine, collidine, 2-picoline and 4-picoline.

11. The method of claim 9 wherein sulfonyl chloride of Formula 4 is selected from the group consisting of methanesulfonyl chloride, propanesulfonyl chloride and benzene sulfonyl chloride.

12. The method of claim 9 wherein the nominal mole ratio of sulfonyl chloride to carboxylic acid in (1) is from about 1.0 to 1.5; the nominal mole ratio of the an ortho-amino aromatic carboxylic acid in (2) to carboxylic acid charged in (1) is from about 0.9 to 1.1; the nominal mole ratio of additional sulfonyl chloride added in (3) to carboxylic acid charged in (1) is from about 1.0 to 1.5.

13. The method of claim 12 wherein the nominal mole ratio of the Formula 3 compound charged in (1) to carboxylic acid charged in (1) is from about 1.0 to 2.0; additional Formula 3 compound is charged in (2); and the nominal mole ratio of the additional Formula 3 compound charged in (2) to carboxylic acid charged in (1) is from about 2.0 to 4.0.

* * * * *

UNITED STATES PATENT AND TRADEMARK OFFICE
CERTIFICATE OF CORRECTION

| | | |
|---|---|---|
| PATENT NO. | : 7,339,057 B2 | Page 1 of 1 |
| APPLICATION NO. | : 10/518324 | |
| DATED | : March 4, 2008 | |
| INVENTOR(S) | : Eric Deguyon Taylor | |

It is certified that error appears in the above-identified patent and that said Letters Patent is hereby corrected as shown below:

Column 83, line 22, "heterocyclie" should read --heterocyclic--; line 23, after the word "optionally" insert --substituted--; line 48, before the word "independently" insert --is--; line 53, after the word "one" delete the ",".

Column 86, line 6, replace the "," at the end of the line with a ";"; line 41, "$S(O)_pCHF_3$" should read --$S(O)_pCHF_2$--.

Signed and Sealed this
Third Day of July, 2012

David J. Kappos
*Director of the United States Patent and Trademark Office*